US012594293B2

(12) United States Patent
Shay et al.

(10) Patent No.: US 12,594,293 B2
(45) Date of Patent: Apr. 7, 2026

(54) USE OF 6-THIO-dG TO TREAT THERAPY-RESISTANT TELOMERASEPOSITIVE PEDIATRIC BRAIN TUMORS

(71) Applicants: The Board of Regents of The University of Texas System, Austin, TX (US); Children's Hospital Medical Center, Cincinnati, OH (US)

(72) Inventors: Jerry Shay, Dallas, TX (US); Rachid Drissi, Cincinnati, OH (US)

(73) Assignees: The Board of Regents of The University of Texas System, Austin, TX (US); Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 18/511,417

(22) Filed: Nov. 16, 2023

(65) Prior Publication Data

US 2024/0189336 A1 Jun. 13, 2024

Related U.S. Application Data

(63) Continuation of application No. 16/982,979, filed as application No. PCT/US2019/023596 on Mar. 22, 2019, now abandoned.

(60) Provisional application No. 62/646,820, filed on Mar. 22, 2018.

(51) Int. Cl.
    *A61K 31/708* (2006.01)
    *A61K 45/06* (2006.01)
    *A61P 35/00* (2006.01)

(52) U.S. Cl.
    CPC ............ *A61K 31/708* (2013.01); *A61P 35/00* (2018.01); *A61K 45/06* (2013.01)

(58) Field of Classification Search
    CPC ....... A61K 31/708; A61K 45/06; A61P 35/00; A61P 35/04
    See application file for complete search history.

(56) References Cited

U.S. PATENT DOCUMENTS

| | | | |
|---|---|---|---|
| 2014/0303239 A1* | 10/2014 | Shay ...................... | A61P 35/00 514/48 |
| 2018/0036331 A1 | 2/2018 | Shay et al. | |
| 2019/0282600 A1 | 9/2019 | Villanueva | |
| 2019/0298751 A1 | 10/2019 | Shay et al. | |
| 2019/0388453 A1 | 12/2019 | Shay et al. | |
| 2021/0023107 A1 | 1/2021 | Shay et al. | |
| 2021/0113602 A1 | 4/2021 | Shay et al. | |
| 2021/0290652 A1 | 9/2021 | Shay et al. | |

FOREIGN PATENT DOCUMENTS

WO      WO 2017/205756      11/2017

OTHER PUBLICATIONS

Brown et al., "Targeting DNA Repair in Cancer: Beyond PARP Inhibitors," *Cancer Discov*, 7(1):20-37, 2017.

Dikmen et al., "In vivo inhibition of lung cancer by GRN163L: a novel human telomerase inhibitor," *Cancer Res*, 65(17):7866-7873, 2005.

Dorris et al., "Prognostic significance of telomere maintenance mechanisms in pediatric high-grade gliomas," *J Neurooncol*, 117(1):67-76, 2014.

Feldser et al., "Telomere dysfunction and the initiation of genome instability," *Nat Rev Cancer*, 3(8):623-627, 2003.

Hochreiter et al., "Telomerase template antagonist GRN163L disrupts telomere maintenance, tumor growth, and metastasis of breast cancer," *Clin Cancer Res*, 12(10):3184-3192, 2006.

Mender et al., "A novel telomerase substrate precursor rapidly induces telomere dysfunction in telomerase positive cancer cells but not telomerase silent normal cells," *Oncoscience*, 2(8):693-695, 2015.

Mender et al., "Induction of telomere dysfunction mediated by the telomerase substrate precursor 6-thio-2'-deoxyguanosine," *Cancer Discov*, 5(1):82-95, 2015.

Mender, "The in vitro and in vivo effects of telomerase substrate 6-thio-2'-deoxyguanosince," PhD Thesis, Hacettepe University Institute of Health Sciences, 2014.

(Continued)

*Primary Examiner* — Pancham Bakshi
(74) *Attorney, Agent, or Firm* — pH IP Law

(57) ABSTRACT

Brain tumors remain the leading cause of cancer-related deaths in children and often are associated with long-term sequelae among survivors of current therapies. Telomerase and telomeres play important roles in cancer, representing attractive therapeutic targets to treat children with poor-prognosis brain tumors such as diffuse intrinsic pontine glioma (DIPG), high-grade glioma (HGG) and high-risk medulloblastoma (MB). It has shown that DIPG, HGG and MB frequently express telomerase activity. It is now shown that the telomerase-dependent incorporation of 6-thio-2'de-oxyguanosine (6-thio-dG), a telomerase substrate precursor analog, into telomeres leads to telomere dysfunction-in-duced foci (TIFs) along with extensive genomic DNA damage, cell growth inhibition and cell death of primary stem-like cells derived from patients with DIPG, HGG and MB. Importantly, the effect of 6-thio-dG is persistent even after drug withdrawal. Treatment with 6-thio-dG elicits a sequential activation of ATR and ATM pathways and induces $G_2$/M arrest. In vivo, treatment of mice bearing MB xenografts with 6-thio-dG delays tumor growth, increases in-tumor TIFs and apoptosis. Furthermore, 6-thio-dG crosses the blood-brain barrier and specifically targets tumor cells in an orthotopic mouse model of DIPG. Together, these findings suggest that 6-thio-dG is a promising approach to treat therapy-resistant telomerase-positive pediatric brain tumors.

9 Claims, 35 Drawing Sheets

Specification includes a Sequence Listing.

(56)                    References Cited

OTHER PUBLICATIONS

Office Action issued in U.S. Appl. No. 16/982,979, mailed Apr. 18, 2022.

Office Action issued in U.S. Appl. No. 16/982,979, mailed Dec. 10, 2021.

Office Action issued in U.S. Appl. No. 16/982,979, mailed Nov. 16, 2022.

PCT International Preliminary Report on Patentability issued in International Application No. PCT/US2019/023596, mailed Oct. 1, 2020.

PCT International Search Report and Written Opinion issued in International Application No. PCT/US2019/023596, mailed Jul. 2, 2019.

Salloum et al., "A molecular biology and phase II study of imetelstat (GRN163L) in children with recurrent or refractory central nervous system malignancies: a pediatric brain tumor consortium study," *J Neurooncol.*, 129(3):443-451, 2016.

Sengupta et al., "Induced telomere damage to treat expressing therapy-resistant pediatric brain tumors," *Mol Cancer Ther*, 17(7):1504-1514, 2018.

Halford, "The challenge of treating childhood brain cancers," *Chemical & Engineering News*, 101(27):22-26, 2023.

\* cited by examiner

From FIG. 2C-4

From FIG. 2C-3

From FIG. 2D

To FIG. 2D-3

From FIG. 2D

To FIG. 2D-3

From FIG. 2D-2

From FIG. 2D-1

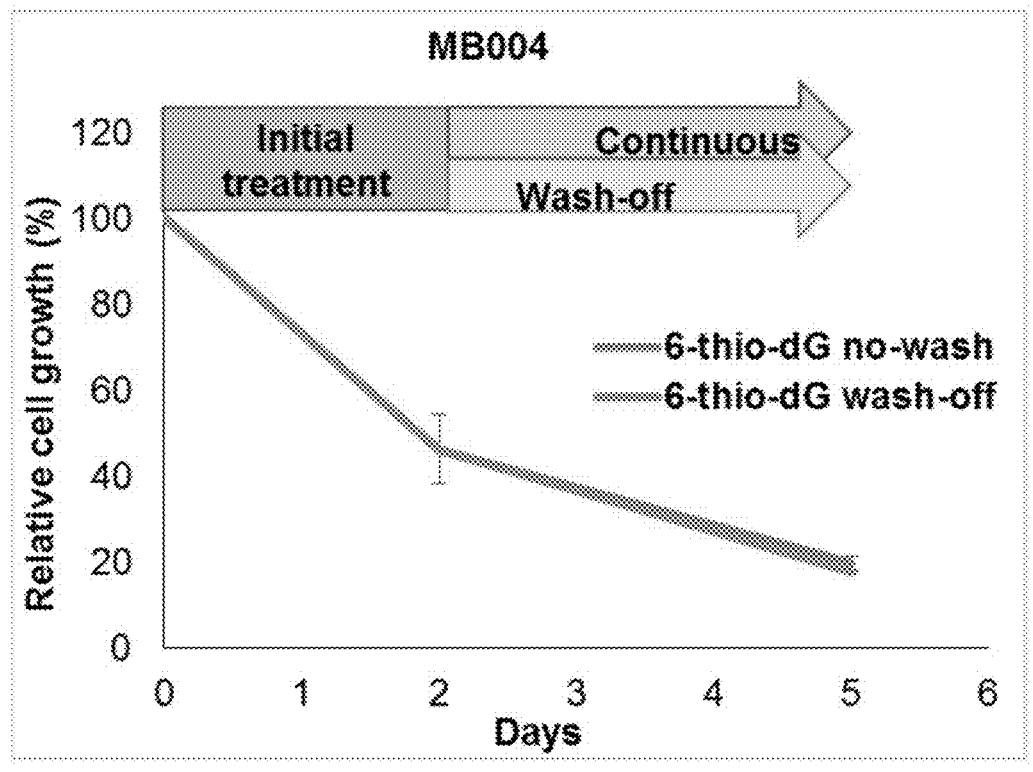
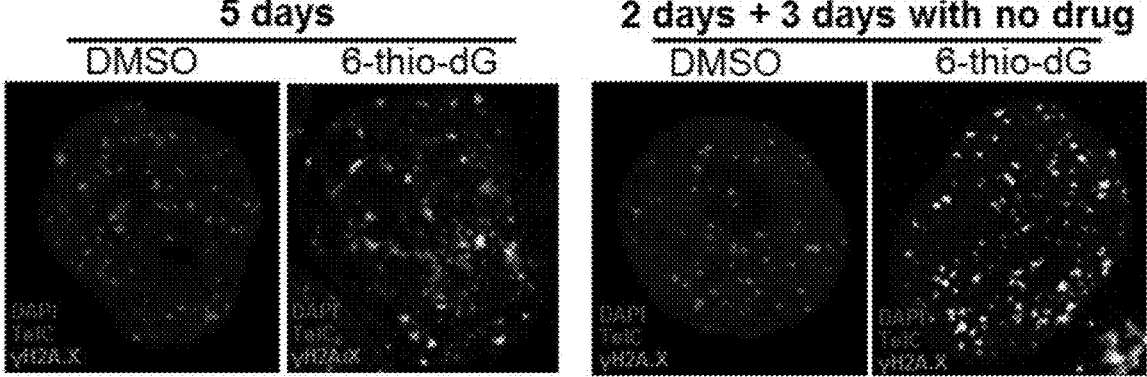
FIG. 3D

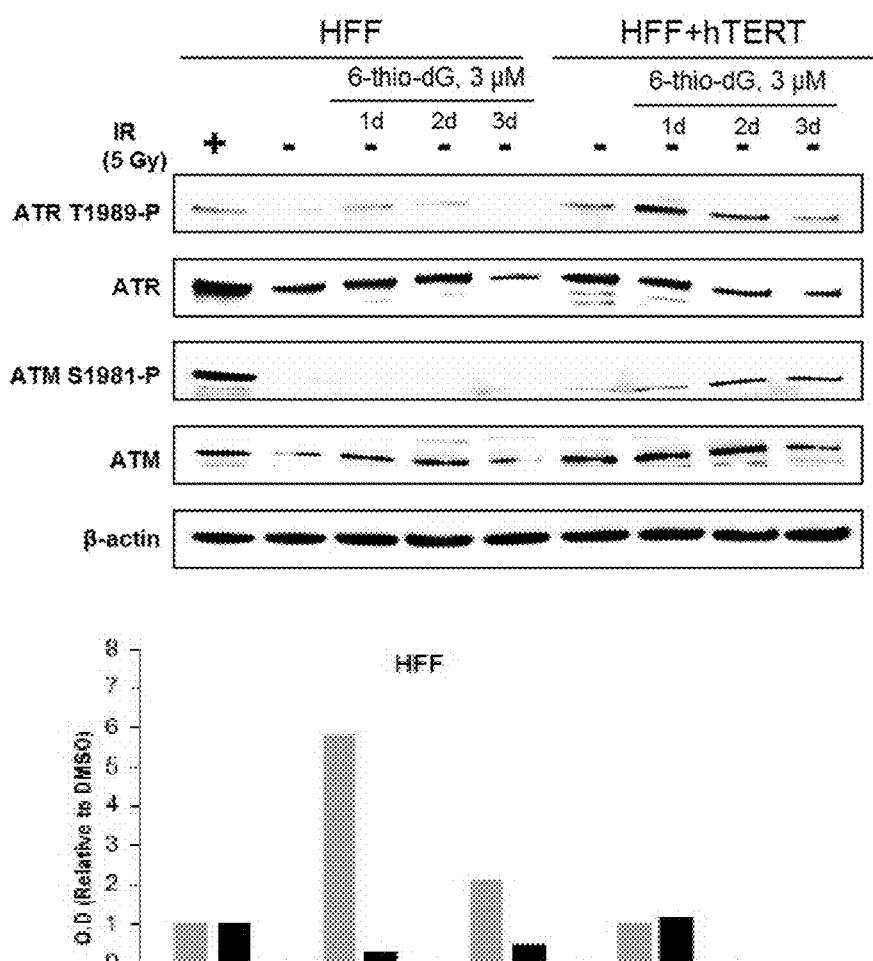
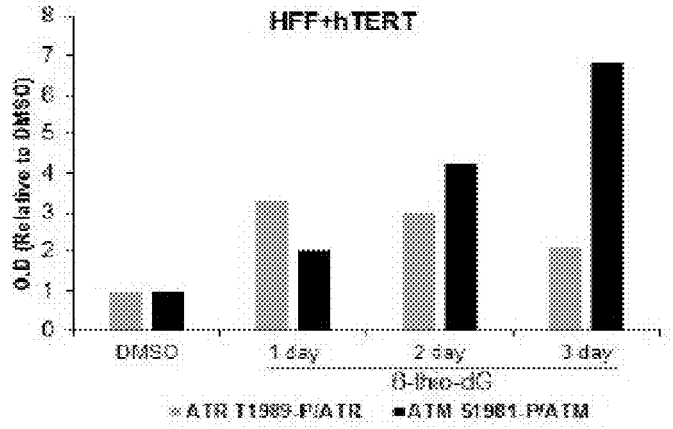
FIG. 4A

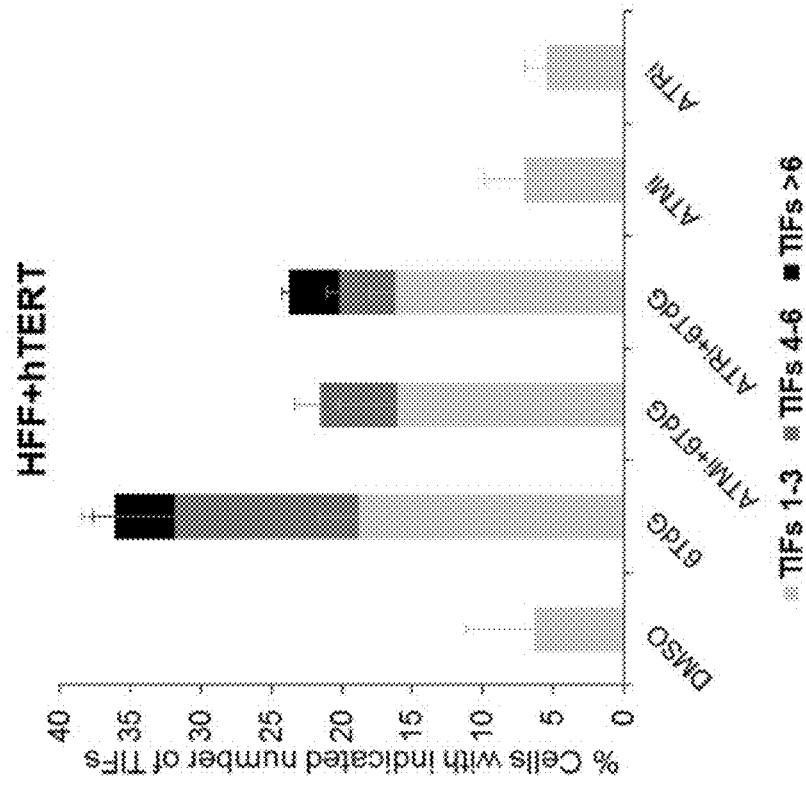
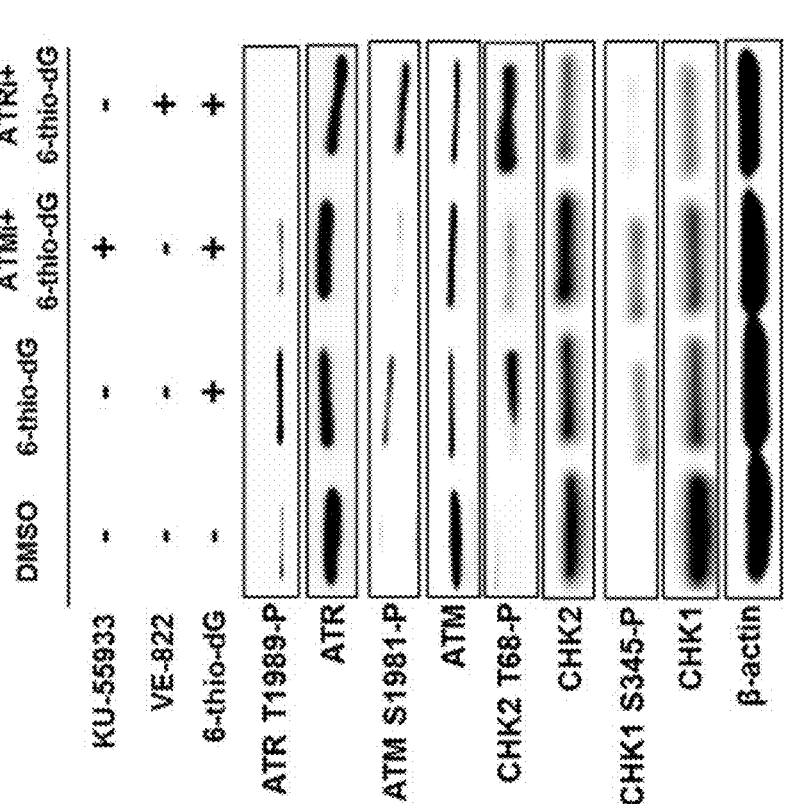
FIG. 4C

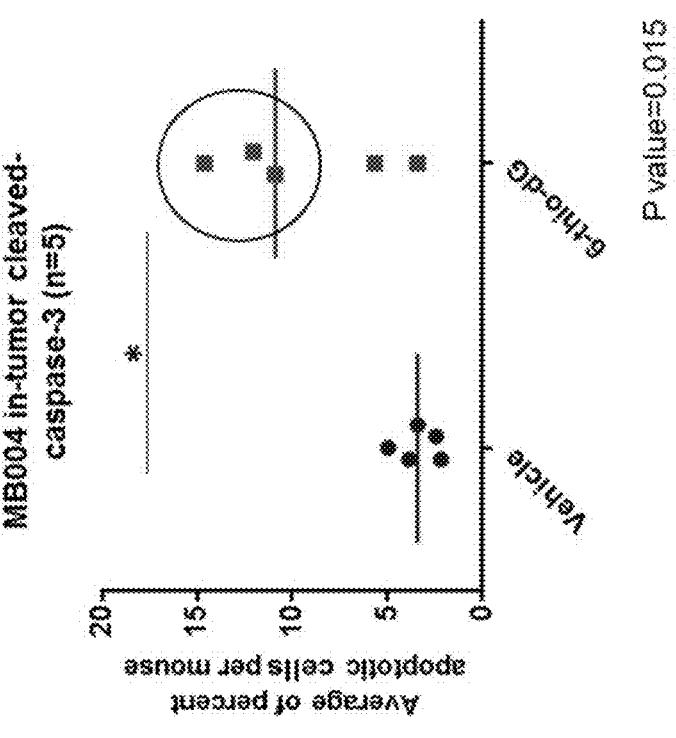
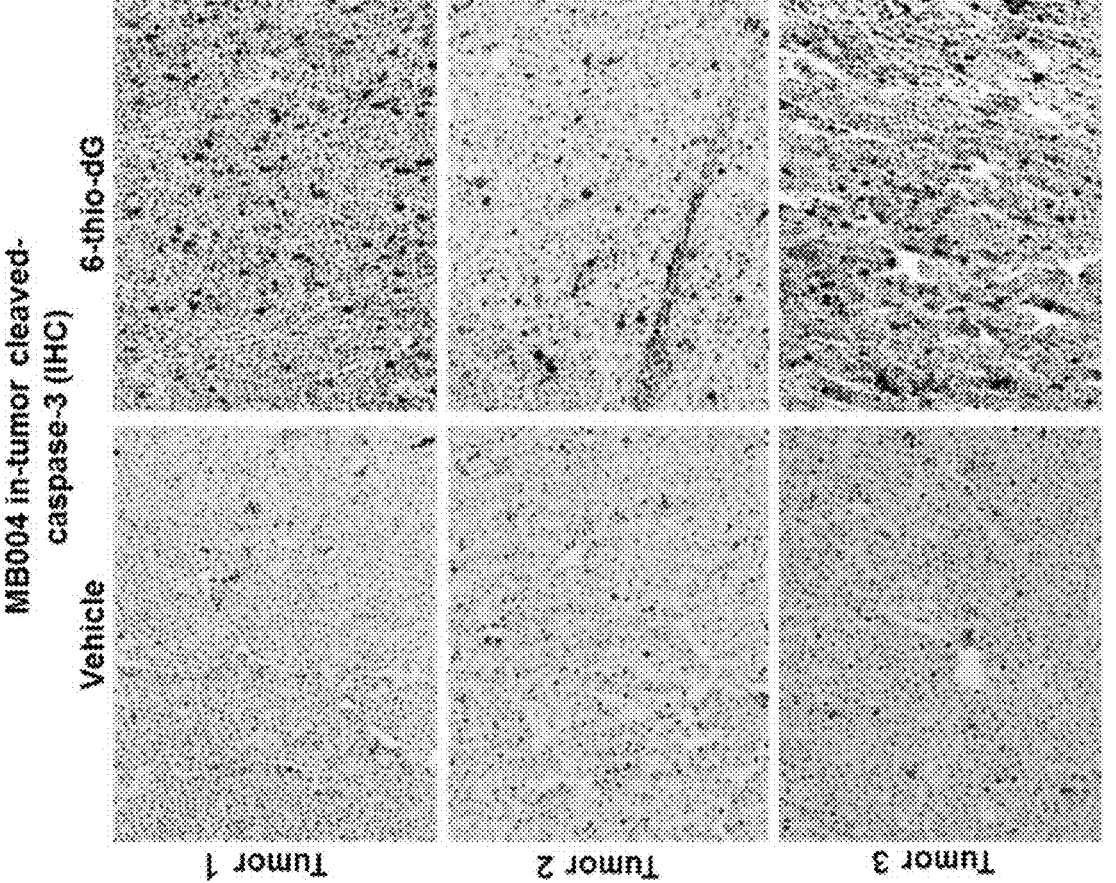
FIG. 6C

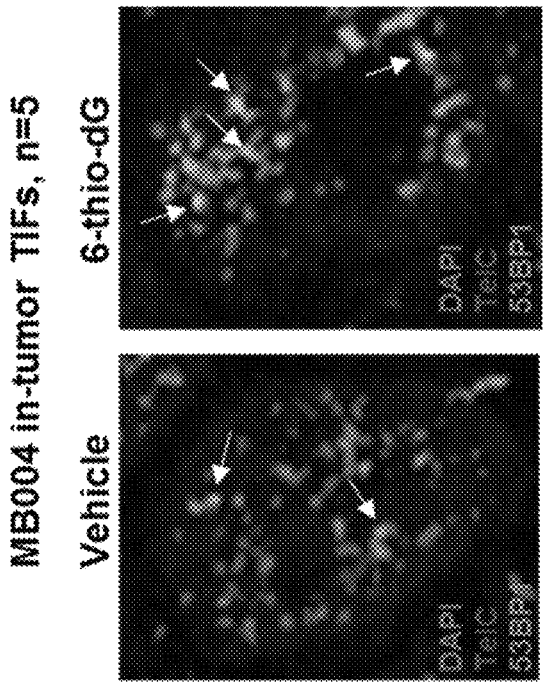
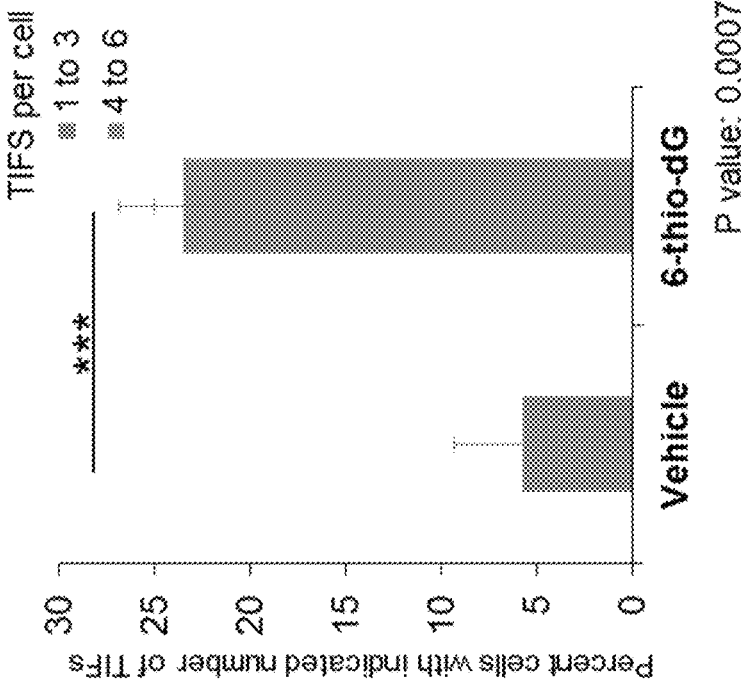
FIG. 6E

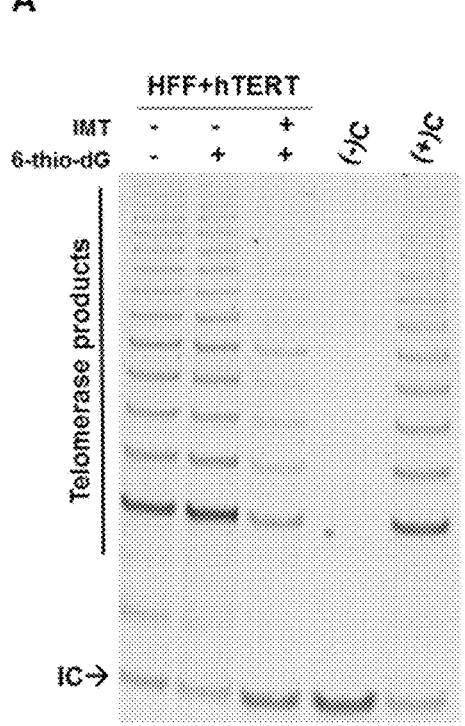
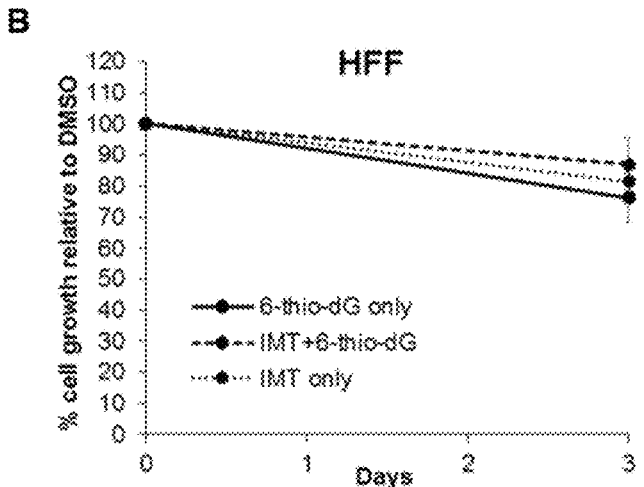
FIGS. 8A-B

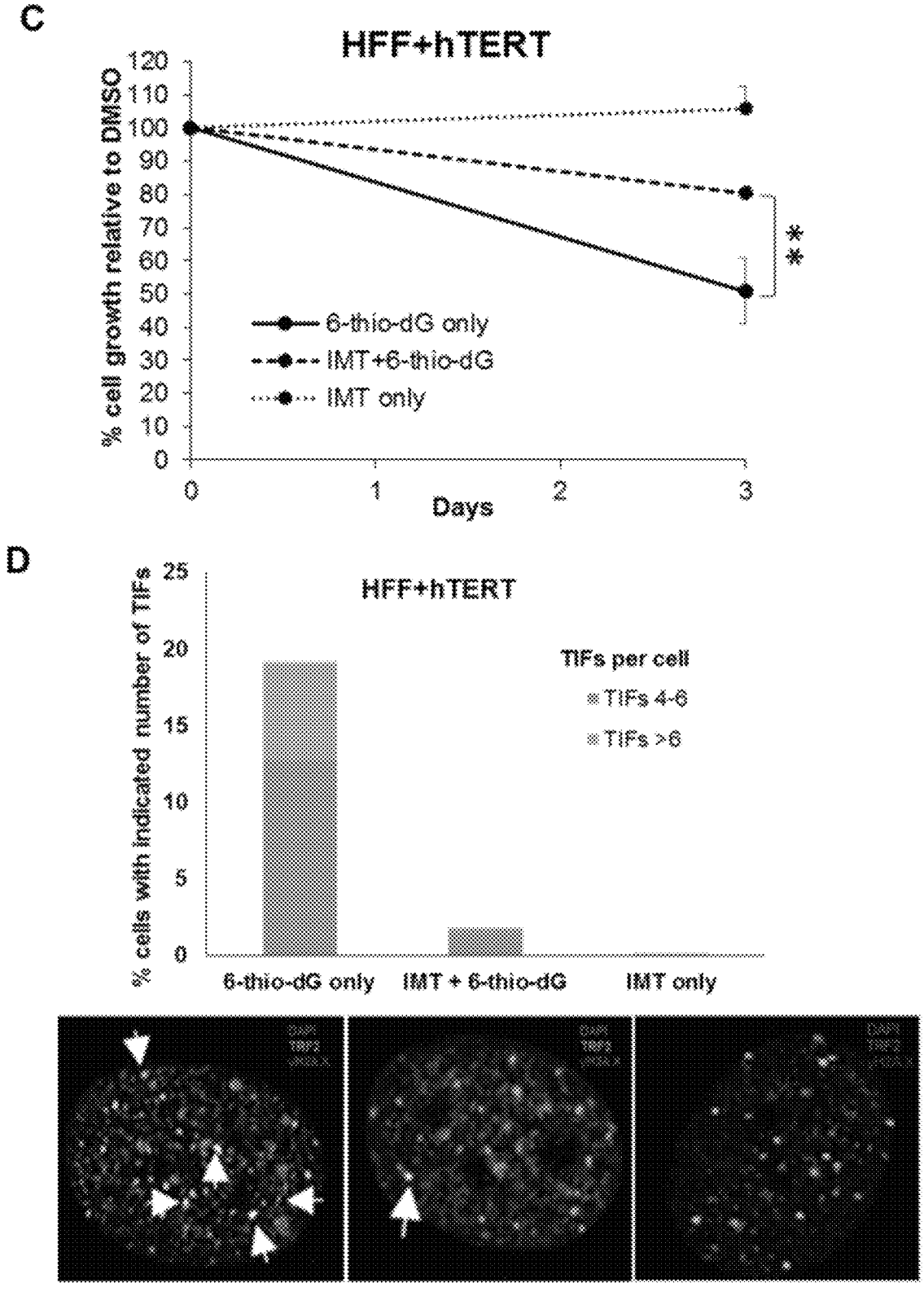
FIGS. 8C-D

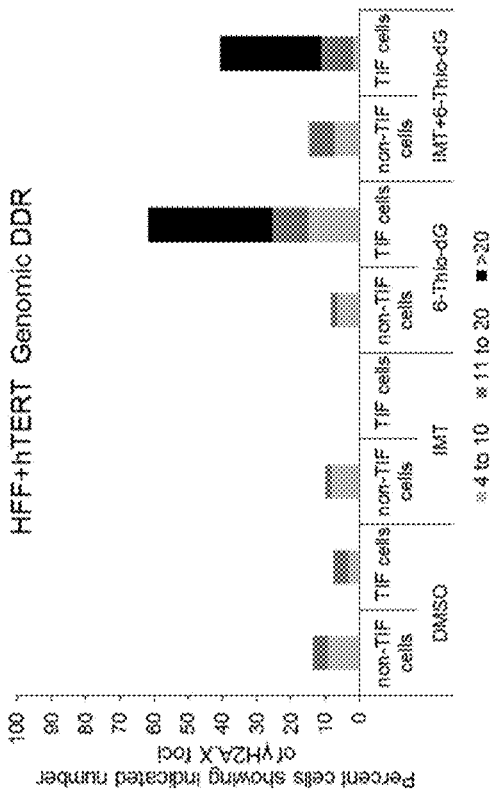
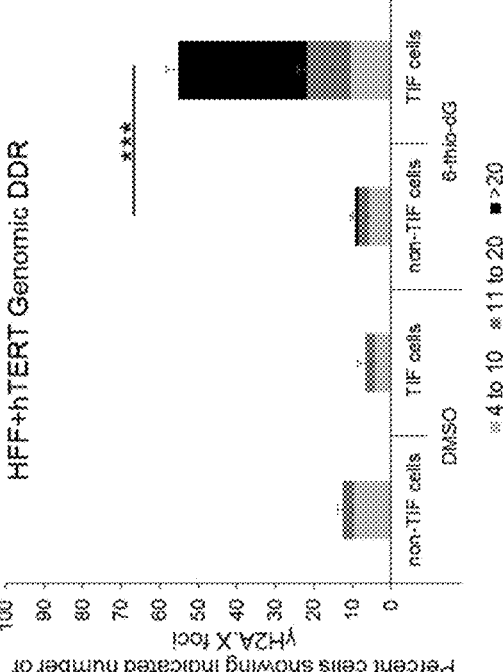
FIGS. 9A-B

A
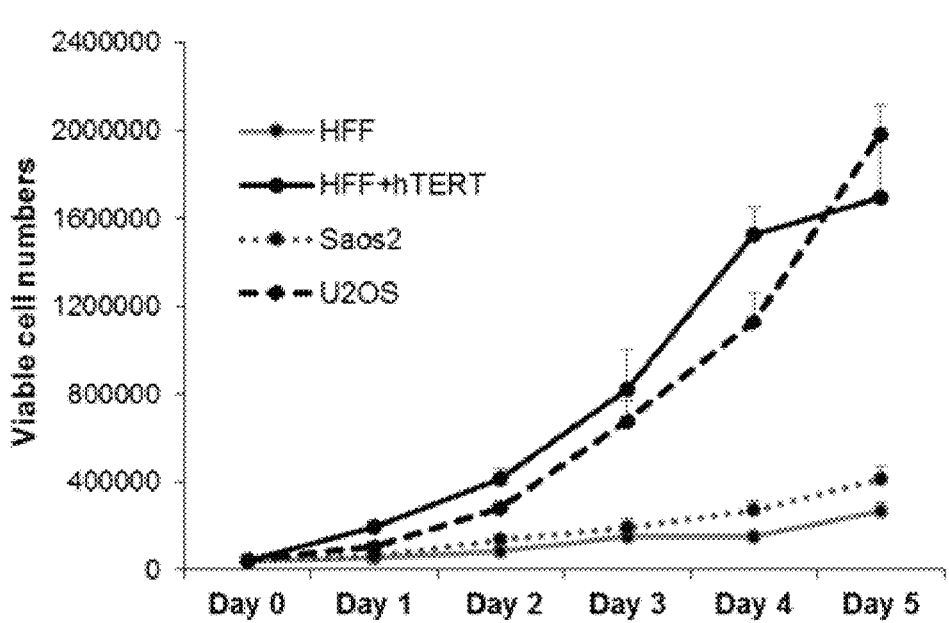
B
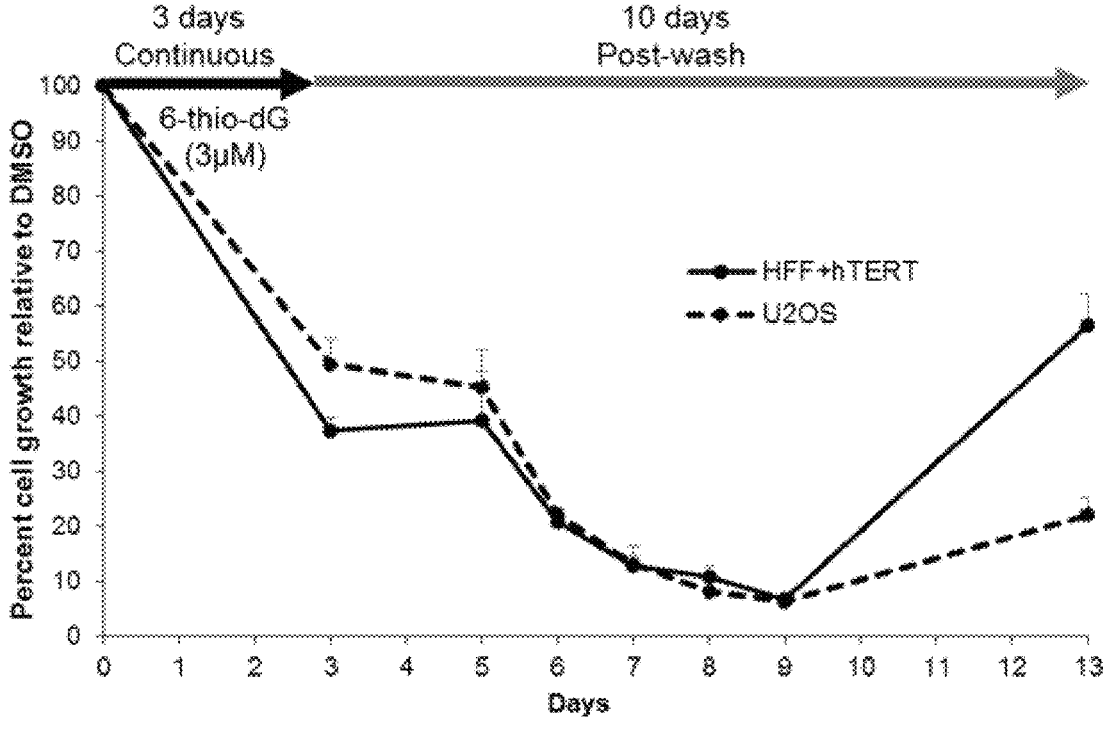
FIGS. 10A-B

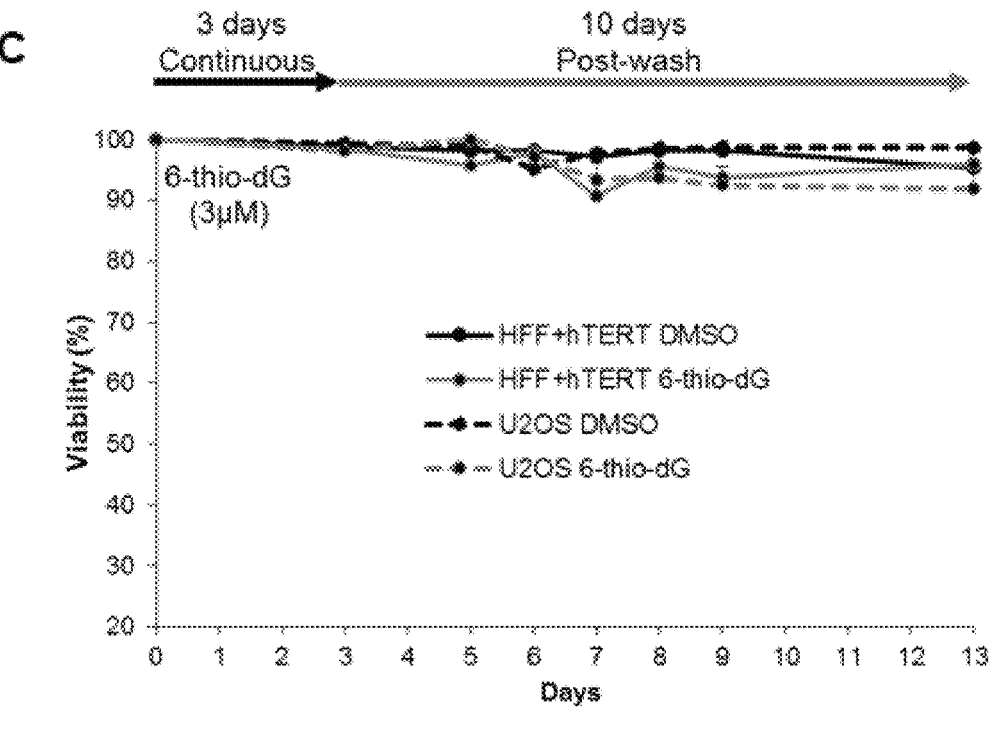
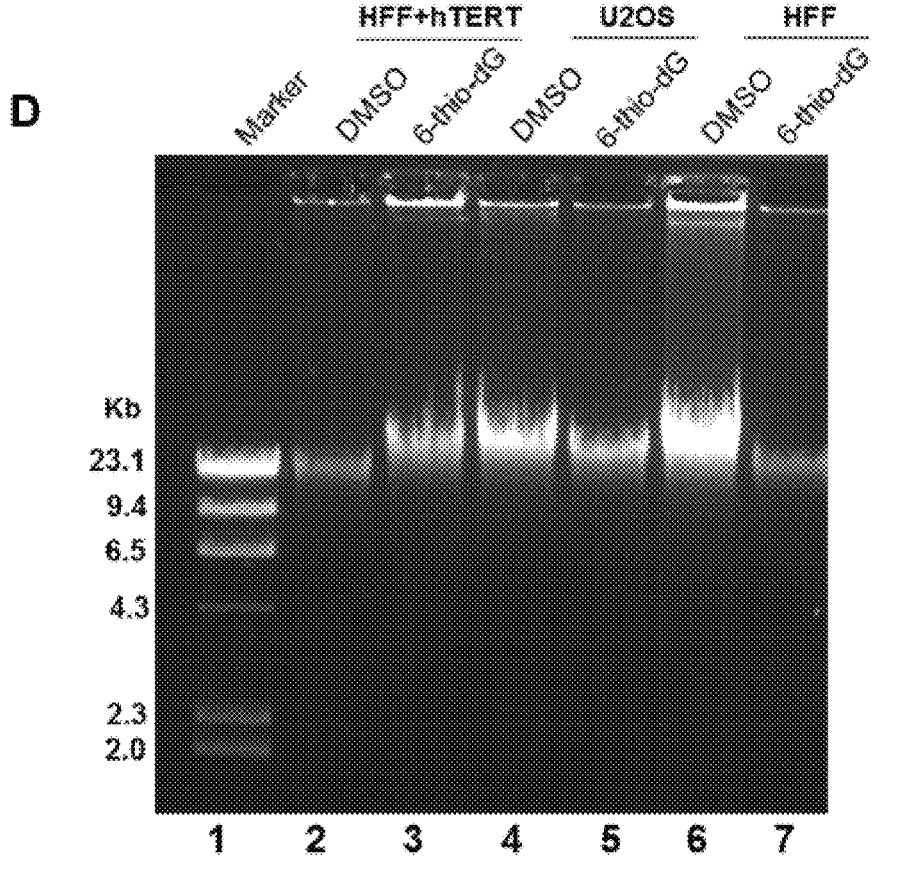
FIG. 10C-D

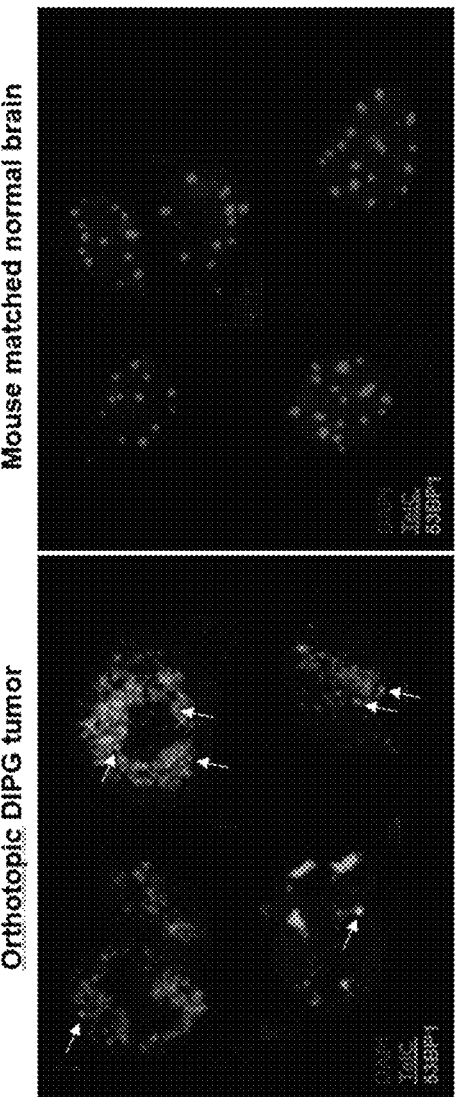
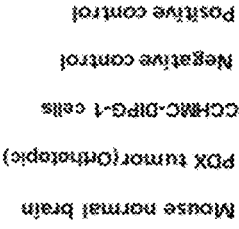
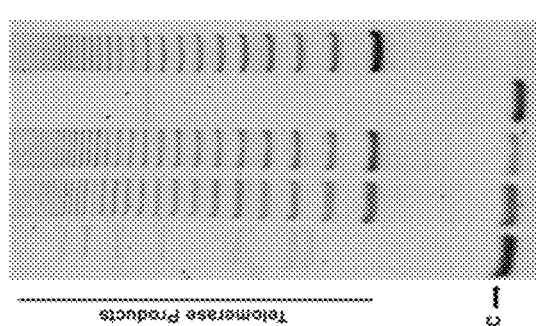
FIGS. 12A-B

SEQUENCE LISTING

```
Sequence total quantity: 1
SEQ ID NO: 1          moltype = DNA  length = 18
FEATURE               Location/Qualifiers
misc_feature          1..18
                      note = Synthetic oligonucleotide
source                1..18
```

-continued

```
                    mol_type = other DNA
                    organism = synthetic construct
SEQUENCE: 1
ccctaaccct aaccctaa                                          18
```

USE OF 6-THIO-dG TO TREAT THERAPY-RESISTANT TELOMERASEPOSITIVE PEDIATRIC BRAIN TUMORS

PRIORITY CLAIM

This application is continuation of U.S. application Ser. No. 16/928,979, filed Sep. 21, 2020, which is a national phase application under 35 U.S.C. § 371 of International Application No. PCT/US2019/023596, filed Mar. 22, 2019, which claims benefit of priority to U.S. Provisional Application Ser. No. 62/646,820, filed Mar. 22, 2018, the entire contents of each of which are hereby incorporated by reference.

SEQUENCE LISTING

This application contains a Sequence Listing XML, which has been submitted electronically and is hereby incorporated by reference in its entirety. Said XML Sequence Listing, created on Nov. 16, 2023, is named UTSDP3596USC1.xml and is 2,391 bytes in size.

BACKGROUND

1. Field

The present disclosure relates to the fields of medicine, pharmacology, molecular biology and oncology. More particular, the disclosure relates to methods and compositions for treating pediatric brain cancers, such as drug-resistant brain cancers.

2. Related Art

Telomeres are the physical ends of eukaryotic linear chromosomes and, in mammals, are composed of several kilobases of tandem TTAGGG repeats that are bound by the shelterin protein complex (1). Shelterin proteins protect telomeres from ATM and ATR-dependent DNA damage responses (DDR) (1). The inventors and others have previously shown that natural telomere shortening during replicative senescence or experimental telomere uncapping elicit ATM-dependent DDR triggered by telomere dysfunction (2,3). The hallmark of telomere dysfunction is the formation of DNA damage foci localized at telomeres called TIFs (telomere dysfunction-induced foci). TIFs are focal accumulations of DDR factors such as ATM S1981-P, γH2AX, and 53BP1 at dysfunctional telomeres (4). Telomeres are maintained by telomerase activity in 73-90% of primary human cancers, while in most normal somatic cells this activity is not detectable (5-7). Human telomerase consists of two essential components, the protein catalytic subunit (hTERT) and the RNA template (hTERC) that contribute to the synthesis of telomeric repeats, thereby maintaining telomeres. Telomerase activation, a feature of the vast majority of cancers, is essential for maintaining an immortal phenotype by conferring unlimited replicative potential.

Brain tumors are the most common solid tumors of childhood and are the leading cause of cancer-related deaths in children (8). Diffuse intrinsic pontine glioma (DIPG) is a particularly poor prognosis brain tumor with a median overall survival of less than one year (9). Hence, there is an urgent need to develop novel therapies that not only improve outcome but mitigate long-term complications in children with these poor-prognosis brain tumors. The inventors have previously shown that over 73% of DIPG and 50% of high-grade gliomas (HGG) (10) demonstrate telomerase activity. The recently conducted molecular biology and phase II study of imetelstat, a potent inhibitor of telomerase (11,12), estimated inhibition of tumor telomerase activity and efficacy in children with recurrent central nervous system (CNS) malignancies (13). The regimen proved intolerable, because of thrombocytopenia that led to bleeding. This toxicity prevented more frequent dosing of imetelstat to allow sustained telomerase inhibition. Because targeting telomerase directly, such as with imetelstat, would result in a significant lag period from the initiation of treatment until telomeres shortened sufficiently to reduce tumor burden, stopping therapy with imetelstat would result in rapid telomere regrowth. Thus, new approaches utilizing this almost universal cancer target are needed.

SUMMARY

Thus, in accordance with the disclosure, there are provided methods of treating a brain cancer in a pediatric subject, comprising administering a telomerase substrate precursor analog to a subject in need thereof, thereby treating pediatric brain cancer. In some aspects, the subject's is age 1-21, 1-18 or 1-14. In some aspects, the pediatric brain cancer is drug resistant. In some aspects, the pediatric brain cancer is diffuse intrinsic pontine glioma (DIPG), high-grade glioma (HGG), or high-risk medulloblastoma (MB). In some aspects, the brain cancer has telomerase activity. In some aspects, the telomerase substrate precursor analog is 6-thio-2'deoxyguanosine (6-thio-dG). In certain aspects, 6-thio-dG induces in vivo telomere dysfunction-induced foci (TIFs), apoptosis, and an inhibition of tumor growth. In some aspects, the telomerase substrate precursor analog is administered in combination or sequentially with an immunotherapeutic agent, a targeted drug, an epigenetic modifier, a chemotherapeutic agent, radiotherapy, or any combination thereof. In some aspects, the telomerase substrate precursor analog is administered in combination with an immune checkpoint inhibitor, such as an anti-PD-L1 or PD-1 antibody. In some aspects, the methods further comprise the step of assessing telomerase activity in a brain cancer cell from said subject.

In another embodiment, provided herein are methods of inducting G$_2$/M cell cycle arrest in a cancer cell comprising contacting the cell with a telomerase substrate precursor analog and a telomerase inhibitor. In some aspects, the cancer cell is a brain cancer cell. In some aspects, the brain cancer cell is drug resistant. In some aspects, the brain cancer cell is diffuse intrinsic pontine glioma (DIPG), high-grade glioma (HGG), or high-risk medulloblastoma (MB). In some aspects, the cancer cell exhibits telomerase activity. In some aspects, the telomerase substrate precursor analog is 6-thio-2'deoxyguanosine (6-thio-dG). In some aspects, 6-thio-dG induces in vivo telomere dysfunction-induced foci (TIFs), apoptosis, and an inhibition of tumor growth. In some aspects, the telomerase substrate precursor analog is administered in combination or sequentially with an immunotherapeutic agent, a targeted drug, an epigenetic modifier, a chemotherapeutic agent, radiotherapy, or any combination thereof. In some aspects, the methods further comprise the step of assessing telomerase activity in said cancer cell. In some aspects, the cell cycle arrest induces the accumulation of genomic DNA damage.

Other objects, features and advantages of the present disclosure will become apparent from the following detailed description. It should be understood, however, that the detailed description and the specific examples, while indicating particular embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 1A, telomerase-positive cells: HeLa and HFF+hTERT; telomerase-negative cells: HFF, and Saos-2 (ALT-positive). FIG. 1B, telomerase-positive patient-derived pediatric brain tumor cells: MB004, R0315-GBM, SU-DIPGVI and CCHMC-DIPG-1. FIG. 1C, matched pair of patient-derived medulloblastoma cells at biopsy (D-425, Primary) and at post-therapy failure (D-458, Recurrence) treated with DMSO or 0.5-10 μM of 6-thio-dG for one week. Error bars represent the standard deviation from triplicates. Each experiment was performed at least twice.

FIG. 2A, cell cycle analysis of HFF, HFF+hTERT, and HeLa cells treated with DMSO or with 3 μM of 6-thiodG for 3 days. FIG. 2B, schematic of the experimental design of continuous and wash off treatment. FIG. 2C-2C-5, cell cycle plots of DMSO controls and 6-thio-dG treated HFF, HFF+hTERT, and HeLa cells at days 5, 6, 7, and 8. FIG. 2D-2D-3, cell cycle plots of pre-treated HFF+hTERT and HeLa with DMSO or 3 μM of 6-thio-dG for 3 days at day 1 to 5 post-drug removal. The percentage of cells in sub-$G_1$, $G_1$, S, $G_2$/M and >4n is indicated in each plot. The lower panels indicate the percent distribution of cell cycle phases as a function of time. The experiments were conducted at least twice and the results shown are representative of the replicates.

FIGS. 3A-D. 6-thio-dG causes sustained telomere damage in telomerase-positive cells. FIG. 3A, HFF and HFF+hTERT cells were cultured with 3 μM of 6-thio-dG for 2 days (initial treatment), then continuously for another 3 days (continuous treatment) or 3 days post-drug removal (drug wash off). The number of TIFs per cell was counted for each treatment (~100 cells per treatment). Bottom panels show representative images of FISH-immunofluorescence using a telomere specific PNA probe (red) and γH2AX staining (green). White Arrows indicate co-localization of γH2AX and telomere signals (yellow), indicative of TIFs. DAPI (blue) indicates nucleus staining. Average values of at least three fields per cell per condition were evaluated. P-values are indicated, , P<0.01; *, P<0.001. FIG. 3B, cell cycle plots of MB004 treated with DMSO or 3 μM of 6-thio-dG for 3 days. Percent events of cell cycle phases are indicated. FIG. 3C, cell images of neurosphere formation assay at day 3 and day 7 post-treatment with DMSO or 3 μM of 6-thio-dG. Right panel indicates the quantification of the number of spheres at day 3 and 7. Error bars represent the standard deviation generated from triplicates. FIG. 3D, relative growth of MB004 cells treated with 6-thio-dG to DMSO control. The cells were initially treated with 3 μM of 6-thio-dG for 2 days followed by 3 days of continuous or discontinuous treatment. Bottom panel shows representative IF-FISH images. Telomeres (red), γH2AX (green), and TIFs (yellow) are depicted. DAPI (blue) indicates nucleus staining. Error bars represent the standard deviation obtained from triplicates.

FIGS. 4A-C. Sequential activation of ATR and ATM in response to 6-thio-dG. FIG. 4A, Western blot analysis of ATR-T1989P, total ATR, ATM-S1981P, and total ATM in HFF, and HFF+hTERT cells at day 1, 2, and 3 post-treatment with 3 μM of 6-thio-dG. d, indicates day. β-actin served as a loading control. Irradiated HFF cells with 5 Gy were used as a positive control for ATM and ATR activation. Bar diagrams (bottom) show the quantification of ATR-T1989P, and ATM-S-1981P phosphorylation levels relative to the corresponding DMSO. O.D. (optical density) was measured by densitometry analysis using ImageJ software. Band intensities were normalized to total ATR or total ATM as applicable. Average values of two independent experiments were evaluated. FIG. 4B, quantification of IF-FISH data in HFF+hTERT cells treated or untreated (DMSO) with 3 μM of 6-thio-dG for 1 to 3 days. Representative images of cells (bottom panel) are shown with TIFs (yellow foci denoted by white arrows), telomeres (red), γH2A.X (green), and nucleus (DAPI in blue). FIG. 4C, immunoblot analyses of ATR-T1989P, ATR, ATM S1981-P, ATM, CHK2 T68-P, CHK2, CHK1 S345-P, and CHK1 in HFF+hTERT cells treated with 10 μM of ATM or 50 nM ATR specific inhibitors for 2 hours prior to and in combination with DMSO (control) or 3 μM of 6-thio-dG for 2 days. IF-FISH was performed to assess the number of TIFs in 200 to 300 cells (right). Error bars are the standard deviations of at least three fields per condition (50 or more cells per field). P-values are indicated, *, P<0.05; , P<0.01; *, P<0.001; ****, P<0.0001.

FIG. 5A, representative IF images of cleaved-caspase-3 (green) in HFF, HFF+hTERT, and HeLa cells treated with DMSO or 3 μM of 6-thio-dG for 4 days. DAPI (blue) indicates nucleus staining. FIG. 5B, corresponding immunoblot analysis of cleaved-caspase-3. β-actin was used as a loading control. FIG. 5C, senescence-associated β-gal assay. Senescent HFF cells (HFF-S) at 70 population doublings (PD 70) were used as positive control for senescence (replicative senescence). Senescent cells are stained in blue. X-gal (+) and (−), indicate X-gal was added or not respectively. Early passage HFF (negative control) and HFF+hTERT were treated with 3 μM of 6-thio-dG or DMSO for 23 days. The plot on the right represents the quantification of the number of cells SA-β-gal-positive (senescent). Error bars represent the standard deviation generated from triplicates. P-value is indicated, *, P<0.05. Each experiment was performed at least twice.

FIGS. 6A-G. 6-thio-dG treatment inhibits tumor growth in pediatric high-risk group 3 medulloblastoma and induces TIFs in diffuse intrinsic pontine glioma (DIPG) xenografts. FIG. 6A, Average weight of mice treated with DMSO-PBS (vehicle) or 6-thio-dG. MB004 tumor cells were injected subcutaneously in the mouse flank and intraperitoneally (IP) injected when tumor was established with DMSO-PBS (vehicle) or 2.5 mg/kg of 6-thio-dG every two days for the indicated period of time. The arrow indicates the time of the tumor establishment and the start of the treatment. Error bars represent the standard deviation from 6 mice per group. FIG. 6B, tumor growth kinetics. Each line denotes tumor growth per mouse. Blue and red lines indicate vehicle and 6-thio-dG treatments respectively. FIG. 6C, representative immunohistochemistry images indicating cleaved-caspase-3 staining (brown) in FFPE sections from MB004 tumors treated with vehicle or 6-thio-dG. The plot on the right shows percent in-tumor apoptotic cells (cleaved-caspase-3 positive). Each dot represents average percent of apoptotic cells per individual tumor per mouse. P-value is indicated, *, P<0.05. Circles in FIG. 6B and FIG. 6C correspond to the same tumors showing slower growth kinetics (FIG. 6B) and higher apoptosis (FIG. 6C). FIG. 6D, quantification of in-tumor mitotic bodies (left), and apoptotic bodies (right) from FFPE sections stained with H & E. Average values of at least three fields per mouse were evaluated. P-values are indicated, *, P<0.001. FIG. 6E, the number of in-tumor telomere damage (TIFs) were counted and expressed as percent of cells with TIFs. Vehicle, indicates tumor from mice treated with DMSO-PBS and 6-thio-dG, indicates tumor from mice treated with 6-thio-dG. Error bars were generated from standard deviation of at least three fields (50 cells or more per field) per mouse. P-value is indicated, *, P<0.001. On the right, representative images of TIFs analysis in 6-thio-dG and vehicle treated tumors. Telomeres are in red, 53BP1 (green), and DAPI (blue). White arrows indicate TIFs (yellow). FIG. 6F, diagrammatic workflow showing detection of CCHMC-DIPG-1 orthotopic xenograft by luminescence imaging followed by resection and histological staining with H & E and Ki67 of collected tumors and matched normal tissue. Tumor and normal tissues are indicated. Circles indicate the tumor location in the brain. FIG. 6G, representative images of tissue IF-TIF analysis in 6-thio-dG and vehicle treated tumor. White arrows indicate TIFs (yellow), telomeres (red), and 53BP1 (green). DAPI (blue). On the right, quantification of TIFs. Error bars were generated from standard deviation of at least three fields (50 cells or more per field) counted per mouse. Significance between vehicle and 6-thio-dG treated tumors is indicated by P-value, **, P<0.01.

FIGS. 8A-D. FIG. 8A, Telomerase activity in HFF+hTERT cells treated with DMSO, 6-thio-dG (3 μM for 3 days), and imetelstat (IMT; 2 μM). For combination treatment, cells were pre-treated with IMT for 3 days and then with 6-thio-dG for another 3 days. (−) C, (+) C, and IC indicate negative control, positive control, and internal control, respectively. Telomerase products are indicated. FIGS. 8B-C, effect of telomerase inhibition on cell growth of HFF (B) and HFF+hTERT (C) cells treated with Imetelstat (IMT; 2 μM) only, 6-thio-dG (3 μM) only, or 6-thio-dG in combination with Imetelstat as described in A. Error bars represent the standard deviation generated from triplicates. P-value, **, P<0.01. FIG. 8D, quantifications showing percent cells with TIFs n FF+hTERT cells treated with Imetelstat (IMT; 2 μM) only, 6-thio-dG (3 μM for 3 days), or in combination with Imetelstat as described in FIG. S2A. Cells counted for each treatment (n=~ 50 cells). Bottom panels show representative images showing TRF2 (green), γH2AX (red), and TIFs (yellow) indicated by white arrows. DAPI (blue) indicates nucleus staining.

FIGS. 9A-B. FIG. 9A, quantification of genomic damage (γH2AX foci) in TIFs-negative (non-TIF) and TIFs-positive (TIF) HFF+hTERT cells treated or untreated (DMSO) with 3 mM of 6-thio-dG for 3 days. Error bars represent the standard deviation from three independent experiments.

P-value is indicated, ***<0.001. FIG. 9B, quantification of γH2AX foci in non-TIF and TIFs-positive HFF+hTERT cells treated with DMSO, Imetelstat (IMT; 2 μM), 6-thio-dG (3 μM for 3 days), or in combination as described in FIG. S2A.

FIGS. 10A-D. FIG. 10A, cell growth kinetics of HFF, HFF+hTERT, Saos-2, and U2OS cells. FIG. 10B, relative cell growth. FIG. 10C, percent viability of HFF+hTERT and U2OS cells treated with 3 mM 6-thio-dG for 3 days followed by 10-days post-drug removal. FIG. 10D, agarose gel electrophoresis (0.7%) of genomic DNA extracted from HFF+hTERT (lanes 2,3), U2OS (lanes 4,5), and HFF (lanes 6,7) cells treated with DMSO or 3 μM 6-thio-dG treated for 3 days. Lane 1, molecular weight marker, lambda phage DNA/HindIII, is indicated. Gel was run two independent times.

FIGS. 12A-B. FIG. 12A, Telomerase activity in mouse normal brain, orthotopic PDXDIPG tumor, and patient-derived DIPG-1cells (CCHMC-DIPG-1), along with negative and positive controls for TRAP assay. IC, indicates internal control. Telomerase products are indicated. FIG. 12B, Telomere FISH-IF images of orthotopic DIPG tumor (PDX) and the matched normal mouse brain. TIFs (yellow) are indicated by white arrows, telomeres (TelC; red) and 53BP1 (green). DAPI (blue) indicates nucleus staining. The two images are from the brain of the same mouse. Of note, mouse telomeres are longer than human, hence the strong telomere signals (in red) in mouse brain relative to human DIPG tumor.

DETAILED DESCRIPTION

Figure 1A:
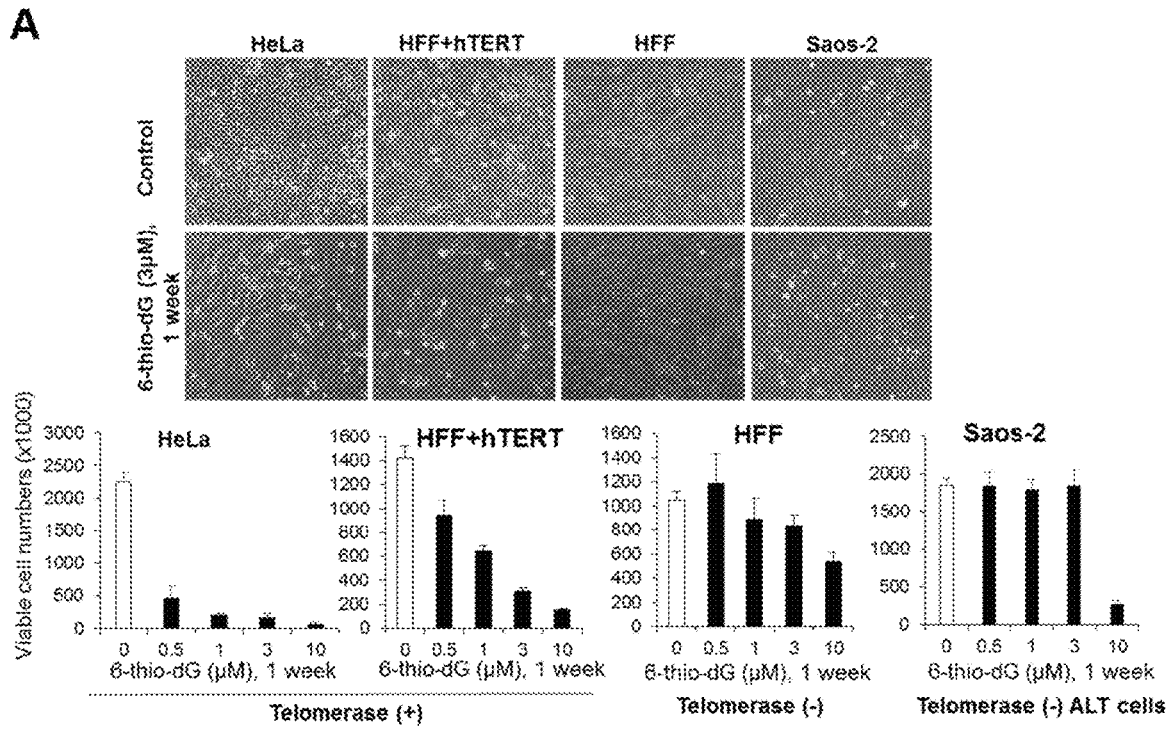
FIGS. 1A-C. 6-thio-dG specifically inhibits cell growth of telomerase-positive cells. Cell images (upper panel) and corresponding viable cell counts (lower panel).

As discussed above, current approaches to treating pediatric brain cancer that involve shortening of telomeres has proven problematic. Given the role played by telomerase reactivation in oncogenesis, telomeres and telomerase remain relevant therapeutic targets in this patient population (14-16). Recently, preclinical studies validated a telomere targeting strategy consisting of the incorporation of 6-thio-2'-deoxyguanosine (6-thio-dG), a telomerase substrate precursor nucleoside analog, into telomeres by telomerase (17). Mender et al. have shown that telomerase-dependent incorporation of 6-thiodG into telomeres is very effective and specific at targeting telomerase-positive cancer cells but not telomerase silent normal cells (17). Treatment with 6-thio-dG led to telomere damage and cell death in telomerase-positive cancer cell lines. Since this effect appears to be telomere-length independent, the prediction using this novel approach is that treatment with 6-thio-dG will require a shorter time period to achieve a rapid effect on tumor growth and progression than direct telomerase inhibition-based therapy (18). This approach could be beneficial for patients with aggressive brain tumors such as DIPG. In the present study, the inventors tested the in vitro and in vivo effect of 6-thio-dG in telomerase-positive stem-like cells derived from poor-prognosis pediatric brain tumors and addressed the mechanistic aspect of 6-thio-dG-induced DNA damage response in telomerase-positive cancer and normal cells. These findings suggest that 6-thio-dG is a promising novel approach to treat therapy-resistant pediatric brain tumors and provide a rationale for clinical testing of 6-thio-dG in children with brain tumors.

These and other aspects of the disclosure are described in detail below.

I. Telomeres, Telomerase and Telomere Dysfunction

During mitosis, cells make copies of their genetic material. Half of the genetic material goes to each new daughter cell. To make sure that information is successfully passed from one generation to the next, each chromosome has a special protective cap called a telomere located at the end of its "arms." Telomeres are controlled by the presence of the enzyme telomerase.

A telomere is a repeating DNA sequence (for example, TTAGGG) at the end of the body's chromosomes. The telomere can reach a length of 15,000 base pairs. Telomeres function by preventing chromosomes from losing base pair sequences at their ends. They also stop chromosomes from fusing to each other. However, each time a cell divides, some of the telomere is lost (usually 25-200 base pairs per division). When the telomere becomes too short, the chromosome reaches a "critical length" and can no longer replicate. This means that a cell becomes old and dies by a process called apoptosis or undergoes senescence. Telomere activity is controlled by two mechanisms: erosion and addition. Erosion, as mentioned, occurs each time a cell divides due to the failure of lagging strand DNA synthesis to be completed all the way to the end. Addition is determined by the activity of telomerase.

Telomerase, also called telomere terminal transferase, is an enzyme made of protein and RNA subunits that elongates chromosomes by adding TTAGGG sequences to the end of existing chromosomes. Telomerase is found in fetal tissues, adult germ cells, and also tumor cells. Telomerase activity is regulated during development and has a very low, almost undetectable activity in somatic (body) cells. Because these somatic cells do not regularly use telomerase, they age. The result of aging cells is an aging body. If telomerase is activated in a cell, the cell will continue to grow and divide. This "immortal cell" theory is important in two areas of research: aging and cancer.

Cellular aging, or senescence, is the process by which a cell becomes old and stops growing or dies. It is due to the shortening of chromosomal telomeres to the point that the chromosome reaches a critical length. Cellular aging is analogous to a wind-up clock. If the clock stays wound, a cell becomes immortal and constantly produces new cells. If the clock winds down, the cell stops producing new cells and undergoes what is termed replicative senescence or dies. Cells are constantly aging. Being able to make the body's cells extend their replication ability certainly creates some exciting possibilities especially for disease associated with genetic inheritance of short telomeres (termed telomeropathies or telomere spectrum disorders). Telomerase research could therefore yield important discoveries related to the aging process.

Cancer cells have escaped the normal short telomere aging phenomenon and become malignant cells. The malignant cells multiply until they form a tumor that grows uncontrollably and spreads to distant tissue throughout the human body. Telomerase has been detected in almost all human cancer cells. This provides a selective growth advantage to many types of tumors. If telomerase activity was to be turned off, then telomeres in cancer cells would progressively shorten, just like they do in normal body cells. This would prevent the cancer cells from dividing uncontrollably in their early stages of development. In the event that a tumor has already thoroughly developed, it may be removed and anti-telomerase therapy could be administered to prevent relapse. In essence, preventing telomerase from performing its function would change cancer cells from immortal to mortal. However, direct telomerase inhibitors require a lag period from initiation of treatment until tumor shrinkage occurs and have not progressed well in clinical development due to increased toxicities. Thus, the present invention provides methods to reduce the lag period but require telomerase activity to be effective and potentially reduce side effects.

II. Treating Brain Cancer

In accordance with the present disclosure, 6-thio-dG can be employed to treat a variety of cancer types. In general, brain, melanomas, lung cancers, pancreatic cancers and ovarian cancers. However, more generally, tumors expressing telomerase, including those having TERT promoter mutations and enriched telomere transcription signatures (e.g., a telomere maintenance signature and/or a packaging of telomere ends signature). Moreover, a variety of therapy-resistant cancers are responsive to 6-thio-dG therapy.

A. Brain Cancer

In particular, the present disclosure focuses on brain cancers, more particularly pediatric brain cancer, and in particular drug-resistant pediatric brain cancers. In the United States more than 28,000 people under 20 are estimated to have a brain tumor. About 3,720 new cases of brain tumors are expected to be diagnosed in those under 15 in 2019. Higher rates were reported in 1985-1994 than in 1975-1983. There is some debate as to the reasons; one theory is that the trend is the result of improved diagnosis and reporting, since the jump occurred at the same time that MRIs became available widely, and there was no coincident jump in mortality.

The average survival rate for all primary brain cancers in children is 74%. Brain cancers are the most common cancer in children under 19, and result in more death in this group than leukemia. Younger people do less well. The most common brain tumor types in children (0-14) are: pilocytic astrocytoma, malignant glioma, medulloblastoma, neuronal and mixed neuronal-glial tumors, and ependymoma.

In children under 2, about 70% of brain tumors are medulloblastomas, ependymomas, and low-grade gliomas. Less commonly, and seen usually in infants, are teratomas and atypical teratoid rhabdoid tumors. Germ cell tumors, including teratomas, make up just 3% of pediatric primary brain tumors, but the worldwide incidence varies significantly.

A brain tumor occurs when abnormal cells form within the brain. There are two main types of tumors: malignant or cancerous tumors and benign tumors. Cancerous tumors can be divided into primary tumors, which start within the brain, and secondary tumors, which have spread from elsewhere, known as brain metastasis tumors. All types of brain tumors may produce symptoms that vary depending on the part of the brain involved. These symptoms may include headaches, seizures, problems with vision, vomiting and mental changes. The headache is classically worse in the morning and goes away with vomiting. Other symptoms may include difficulty walking, speaking or with sensations. As the disease progresses, unconsciousness may occur.

The cause of most brain tumors is unknown. Uncommon risk factors include inherited neurofibromatosis, exposure to vinyl chloride, Epstein-Barr virus and ionizing radiation. The evidence for mobile phone exposure is not clear. The most common types of primary tumors in adults are meningiomas (usually benign) and astrocytomas such as glioblastomas. In children, the most common type is a malignant medulloblastoma. Diagnosis is usually by medical examination along with computed tomography or magnetic resonance imaging. The result is then often confirmed by a biopsy. Based on the findings, the tumors are divided into different grades of severity.

Treatment may include some combination of surgery, radiation therapy and chemotherapy. Anticonvulsant medication may be needed if seizures occur. Dexamethasone and furosemide may be used to decrease swelling around the tumor. Some tumors grow gradually, requiring only monitoring and possibly needing no further intervention. Treatments that use a person's immune system are being studied. Outcome varies considerably depending on the type of tumor and how far it has spread at diagnosis. Glioblastomas usually have poor outcomes, while meningiomas usually have good outcomes. The average five-year survival rate for all brain cancers in the United States is 33%.

Secondary, or metastatic, brain tumors are more common than primary brain tumors, with about half of metastases coming from lung cancer. Primary brain tumors occur in around 250,000 people a year globally, making up less than 2% of cancers. In children younger than 15, brain tumors are second only to acute lymphoblastic leukemia as the most common form of cancer. In Australia, the average lifetime economic cost of a case of brain cancer is $1.9 million, the greatest of any type of cancer.

The brain is divided into four lobes and each lobe or area has its own function. A tumor in any of these lobes may affect the area's performance. The location of the tumor is often linked to the symptoms experienced but each person may experience something different.

Frontal lobe tumors may contribute to poor reasoning, inappropriate social behavior, personality changes, poor planning, lower inhibition, and decreased production of speech (Broca's area).

Temporal lobe tumors may contribute to poor memory, loss of hearing, difficulty in language comprehension (Wernicke's area).

Parietal lobe tumors may result in poor interpretation of languages and difficulty speaking, difficulty writing, drawing, naming, and recognizing, and poor spatial and visual perception.

Occipital lobe tumors may result in poor or loss of vision.

Cerebellum tumors may cause poor balance, muscle movement, and posture.

Brain stem tumors can cause seizures, induce endocrine problems, respiratory changes, visual changes, headaches and partial paralysis.

Human brains are surrounded by a system of connective tissue membranes called meninges that separate the brain from the skull. This three-layered covering is composed of (from the outside in) the dura mater ("hard mother"), arachnoid mater ("spidery mother"), and pia mater ("tender mother"). The arachnoid and pia are physically connected and thus often considered as a single layer, the pia-arachnoid, or leptomeninges. Between the arachnoid mater and the pia mater is the subarachnoid space which contains cerebrospinal fluid (CSF). This fluid circulates in the narrow spaces between cells and through the cavities in the brain called ventricles, to nourish, support, and protect the brain tissue. Blood vessels enter the central nervous system through the perivascular space above the pia mater. The cells in the blood vessel walls are joined tightly, forming the blood-brain barrier which protects the brain from toxins that might enter through the blood. Tumors of the meninges are meningiomas and are often benign.

The brains of humans and other vertebrates are composed of very soft tissue and have a gelatin-like texture. Living brain tissue has a pink tint in color on the outside (gray matter), and nearly complete white on the inside (white matter), with subtle variations in color. Three separate brain areas make up most of the brain's volume:

telencephalon (cerebral hemispheres or cerebrum)

mesencephalon (midbrain)

cerebellum

These areas are composed of two broad classes of cells: neurons and glia. These two types are equally numerous in the brain as a whole, although glial cells outnumber neurons roughly 4 to 1 in the cerebral cortex. Glia come in several types, which perform a number of critical functions, including structural support, metabolic support, insulation, and guidance of development. Primary tumors of the glial cells are called gliomas and often are malignant by the time they are diagnosed.

The pons in the brainstem is a specific region that consists of myelinated axons much like the spinal cord. The thalamus and hypothalamus of the diencephalon also consist of neuron and glial cell tissue with the hypophysis (pituitary gland) and pineal gland (which is glandular tissue) attached at the bottom; tumors of the pituitary and pineal gland are often benign. The medulla oblongata is at the start of the spinal cord and is composed mainly of neuron tissue enveloped in oligodendrocytes and meninges tissue. The spinal cord is made up of bundles of these axons. Glial cells such as Schwann cells in the periphery or, within the cord itself, oligodendrocytes, wrap themselves around the axon, thus promoting faster transmission of electrical signals and also providing for general maintenance of the environment surrounding the cord, in part by shuttling different compounds around in response to injury or other stimulus.

Although there is no specific or singular symptom or sign, the presence of a combination of symptoms and the lack of corresponding indications of other causes can be an indicator for investigation towards the possibility of an brain tumor. Brain tumors have similar characteristics and obstacles when it comes to diagnosis and therapy with tumors located elsewhere in the body. However, they create specific issues that follow closely to the properties of the organ they are in.

The diagnosis will often start by taking a medical history noting medical antecedents, and current symptoms. Clinical and laboratory investigations will serve to exclude infections as the cause of the symptoms. Examinations in this stage may include the eyes, otolaryngological (or ENT) and electrophysiological exams. The use of electroencephalography (EEG) often plays a role in the diagnosis of brain tumors.

Brain tumors, when compared to tumors in other areas of the body, pose a challenge for diagnosis. Commonly, radioactive tracers are uptaken in large volumes in tumors due to the high activity of tumor cells, allowing for radioactive imaging of the tumor. However, most of the brain is separated from the blood by the blood-brain barrier (BBB), a membrane which exerts a strict control over what substances are allowed to pass into the brain. Therefore, many tracers that may reach tumors in other areas of the body easily would be unable to reach brain tumors until there was a disruption of the BBB by the tumor. Disruption of the BBB is well imaged via MRI or CT scan, and is therefore regarded as the main diagnostic indicator for malignant gliomas, meningiomas, and brain metastases.

Swelling or obstruction of the passage of cerebrospinal fluid (CSF) from the brain may cause (early) signs of increased intracranial pressure which translates clinically into headaches, vomiting, or an altered state of consciousness, and in children changes to the diameter of the skull and bulging of the fontanelles. More complex symptoms such as endocrine dysfunctions should alarm doctors not to exclude brain tumors.

A bilateral temporal visual field defect (due to compression of the optic chiasm) or dilation of the pupil, and the occurrence of either slowly evolving or the sudden onset of focal neurologic symptoms, such as cognitive and behavioral impairment (including impaired judgment, memory loss, lack of recognition, spatial orientation disorders), personality or emotional changes, hemiparesis, hypoesthesia, aphasia, ataxia, visual field impairment, impaired sense of smell, impaired hearing, facial paralysis, double vision, or more severe symptoms such as tremors, paralysis on one side of the body hemiplegia, or (epileptic) seizures in a patient with a negative history for epilepsy, should raise the possibility of a brain tumor.

Tumors can be benign or malignant, can occur in different parts of the brain, and may be primary or secondary. A primary tumor is one that has started in the brain, as opposed to a metastatic tumor, which is something that has spread to the brain from another part of the body. The incidence of metastatic tumors are more prevalent than primary tumors by 4:1. Tumors may or may not be symptomatic: some tumors are discovered because the patient has symptoms, others show up incidentally on an imaging scan, or at an autopsy.

The Most Common Primary Brain Tumors are:
   Gliomas (50.4%)
   Meningiomas (20.8%)
   Pituitary adenomas (15%)
   Nerve sheath tumors (8%)
Other types include Anaplastic astrocytoma, Astrocytoma, Central neurocytoma, Choroid plexus carcinoma, Choroid plexus papilloma, Choroid plexus tumor, Dysembryoplastic neuroepithelial tumour, Ependymal tumor, Fibrillary astrocytoma, Giant-cell glioblastoma, Glioblastoma multiforme, Gliomatosis cerebri, Gliosarcoma, Hemangiopericytoma, Medulloblastoma, Medulloepithelioma, Meningeal carcinomatosis, Neuroblastoma, Neurocytoma, Oligoastrocytoma, Oligodendroglioma, Optic nerve sheath meningioma, Pediatric ependymoma, Pilocytic astrocytoma, Pineoblastoma, Pineocytoma, Pleomorphic anaplastic neuroblastoma, Pleomorphic xanthoastrocytoma, Primary central nervous system lymphoma, Sphenoid wing meningioma, Subependymal giant cell astrocytoma, Subependymoma, Trilateral retinoblastoma.

A medical team generally assesses the treatment options and presented to the person affect and their family. Various types of treatment are available depending on neoplasm type and location and may be combined to give the best chances of survival (discussed in greater detail in Section IV on Combination Therapies):
   Surgery: complete or partial resection of the tumor with the objective of removing as many tumor cells as possible.
   Radiotherapy: the most commonly used treatment for brain tumors; the tumor is irradiated with beta, x rays or gamma rays.
   Chemotherapy: is a treatment option for cancer, however, it is not always used to treat brain tumors as the blood-brain barrier can prevent some drugs from reaching the cancerous cells.

A variety of experimental therapies are available through clinical trials. Survival rates in primary brain tumors depend on the type of tumor, age, functional status of the patient, the extent of surgical tumor removal and other factors specific to each case.

B. Telomerase Positive Cancers

Telomerase-positive cancers are far more susceptible to the methods of the present disclosure than are telomerase-negative cancers. Therefore, testing a biopsy to determine whether the cancer is or is not telomerase-positive is highly useful.

The most common methods for detecting telomerase activity are telomeric repeat amplification protocols (TRAPs), which allow one to perform semi-quantitative and quantitative analyses, using some of their modifications (called ddTRAP for droplet digital TRAP). Among these modifications are the scintillation proximity assay, hybridization protection assay, transcription amplification assay, and the magnetic bead-based extraction assay.

The telomeric repeat amplification protocol can be subdivided into three main stages: primer elongation, amplification of telomerase-synthesized DNA, and finally its detection. At the elongation stage, telomeric repeats are added to the telomere-imitating oligonucleotide by telomerase present in the cell extract. PCR-amplification of telomerase-synthesized DNA is carried out with telomere-imitating and reverse primers. Different labels can be incorporated into the telomerase-synthesized DNA. This stage is then followed by detection (e.g., electrophoretic separation and imaging of PCR products).

Still other methods involve the quantitative isolation of telomerase, and the subsequent measurement of the overall activity of the telomerase from a given cell quantity, which can be compared to appropriate standards. A wide variety of labeling and detection methodologies can be employed once telomerase has been isolated and tested in vitro.

C. Drug Resistant Cancers

Antineoplastic resistance, often used interchangeably with chemotherapy resistance, is the resistance of neoplastic (cancerous) cells, or the ability of cancer cells to survive and grow despite anti-cancer therapies. In some cases, cancers can evolve resistance to multiple drugs, called multiple drug resistance.

There are two general causes of antineoplastic therapy failure: Inherent genetic characteristics, giving cancer cells their resistance and acquired resistance after drug exposure, which is rooted in the concept of cancer cell heterogeneity. Characteristics of resistant cells include altered membrane transport, enhanced DNA repair, apoptotic pathway defects, alteration of target molecules, protein and pathway mechanisms, such as enzymatic deactivation. Since cancer is a genetic disease, two genomic events underlie acquired drug resistance: Genome alterations (e.g., gene amplification and deletion) and epigenetic modifications. Cancer cells are constantly using a variety of tools, involving genes, proteins, and altered pathways, to ensure their survival against antineoplastic drugs.

Antineoplastic resistance, synonymous with chemotherapy resistance, is the ability of cancer cells to survive and grow despite different anti-cancer therapies, i.e. their multiple drug resistance. There are two general causes of antineoplastic therapy failure: (i) inherent resistance, such as genetic characteristics, giving cancer cells their resistance from the beginning, which is rooted in the concept of cancer cell heterogeneity; and (ii) acquired resistance after drug exposure.

Since cancer is a genetic disease, two genomic events underlie these mechanisms of acquired drug resistance: Genome alterations (e.g., gene amplification and deletion) and epigenetic modifications.

Chromosomal rearrangement due to genome instability can cause gene amplification and deletion. Gene amplification is the increase in copy number of a region of a chromosome. which occur frequently in solid tumors, and can contribute to tumor evolution through altered gene expression.

Hamster cell research in 1993 showed that amplifications in the DHFR gene involved in DNA synthesis began with chromosome break in below the gene, and subsequent cycles of bridge-breakage-fusion formations result in large intrachromosomal repeats. The over amplification of oncogenes can occur in response to chemotherapy, thought to be the underlying mechanism in several classes of resistance. For example, DHFR amplification occurs in response to methotrexate, TYMS (involved in DNA synthesis) amplification occurs in response to 5-fluorouracil, and BCR-ABL amplification occurs in response to imatinib mesylate. Determining areas of gene amplification in cells from cancer patients has huge clinical implications. Gene deletion is the opposite of gene amplification, where a region of a chromosome is lost and drug resistance occurs by losing tumor suppressor genes such as TP53.

Genomic instability can occur when the replication fork is disturbed or stalled in its migration. This can occur with replication fork barriers, proteins such as PTIP, CHD4 and PARP1, which are normally cleared by the cell's DNA damage sensors, surveyors, and responders BRCA1 and BRCA2.

Epigenetic modifications in antineoplastic drug resistance play a major role in cancer development and drug resistance as they contribute to the regulation of gene expression. Two main types of epigenetic control are DNA methylation and histone methylation/acetylation. DNA methylation is the process of adding methyl groups to DNA, usually in the upstream promoter regions, which stops DNA transcription at the region and effectively silences individual genes. Histone modifications, such as deacetylation, alters chromatin formation and silence large chromosomal regions. In cancer cells, where normal regulation of gene expression breaks down, the oncogenes are activated via hypomethylation and tumor suppressors are silenced via hypermethylation. Similarly, in drug resistance development, it has been suggested that epigenetic modifications can result in the activation and overexpression of pro-drug resistance genes.

Studies on cancer cell lines have shown that hypomethylation (loss of methylation) of the MDR1 gene promoter caused overexpression and the multidrug resistance.

In a methotrexate resistant breast cancer cell lines without drug uptake and folate carrier expression, giving DAC, a DNA methylation inhibitor, improved drug uptake and folate carrier expression.

Acquired resistance to the alkylating drug fotemustine in melanoma cell showed high MGMT activity related to the hypermethylation of the MGMT gene exons.

In Imatinib resistant cell lines, silencing of the SOCS-3 gene via methylation has been shown to cause STAT3 protein activation, which caused uncontrolled proliferation.

Cancer cells can become resistant to multiple drugs by altered membrane transport, enhanced DNA repair, apoptotic pathway defects, alteration of target molecules, protein and pathway mechanisms, such as enzymatic deactivation.

Many classes of antineoplastic drugs act on intracellular components and pathways, like DNA, nuclear components, meaning that they need to enter the cancer cells. The p-glycoprotein (P-gp), or the multiple drug resistance protein, is a phosphorylated and glycosylated membrane transporter that can shuttle drugs out of the cell, thereby decreasing or ablating drug efficacy. This transporter protein is encoded by the MDR1 gene and is also called the ATP-binding cassette (ABC) protein. MDR1 has promiscuous substrate specificity, allowing it to transport many structurally diverse compounds across the cell membrane, mainly hydrophobic compounds. Studies have found that the MDR1 gene can be activated and overexpressed in response to pharmaceutical drugs, thus forming the basis for resistance to many drugs. Overexpression of the MDR1 gene in cancer cells is used to keep intracellular levels of antineoplastic drugs below cell-killing levels.

For example, the antibiotic rifampicin has been found to induce MDR1 expression. Experiments in different drug resistant cell lines and patient DNA revealed gene rearrangements which had initiated the activation or overexpression of MDR1. A C3435T polymorphism in exon 226 of MDR1 has also been strongly correlated with p-glycoprotein activities.

MDR1 is activated through NF-κB, a protein complex which acts as a transcription factor. In the rat, an NF-κB binding site is adjacent to the mdr1b gene, NF-κB can be active in tumour cells because its mutated NF-κB gene or its inhibitory IκB gene mutated under chemotherapy. In colorectal cancer cells, inhibition of NF-κB or MDR1 caused increased apoptosis in response to a chemotherapeutic agent.

Enhanced DNA repair plays an important role in the ability for cancer cells to overcome drug-induced DNA damages.

Platinum-based chemotherapies, such as cisplatin, target tumor cells by cross-linking their DNA strands, causing mutation and damage. Such damage will trigger programmed cell death (e.g., apoptosis) in cancer cells. Cisplatin resistance occurs when cancer cells develop an enhanced ability to reverse such damage by removing the cisplatin from DNA and repairing any damage done. The cisplatin-resistant cells upregulate expression of the excision repair cross-complementing (ERCC1) gene and protein.

Some chemotherapies are alkylating agents meaning they attach an alkyl group to DNA to stop it from being read. 06-methylguanine DNA methyltransferase (MGMT) is a DNA repair enzyme which removes alkyl groups from DNA. MGMT expression is upregulated in many cancer cells, which protects them from alkylating agents. Increased MGMT expression has been found in colon cancer, lung cancer, non-Hodgkin's lymphoma, breast cancer, gliomas, myeloma and pancreatic cancer.

TP53 is a tumor suppressor gene encoding the p53 protein, which responds to DNA damage either by DNA repair, cell cycle arrest, or apoptosis. Losing TP53 via gene deletion can allow cells to continuously replicate despite DNA damage. The tolerance of DNA damage can grant cancer cells a method of resistance to those drugs which normally induce apoptosis through DNA damage.

Other genes involved in the apoptotic pathway related drug resistance include h-ras and bcl-2/bax. Oncogenic h-ras has been found to increase expression of ERCC1, resulting in enhanced DNA repair (see above). Inhibition of h-ras was found to increase cisplatin sensitivity in glioblastoma cells. Upregulated expression of Bcl-2 in leukemic cells (non-Hodgkin's lymphoma) resulted in decreased levels of apoptosis in response to chemotherapeutic agents, as Bcl-2 is a pro-survival oncogene.

During targeted therapy, oftentimes the target has modified itself and decreased its expression to the point that therapy is no longer effective. One example of this is the loss of estrogen receptor (ER) and progesterone receptor (PR) upon anti-estrogen treatment of breast cancer. Tumors with loss of ER and PR no longer respond to tamoxifen or other anti-estrogen treatments, and while cancer cells remain somewhat responsive to estrogen synthesis inhibitors, they eventually become unresponsive to endocrine manipulation and no longer dependent on estrogen for growth.

Another line of therapeutics used for treating breast cancer is targeting of kinases like human epidermal growth factor receptor 2 (HER2) from the EGFR family. Mutations often occur in the HER2 gene upon treatment with an inhibitor, with about 50% of patients with lung cancer found to have an EGFR-T790M gatekeeper mutation.

Treatment of chronic myeloid leukemia (CML) involves a tyrosine kinase inhibitor that targets the BCR/ABL fusion gene called imatinib. In some people resistant to Imatinib, the BCR/ABL gene is reactivated or amplified, or a single point mutation has occurred on the gene. These point mutations enhance autophosphorylation of the BCR-ABL protein, resulting in the stabilization of the ATP-binding site into its active form, which cannot be bound by imatinib for proper drug activation.

Topoisomerase is a lucrative target for cancer therapy due to its critical role as an enzyme in DNA replication, and many topoisomerase inhibitors have been made. Resistance can occur when topoisomerase levels are decreased, or when different isoforms of topoisomerase are differentially distributed within the cell. Mutant enzymes have also been reported in patient leukemic cells, as well as mutations in other cancers that confer resistance to topoisomerase inhibitors.

One of the mechanisms of antineoplastic resistance is over-expression of drug-metabolizing enzymes or carrier molecules. By increasing expression of metabolic enzymes, drugs are more rapidly converted to drug conjugates or inactive forms that can then be excreted. For example, increased expression of glutathione promotes drug resistance, as the electrophilic properties of glutathione allow it to react with cytotoxic agents, inactivating them. In some cases, decreased expression or loss of expression of drug-metabolizing enzymes confers resistance, as the enzymes are needed to process a drug from an inactive form to an active form. Arabinoside, a commonly used chemotherapy for leukemia and lymphomas, is converted into cytosine arabinoside triphosphate by deoxycytidine kinase. Mutation of deoxycytidine kinase or loss of expression results in resistance to arabinoside. This is a form of enzymatic deactivation.

Growth factor expression levels can also promote resistance to antineoplastic therapies. In breast cancer, drug resistant cells were found to express high levels of IL-6, while sensitive cells did not express significant levels of the growth factor. IL-6 activates the CCAAT enhancer-binding protein transcription factors which activate MDR1 gene expression.

III. PHARMACEUTICAL FORMULATIONS AND ROUTES OF ADMINISTRATION

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render drugs stable and allow for uptake by target cells. Aqueous compositions of the present disclosure comprise an effective amount of the drug dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present disclosure, its use in therapeutic compositions is contemplated. Supplementary active ingredients also can be incorporated into the compositions, provided they do not inactivate the agents of the compositions.

The active compositions of the present disclosure may include classic pharmaceutical preparations. Administration of these compositions according to the present disclosure may be via any common route so long as the target tissue is available via that route, but generally including systemic administration. This includes oral, nasal, or buccal. Alternatively, administration may be by intradermal, subcutaneous, intramuscular, intraperitoneal or intravenous injection, or intratumoral or regional to a tumor, such as in the tumor vasculature. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present disclosure generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of may prove effective, in particular, to combine 6-thio-dG with other therapies that target different aspects of cancer cell function (such as immune checkpoint inhibitors).

To kill cells, inhibit cell growth, inhibit metastasis, inhibit angiogenesis or otherwise reverse or reduce the malignant phenotype of tumor cells, using the methods and compositions of the present disclosure, one would generally contact a "target" cell with 6-thio-dG and at least one other agent. These compositions would be provided in a sequential or combined amount effective to kill or inhibit proliferation of the cell. This process may involve contacting the cells with 6-thio-dG and the other agent(s) or factor(s) at the same time. This may be achieved by contacting the cell with a single composition or pharmacological formulation that includes both agents, or by contacting the cell with two distinct compositions or formulations, at the same time, wherein one composition includes the interferon prodrugs according to the present disclosure and the other includes the other agent.

Alternatively, the 6-thio-dG therapy may precede or follow the other agent treatment by intervals ranging from minutes to weeks. In embodiments where the other agent and the interferon prodrugs are applied separately to the cell, one would generally ensure that a significant period of time did not expire between each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. For example, pretreating with 6-thio-dG then adding checkpoint inhibitors antibodies (e.g. PDL-1 and PD-1 inhibitors) may improve outcomes.

It also is conceivable that more than one administration of either interferon prodrugs or the other agent will be desired. Various combinations may be employed, where 6-thio-dG therapy is "A" and the other therapy is "B", as exemplified below:

| A/B/A | B/A/B | B/B/A | A/A/B | B/A/A | A/B/B | B/B/B/A | B/B/A/B |
| A/A/B/B | A/B/A/B | | A/B/B/A | B/B/A/A | B/A/B/A | B/A/A/B | B/B/B/A |
| A/A/A/B | B/A/A/A | | A/B/A/A | A/A/B/A | A/B/B/B | B/A/B/B | B/B/A/B |

Other combinations are contemplated. Again, to achieve cell killing, both agents are delivered to a cell in a combined amount effective to kill the cell.

Agents or factors suitable for cancer therapy include any chemical compound or treatment method that induces DNA damage when applied to a cell. Such agents and factors include radiation and waves that induce DNA damage such as, irradiation, microwaves, electronic emissions, and the like. A variety of chemical compounds, also described as "chemotherapeutic" or "genotoxic agents," may be used. This may be achieved by irradiating the localized tumor site; alternatively, the tumor cells may be contacted with the agent by administering to the subject a therapeutically effective amount of a pharmaceutical composition.

Various classes of chemotherapeutic agents are contemplated for use with the present disclosure. Imetelstat is isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

IV. Combined Therapy

In the context of the present disclosure, it also is contemplated 6-thio-dG could be used in conjunction with chemo- or radiotherapeutic intervention, or other treatments. It also discussed below. Other chemotherapeutics include selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene. The agents camptothecin, actinomycin-D, and mitomycin C are commonly used chemotherapeutic drugs. The disclosure also encompasses the use of a combination of one or more DNA damaging agents, whether radiation-based or actual compounds, such as the use of X-rays with cisplatin or the use of cisplatin with etoposide. The agent may be prepared and used as a combined therapeutic composition.

Heat shock protein 90 is a regulatory protein found in many eukaryotic cells. HSP90 inhibitors have been shown to be useful in the treatment of cancer. Such inhibitors include Geldanamycin, 17-(Allylamino)-17-demethoxygeldanamycin, PU-H71 and Rifabutin.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m² for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m² at 21-day intervals for doxorubicin, to 35-50 mg/m² for etoposide intravenously or double the intravenous dose orally. Microtubule inhibitors, such as taxanes, also are contemplated. These molecules are diterpenes produced by the plants of the genus *Taxus* and include paclitaxel and docetaxel.

Epidermal growth factor receptor inhibitors, such as Iressa, mTOR, the mammalian target of rapamycin (also known as FK506-binding protein 12-rapamycin associated protein 1 (FRAP1)), is a serine/threonine protein kinase that regulates cell growth, cell proliferation, cell motility, cell survival, protein synthesis, and transcription. Rapamycin and analogs thereof ("rapalogs") are therefore contemplated for use in cancer therapy in accordance with the present disclosure. Another EGFR inhibitor of particular utility here is Gefitinib.

Another possible therapy is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

In addition, it also is contemplated that immunotherapy, hormone therapy, toxin therapy and surgery can be used.

The skilled artisan is directed to "Remington's Pharmaceutical Sciences" 15th Edition, Chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

A. Telomerase Inhibitors

A variety of telomerase inhibitors are known in the art and include antisense oligonucleotides, RNAi, dominant-negative TERT and ribozymes.

One oligonucleotide drug that targets telomerase is Imetelstat (GRN163L). Imetelstat was shown to be active against both CD138-positive and CD138-negative cancer stem cells and eliminated the colony forming potential of both by five weeks. Similarly, it inhibited the in vitro clonogenic growth of CD138-negative Multiple Myeloma Cancer Stem Cells isolated from the bone marrow aspirates of patients with multiple myeloma. On Nov. 3, 2014, the FDA removed the full clinical hold on imetelstat and declared the company's clinical development plan as acceptable.

Two active Phase 2 trials for Imetelstat are scheduled for completion in 2019 and 2022, one for Myelofibrosis and the other for Myelodysplastic Syndrome. In October 2017, Imetelstat was granted Fast Track status by the FDA for certain patients in Myelodysplastic Syndrome. However, side-effects that cause patients to temporarily stop therapy with Imetelstat may results in rapid telomere re-elongation and reduce the efficacy of such treatments.

B. Specific Brain Cancer Therapies

Surgery, radiation therapy and chemotherapy, alone or together, are front line therapies for brain cancer. Each of these approaches is discussed below.

Surgery is the removal of the tumor and some surrounding healthy tissue during an operation. It is usually the first treatment used for a brain tumor and is often the only treatment needed for a low-grade brain tumor. Removing the tumor can improve neurological symptoms, provide tissue for diagnosis, help make other brain tumor treatments more effective, and, in many instances, improve the prognosis of a person with a brain tumor. There have been rapid advances in surgery for brain tumors, including the use of cortical mapping, enhanced imaging, and fluorescent dyes.

In addition to removing or reducing the size of the brain tumor, surgery can provide a tissue sample for biopsy analysis. For some tumor types, the results of this analysis can help determine if chemotherapy or radiation therapy will be useful. For a cancerous tumor, even if it cannot be cured, removing it can relieve symptoms from the tumor pressing on the brain.

Radiation therapy is the use of high-energy x-rays or other particles to destroy tumor cells. Doctors may use radiation therapy to slow or stop the growth of the tumor. It is typically given after surgery and possibly along with chemotherapy. The most common type of radiation treatment is called external-beam radiation therapy, which is radiation given from a machine outside the body. When radiation treatment is given using implants, it is called internal radiation therapy or brachytherapy. External-beam radiation therapy can be directed at the tumor in the following ways:

Conventional radiation therapy. The treatment location is determined based on anatomic landmarks and x-rays.

3-dimensional conformal radiation therapy (3D-CRT). Using images from CT and MRI scans, a 3-dimensional model of the tumor and healthy tissue surrounding the tumor is created on a computer. This model can be used to aim the radiation beams directly at the tumor, sparing the healthy tissue from high doses of radiation therapy.

Intensity modulated radiation therapy (IMRT). IMRT is a type of 3D-CRT (see above) that can more directly target a tumor. It can deliver higher doses of radiation to the tumor while giving less to the surrounding healthy tissue.

Proton therapy. Proton therapy is a type of external-beam radiation therapy that uses protons rather than x-rays. At high energy, protons can destroy tumor cells. Proton beam therapy is typically used for tumors when less radiation is needed because of the location.

Stereotactic radiosurgery. Stereotactic radiosurgery is the use of a single, high dose of radiation given directly to the tumor and not healthy tissue. It works best for a tumor that is only in 1 area of the brain and certain noncancerous tumors. A modified linear accelerator is a machine that creates high-energy radiation by using electricity to form a stream of fast-moving subatomic particles. A gamma knife is another form of radiation therapy that concentrates highly focused beams of gamma radiation on the tumor. A cyber knife is a robotic device used in radiation therapy to guide radiation to the tumor target, particularly in the brain, head, and neck regions.

Fractionated stereotactic radiation therapy. Radiation therapy is delivered with stereotactic precision but divided into small daily doses called fractions given over several weeks, in contrast to the 1-day radiosurgery.

Depending on the size and location of the tumor, the radiation oncologist may choose any or several of the above radiation techniques.

Chemotherapy is the use of drugs to destroy tumor cells, usually by ending the cancer cells' ability to grow and divide. The goal of chemotherapy can be to destroy tumor cells remaining after surgery, slow a tumor's growth, or reduce symptoms.

A chemotherapy regimen, or schedule, usually consists of a specific number of cycles given over a set period of time. A patient may receive 1 drug at a time or combinations of different drugs given at the same time. Some drugs are better at going through the blood-brain barrier, and these drugs often used for a brain tumor.

Gliadel wafers are one way to give the drug carmustine. These wafers are placed in the area where the tumor was removed during surgery.

For people with glioblastoma and high-grade glioma, the latest standard of care is radiation therapy with daily low-dose temozolomide (Temodar). This is followed by monthly doses of temozolomide after radiation therapy for 6 months to 1 year.

A combination of 3 drugs, lomustine (Gleostine), procarbazine (Matulane), and vincristine (Vincasar), have been used along with radiation therapy. This approach has helped lengthen the lives of patients with grade III oligodendroglioma with a 1p19q co-deletion when given either before or right after radiation therapy.

Patients are monitored with a brain MRI while receiving active treatment. Patients often have regular MRIs to monitor their health after treatment is finished and the tumor has not grown.

V. EXAMPLES

The following Examples section provides further details regarding examples of various embodiments. It should be appreciated by those of skill in the art that the techniques disclosed in the examples that follow represent techniques and/or compositions discovered by the inventors to function well. However, those of skill in the art should, in light of the present disclosure, appreciate that many changes can be made in the specific embodiments which are disclosed and still obtain a like or similar result without departing from the spirit and scope of the disclosure. These examples are illustrations of the methods and systems described herein and are not intended to limit the scope of the disclosure. Non-limiting examples of such include but are not limited to those presented below.

Example 1—Materials and Methods

Cell lines and primary tumor cell culture. All patient specimens were collected after obtaining written informed consent from patients and families in accordance with approved IRB studies. The primary DIPG neurosphere line CCHMCDIPG-1 was aseptically isolated by dissociating the brain tumor tissue post-autopsy from a patient consented under the Pediatric Brain Tumor Repository (PBTR) study (IRB approved protocols 2013-1245 and 2013-5947) at Cincinnati Children's Hospital Medical center (CCHMC). Primary patient-derived neurospheres high-risk group-3 MB (MB004) (19,20), GBM (R0315-GBM), and DIPG) SU-DIPG-VI (21) and CCHMC-DIPG-1 (22)) were cultured in neurosphere stem cell media as described elsewhere (22,23). Patient-derived medulloblastoma cell lines collected from the same patient at diagnosis D-425, and at recurrence D-458 (24,25) were cultured in RPMI-1640 (Gibco) supplemented with 15% FBS. Primary normal human foreskin fibroblast (HFF) strain (ATCC CRL-2091), the HeLa human cervical carcinoma cell line, the human osteosarcoma cell lines Saos-2 (ATCC HTB-85) and U2OS (ATCC HTB-96) were purchased from the American Type Culture Collection. HFF cells were immortalized with hTERT (HFF+hTERT) by viral transduction as previously described (2). The source of other cell lines is referenced above. Commercially available cell lines were characterized at their original sources. All cells were expanded upon receipt or establishment for 2-3 passages and used within 1-2 months after thawing the cryopreserved cells without additional authentication. No testing was done by the authors for *Mycoplasma*. However, the inventors did not observe any evidence of their presence.

Telomerase activity assay. Telomerase activity was assayed using the TRAPeze Telomerase Detection Kit (Millipore). Cell extracts were prepared according to the manufacturer's protocol. 50-100 ng of total protein was used to assess the telomerase activity by performing polyacrylamide gel (12.5%) electrophoresis.

Drug treatment. 6-thio-dG (Metkinen Oy) was dissolved in DMSO:water (1:1) to prepare a 10 mM stock solution, aliquoted and stored in –20° C. For in vitro treatments, 1 mM final concentration was prepared in plain media. For in vivo studies, 6-thio-dG was prepared in a 5% DMSO solution. Kinase-inhibitors of ATM (KU-55933) (26) and ATR (VE-822) (27,28) were purchased from Selleckchem, and reconstituted in DMSO. Imetelstat (GRN163L) (29); Geron Corp. was reconstituted (1 mg/mL) in PBS.

Cell growth and sphere formation assay. After dissociating primary neurospheres by TrypLE express (Gibco), single cells were seeded in respective growth media in 6-well plates and were incubated for one week at varying concentrations (0.5 to 10 µM) of 6-thio-dG or DMSO. Fresh culture media were added every three days. Viable cell numbers were determined by trypan blue exclusion method. For sphere formation assay, MB004 single cells were seeded in limited dilution (10 cells/well in 96-well plate) and treated with DMSO or 6-thio-dG. Sphere formation was monitored by microscopy.

Cell cycle analysis. Following treatment with 6-thio-dG or DMSO, cells were collected in PBS, fixed with ice-cold 70% ethanol and were kept in –20° C. for at least an hour. Cells were then washed and stained with propidium iodide (PI) solution containing 25 µg/mL PI (Sigma), and 100 µg/mL Ribonuclease-A (Sigma) for 30 minutes in the dark. Flow cytometry was performed on BD FACS Canto II and cells were analyzed using FlowJo v.10 (FlowJo, USA) software.

Immunofluorescence and telomere FISH assay. Cells were fixed with 4% paraformaldehyde (PFA) for 15 minutes. Cells were then washed, permeabilized with 0.5% Triton-X-100 in PBS, blocked with 5% donkey serum and 0.3% Triton X-100 in TBS and incubated with primary antibodies against γH2A.X (1:500, rabbit), or cleaved caspase-3 (1:400, rabbit) (Cell Signaling); and/or TRF2 (1:200) (Mouse; NOVUS), as applicable, for overnight followed by TBST wash (×3) next day. Corresponding secondary antibodies were added (Alexa-Fluor 488- or 594-conjugated donkey anti-rabbit, or anti-mouse (1:500) (Jackson ImmunoResearch) for 1 hour and washed with TBS (×3) before mounting. For telomere-FISH, fixed and permeabilized cells were dehydrated with a graded ethanol concentration series, air-dried and covered with hybridization solution (70% formamide, 0.5% Blocking Reagent (Roche Diagnostics) diluted in 100 mM maleic acid and 150 mM sodium chloride, and 10 mM Tris (pH 7.5)) with 300 ng/mL PNA (CCCTAA)$_3$-Cy3 (SEQ ID NO: 1) (Biosynthesis, USA), and denatured for 6 minutes at 84° C. followed by hybridization for at least two hours at room temperature. Cells were washed three times with 70% formamide and 10 mM Tris (pH 7.5) and three times with TBS. Finally, they were embedded with mounting media with DAPI (Vector Laboratories H1200). Images were captured with 60× oil objective on Nikon Eclipse Ti confocal microscope.

Senescence assay. Senescence-associated β-galactosidase was detected as previously described (2). Cells were observed under the microscope until the development of the blue color and the reaction was terminated. Images were captured; stained and unstained cells were counted from multiple fields to quantitate the percent senescent cells.

Western blot. Western blot was performed as described previously (22). Antibodies used were against ATMS1981P (R & D Systems); ATM (SIGMA); ATR-T1989P (GeneTex); and ATR, CHK1-S345P, CHK1, CHK2-T68P, CHK2, Cleaved Caspase-3, and β-actin (Cell Signaling). Bands were visualized using ECL with Azurec500 imaging system (Azure Biosystems). Band intensities were quantified using ImageJ software (Ver. 1.49u, NIH, USA).

DNA extraction and agarose gel electrophoresis. Genomic DNA was extracted from DMSO or 6-thio-dG treated HFF, HFF+hTERT, and U2OS cells using Puregene Kit (Qiagen, USA) following the manufacturer's protocol. 100 ng of each sample was run on a 0.7% agarose gel followed by staining with GelRed Nucleic Acid Gel Stain (Biotium). Bands were visualized under UV illuminator.

Mouse subcutaneous and orthotopic xenograft. Athymic Ncr-nu/nu female mice (6-7 weeks old) were subcutaneously injected with 10,000 MB004 cells. Mice were weighed and distributed in two groups (control and 6-thio-dG). After tumor-establishment (day 23-24 post-implantation) with an average volume of 100-200 mm$_3$, mice were injected intraperitoneally (i.p) every 2 days with 6-thio-dG (2.5 mg/kg) or DMSO-PBS (vehicle) for 3-4 weeks until euthanization. Tumors were measured by slide calipers taking two longest tumor-diameters (length and width) perpendicular to each other and volumes were calculated by using the formula: $(\pi/6) \times d_3$, where d=mean diameter. For orthotopic xenograft, CCHMC-DIPG-1 luciferase-positive cells (10,000) were injected in the brain of NRG (NOD.Cg-Rag1$_{tm1Mom}$ Il2rg$_{tm1Wjl}$/SzJ) mice. Briefly, mice were injected stereotactically with 2 µl medium containing 10,000 luciferase-positive cells. The coordinates for injection were 0.8-1 mm posterior to lambda suture and 3.5 mm deep, corresponding to the pons location in the brain. Tumors were visualized by luminescence using IVIS Spectrum CT in vivo imaging system (PerkinElmer). All animal procedures were approved by the Institutional Animal Care and Use Committee (IACUC) (protocol #IACUC2015-0066, CCHMC).

Immunohistochemistry. Formalin-fixed paraffin-embedded (FFPE) sections were deparaffinized in xylene followed by rehydration through a graded ethanol concentration series. Heat-induced antigen retrieval was performed by steaming slides for 20 minutes in 10 mM Citrate buffer (pH 6.0). Endogenous peroxidase activity was quenched with 1% H$_2$O$_2$ followed by washing, blocking with 10% goat serum in TBST for an hour, and incubating with primary antibody Ki67 (1:1500) (rabbit; Abcam), or Cleaved caspase-3 (1:1000) (rabbit; Cell Signaling) in 2% goat serum in TBST overnight at 4° C. Slides were washed with TBST (×3) and were treated with biotinylated anti-rabbit secondary antibody (1:500) and signal-amplified using ABC Kit (Vector Laboratories). Signal was visualized with DAB (Vector Laboratories) and counterstained with Harris Hematoxylin (Sigma). H & E staining was performed using hematoxylin-1 and eosin-Y (Thermo Scientific). Tissues were mounted with Permount (Fisher Scientific) and imaged by Nikon eclipse 80i microscope.

Tissue TIF assay. Tissue samples were pre-fixed with 4% PFA and were cryo-protected in 25% sucrose/PBS solution, then embedded in OCT freezing molds with Neg-50 (VWR) in acetone and dry ice followed by cryo-sectioning. Heat-induced antigen retrieval and Telomere-FISH was performed as described above. The samples were incubated in blocking solution (5% donkey serum, 0.3% Triton X-100 in TBS) for 30 minutes and treated with anti-53BP1 (rabbit 1:500; Novus Biologicals) for 1 hour at room temperature. After washing in TBST (×3), the samples were incubated with secondary antibody Alexa-Fluor 488-conjugated donkey anti-rabbit (1:400; Jackson ImmunoResearch), and washed in TBS (×3). The samples were embedded in mounting media with DAPI (Vector Laboratories H1200). Images were captured with 60× oil objective on Nikon Eclipse Ti confocal microscope.

Statistical analysis. The statistical analyses were performed by Student's t-test or multiple-way ANOVA as required using the GraphPad Prism (version 7.02). Each experiment was repeated at least twice. Error bars represent standard deviation of at least three replicate wells or fields from one representative experiment considered as technical replicates, or from independent experiments or different animals for biological replicates. Differences were considered significant at $P<0.05$.

Figure 1B:
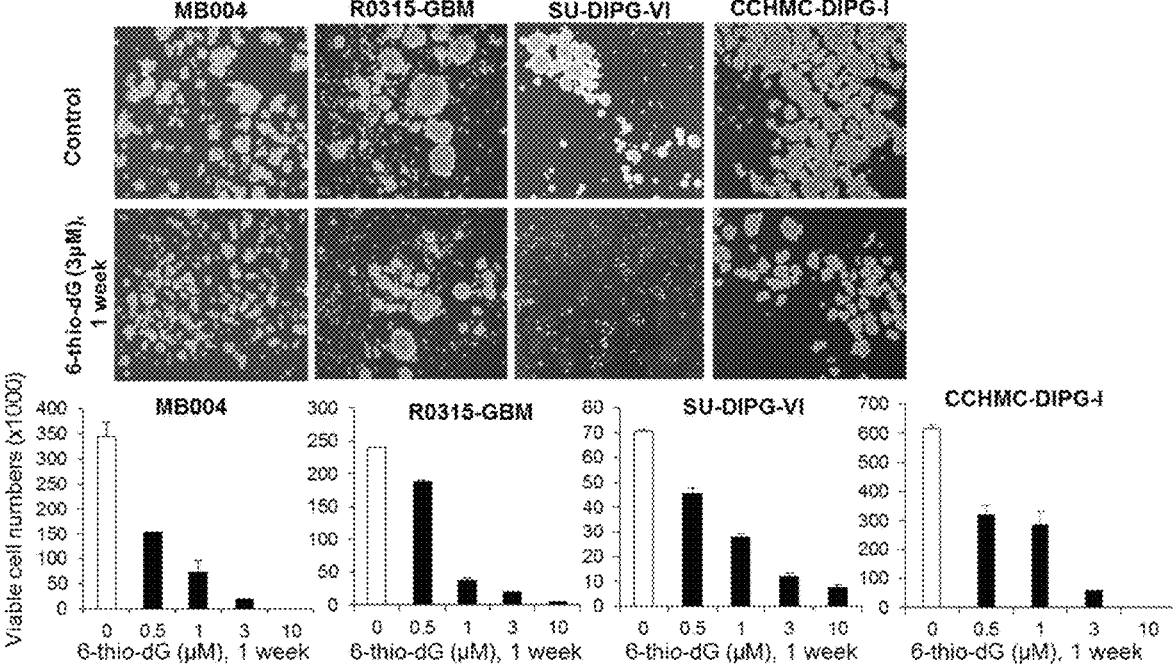
Figure 1C:
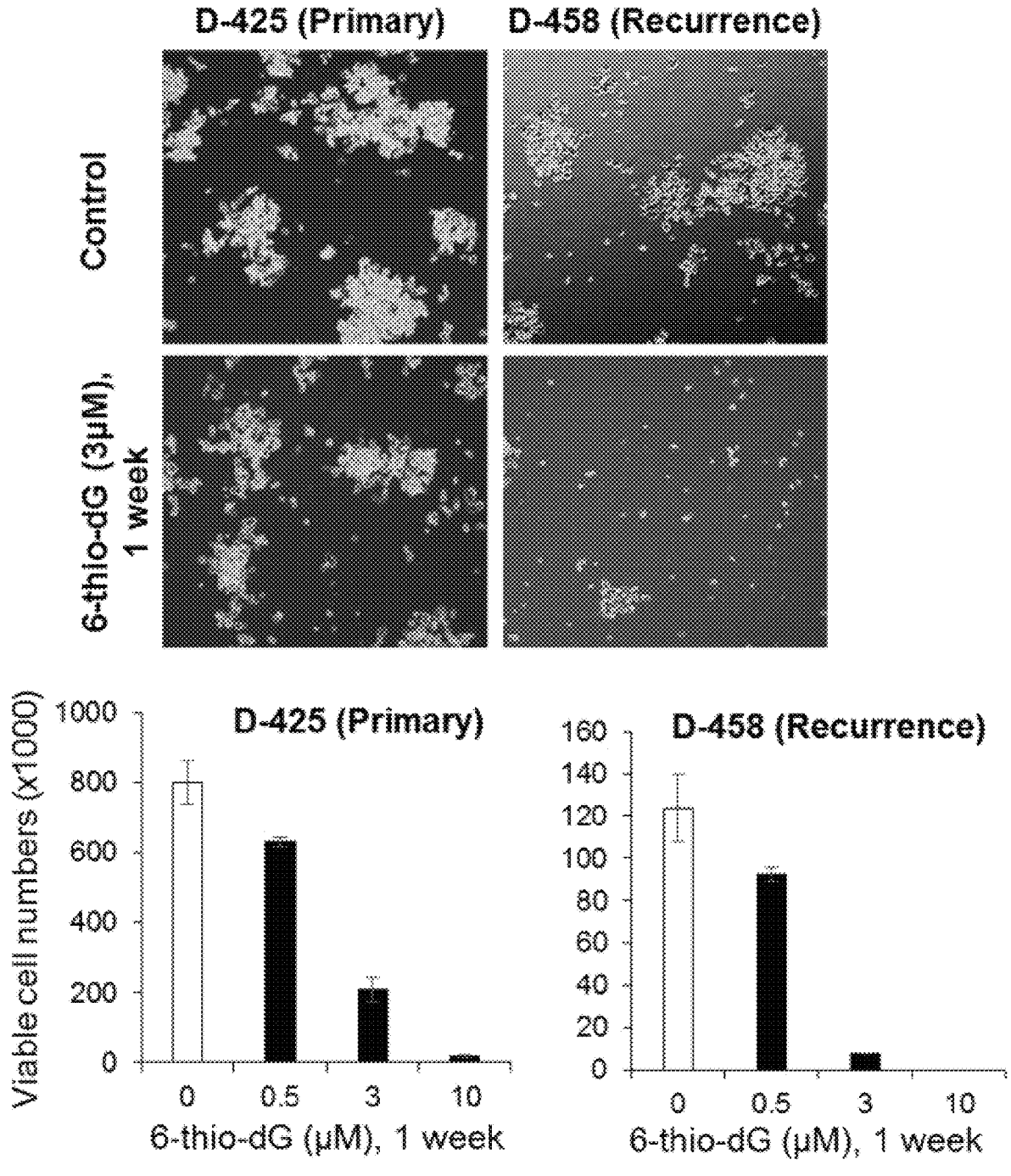
Figure 7:
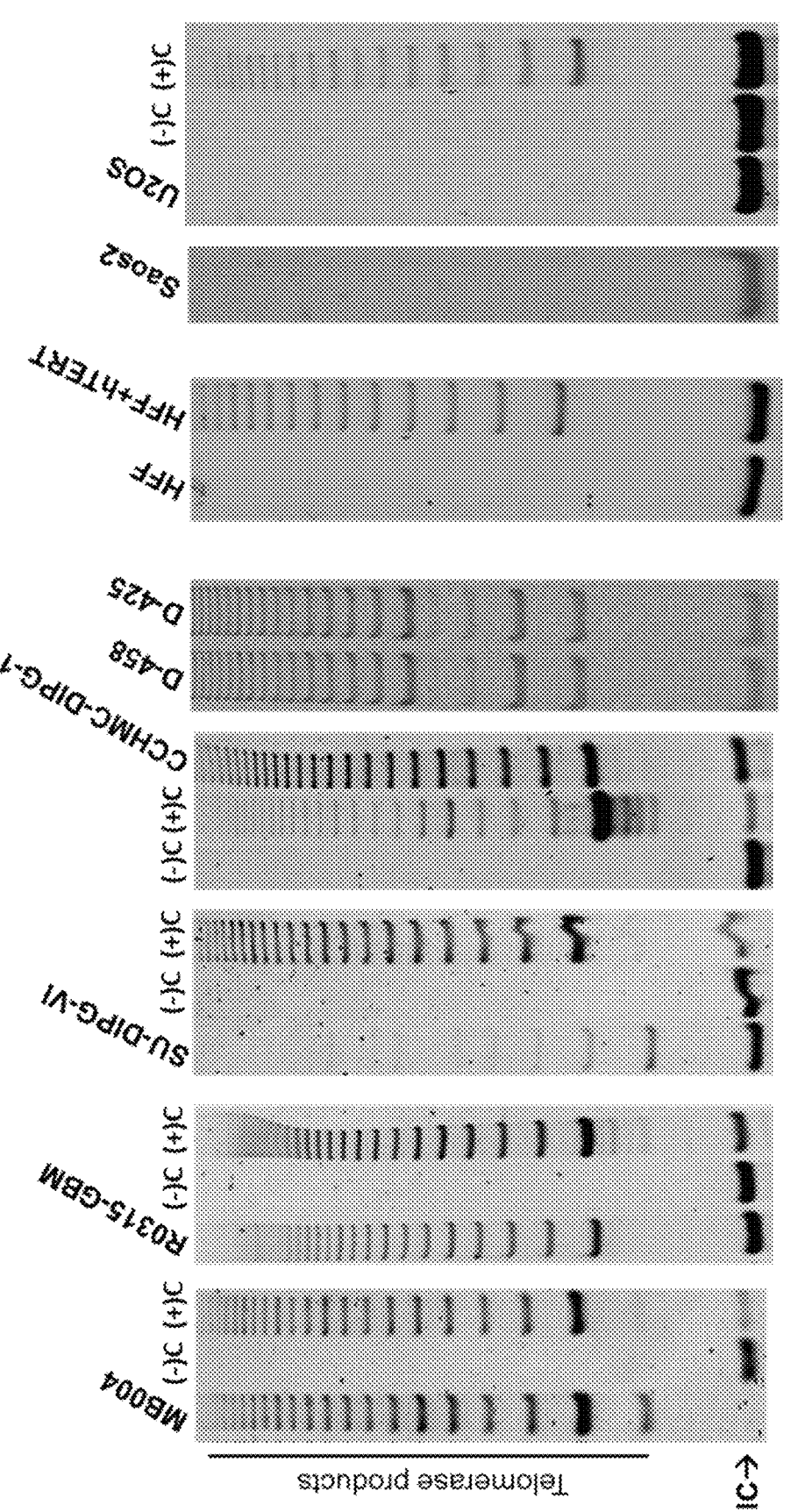
FIG. 7. Telomerase activity in pediatric brain tumor cells. MB004, R0315-GBM, SU-DIPG-VI, CCHMC-DIPG-1, D-458, D-425, in normal diploid fibroblast cells HFF and HFF+hTERT, and in osteosarcoma cells Saos-2 and U2OS. (−) C, (+) C, and IC indicate negative control, positive control, and internal control respectively. Telomerase products are indicated.

Example 2—Results 6-thio-dG selectively inhibits cell growth of telomerase-positive tumor cells. One of the major setbacks in oncology is the ability of certain cancers to recur after minimal or undetectable disease is achieved with aggressive therapies. Cancer stem-like cells have been proposed to represent a sub-population of cells within a tumor that self-renew to promote tumor growth and recurrence. In the present study, primary stem-like cells were derived from DIPG, HGG and MB patients' tumor tissue and expanded in neurosphere stem cell media. Table S1 indicate genetic features and subtypes of the cell lines. The inventors tested 6-thio-dG in a panel of telomerase-positive pediatric brain tumor cells, including high-risk group-3 MB (MB004), GBM (R0315-GBM), and DIPG (SU-DIPG-VI and CCHMC-DIPG-1) along with a panel of control cell lines, consisting of normal primary human foreskin fibroblasts (HFF, telomerase-negative), HFF-ectopically expressing hTERT (HFF+hTERT, telomerase-positive), HeLa cells (telomerase-positive), and osteosarcoma cells Saos-2 (Telomerase-negative, Alternative Lengthening of Telomeres or ALT-positive). Telomerase activity was verified by the gel-based TRAP assay (FIG. 7). The inventors and others previously reported that under serum-free culture conditions, HGG-, DIPG- and medulloblastoma neurospheres expressed neural stem cell markers such as nestin, CD133, and olig2, and were capable of self-renewal and differentiation in the presence of serum (22,23). These cancer stem-like cells are thought to be responsible for tumor recurrence (30). Moreover, the inventors confirmed that these cells are able to establish tumors in immunosuppressed mice. The cells were treated with 0.5 to 10 μM of 6-thio-dG every three days for one week. As expected, treatment with 6-thio-dG inhibited cell growth in a dose-dependent manner in all telomerase-positive cells, including brain tumor cells, with a minor to no effect in telomerase-negative cells HFF and Saos-2 cells up to 3 μM (FIGS. 1A-B). Interestingly, 6-thio-dG effectively inhibited cell growth of both patient-derived medulloblastoma cell lines collected from the same patient at diagnosis, D-425 cells (biopsy of cerebellar primary tumor of 6-year old boy) and at recurrence D-458 cells (tumor cells in CSF following failure of radio- and chemotherapy) (24,31) (FIG. 1C). All telomerase-positive cells including brain tumor cells were highly sensitive compared to telomerase-negative cells as evidenced by the $IC_{50}$ ranging 0.14-1.45 μM (Table S2). Telomerase dependency of 6-thio-dG was further verified by using imetelstat (IMT). HFF and HFF+hTERT cells were treated with either 6-thio-dG or IMT, or in combination. The inhibition of telomerase activity by IMT treatment was confirmed by the TRAP assay (FIG. 8A). As expected, the inhibition of cell growth by 6-thio-dG in the combination treatment was markedly reduced pre-treated with IMT (FIGS. 8B-C), indicating that the 6-thio-dG effect is largely dependent on the presence of telomerase.

Figure 2A:
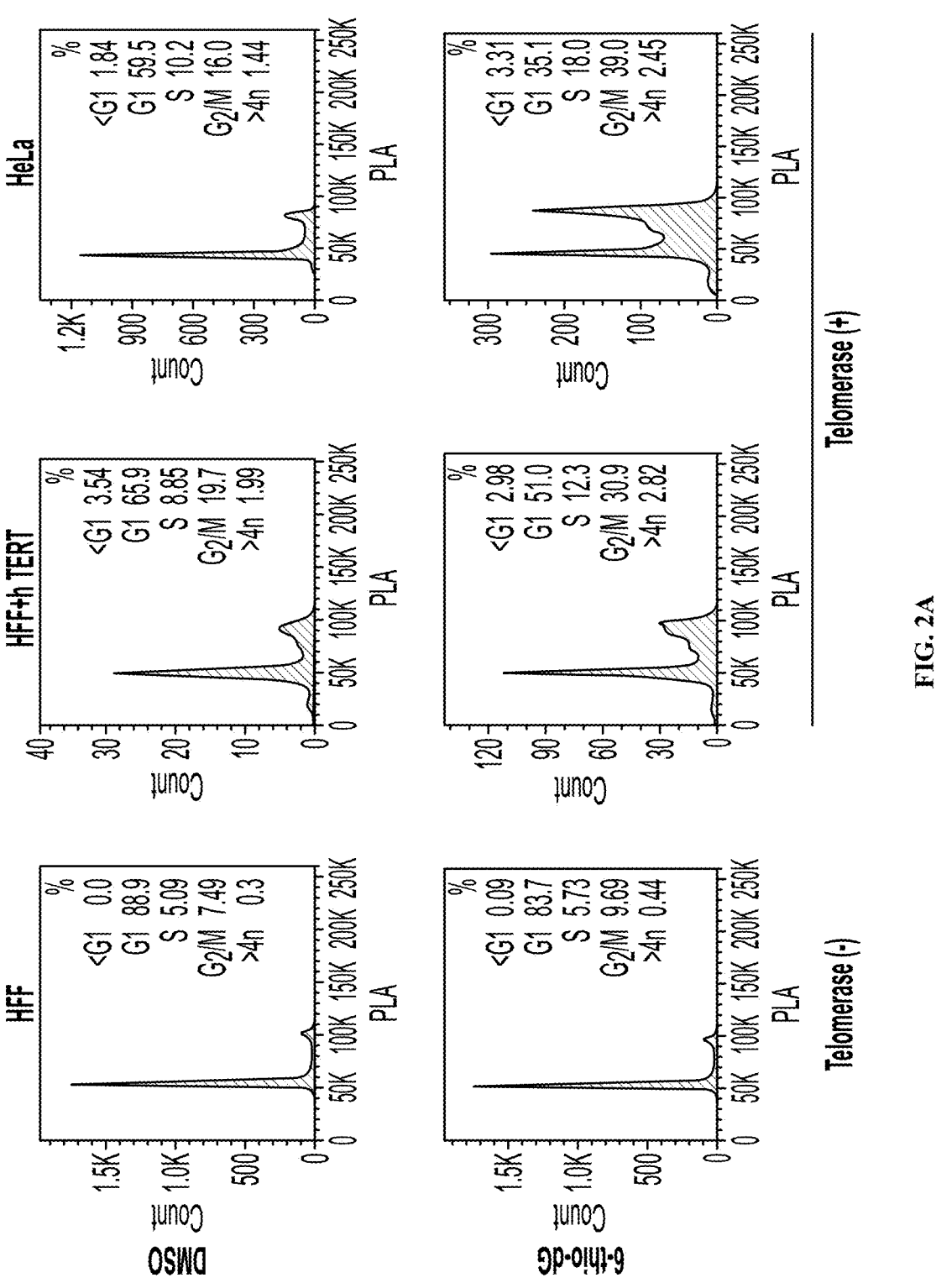
FIGS. 2A-D-3. 6-thio-dG induces persistent $G_2$/M cell cycle arrest in telomerase-positive cells.
Figure 2B:
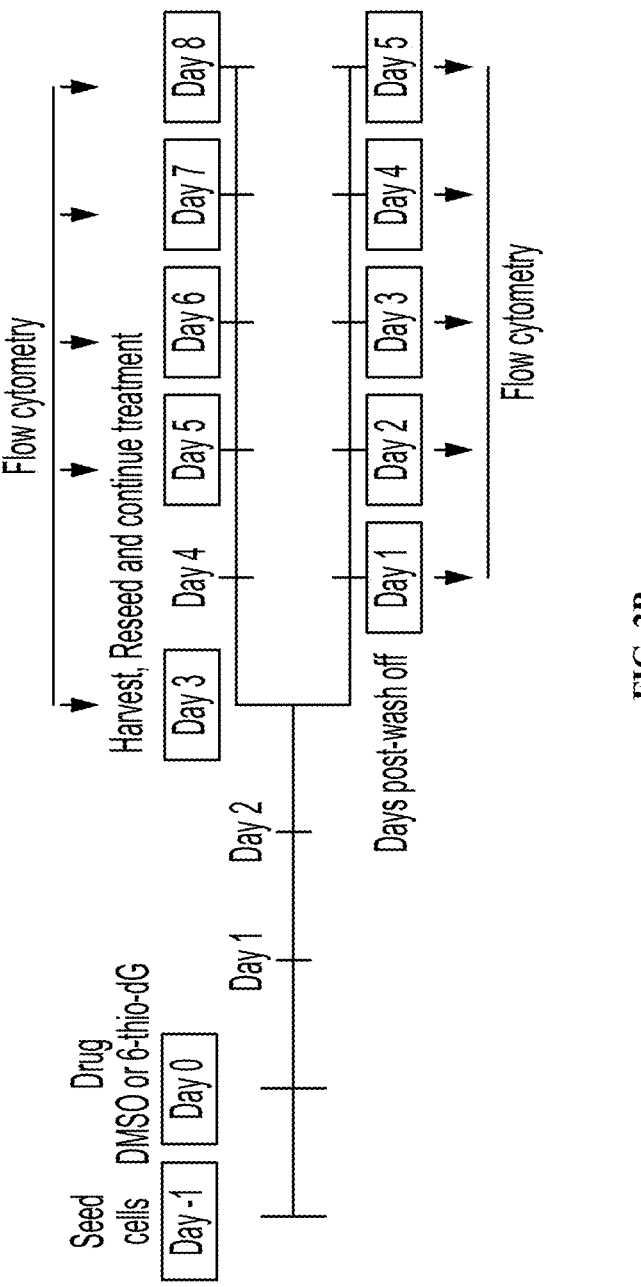
Figure 2C:
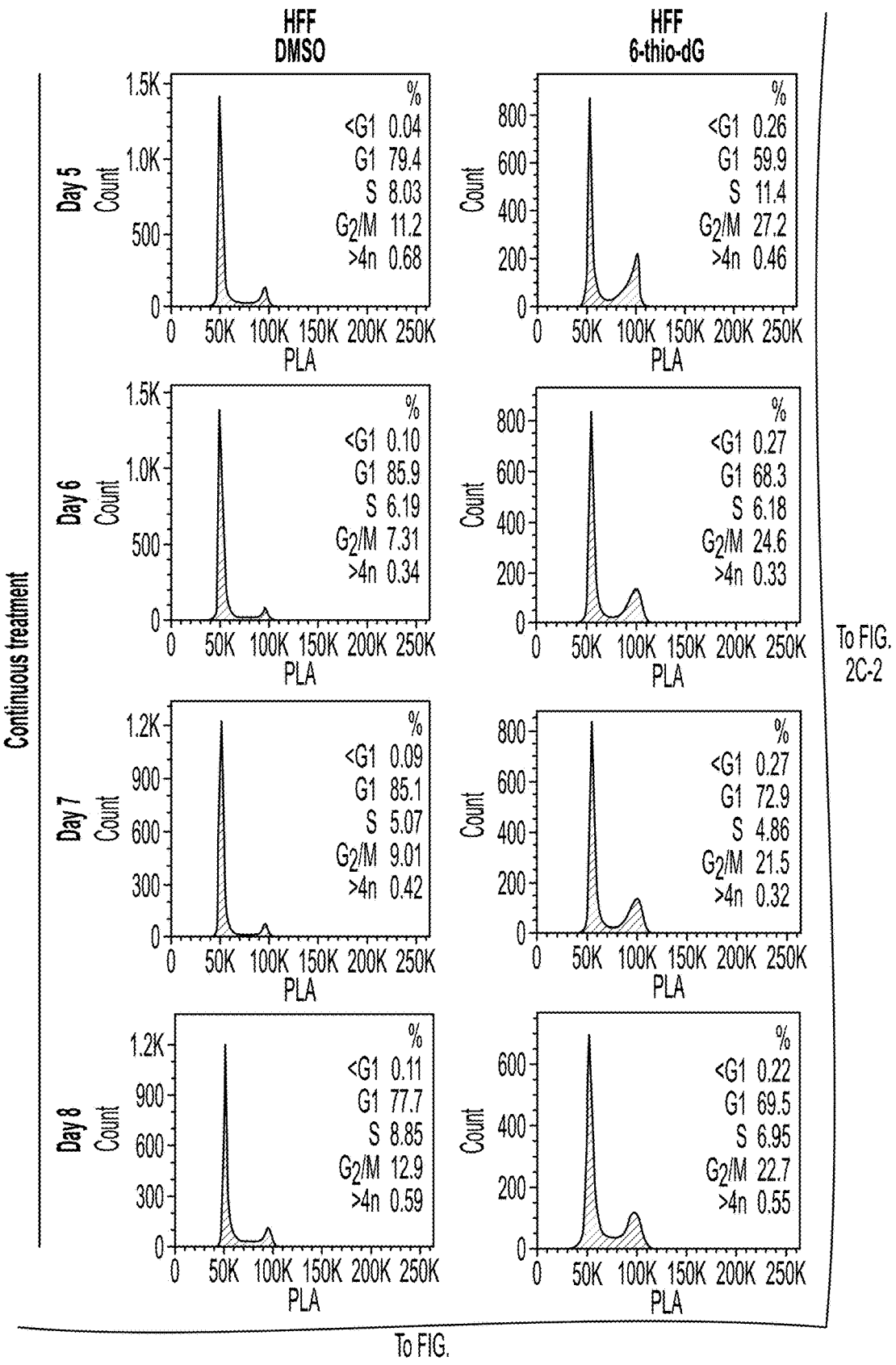
Figures 1, 2C:
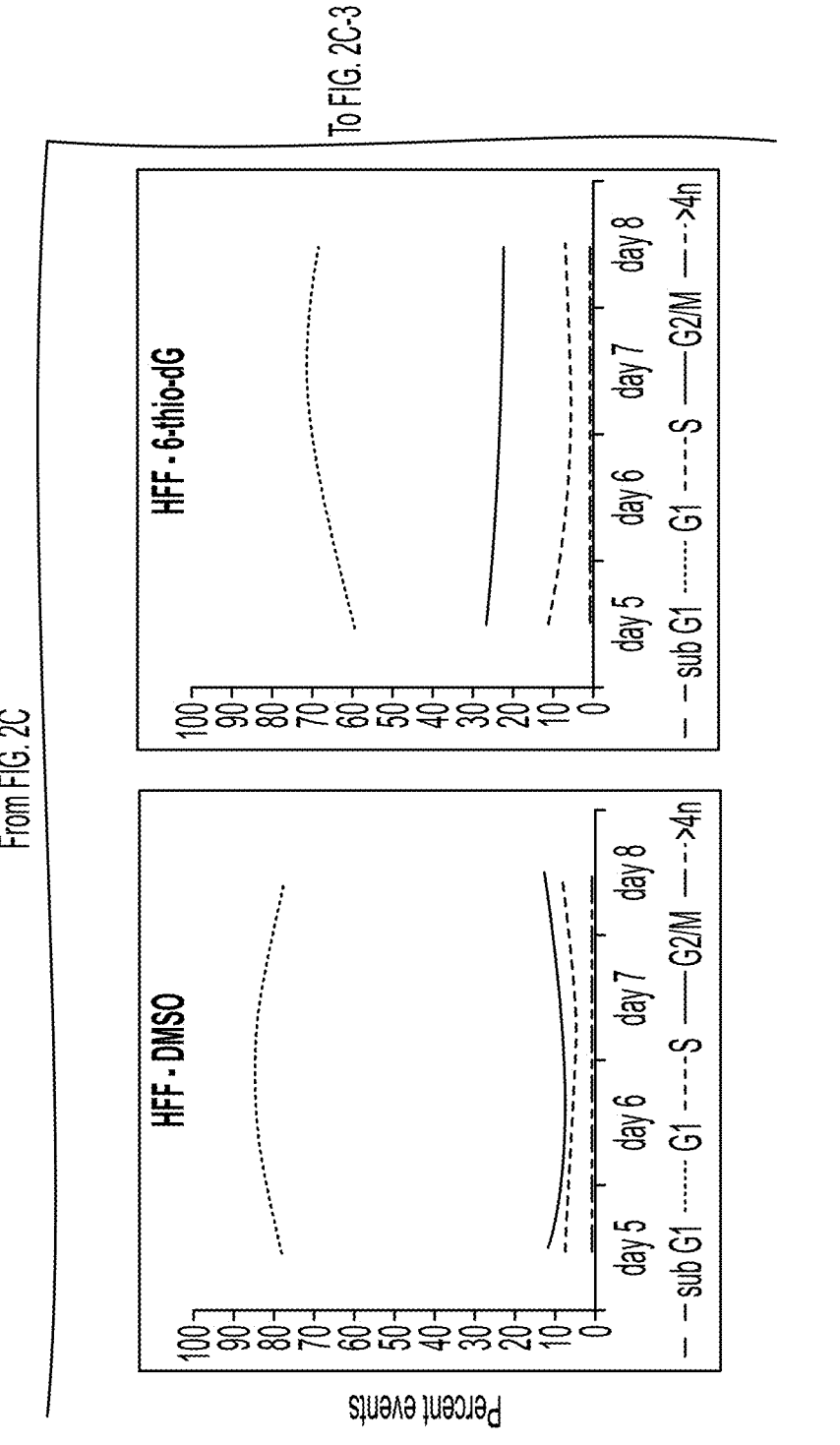
Figures 2, 2C:
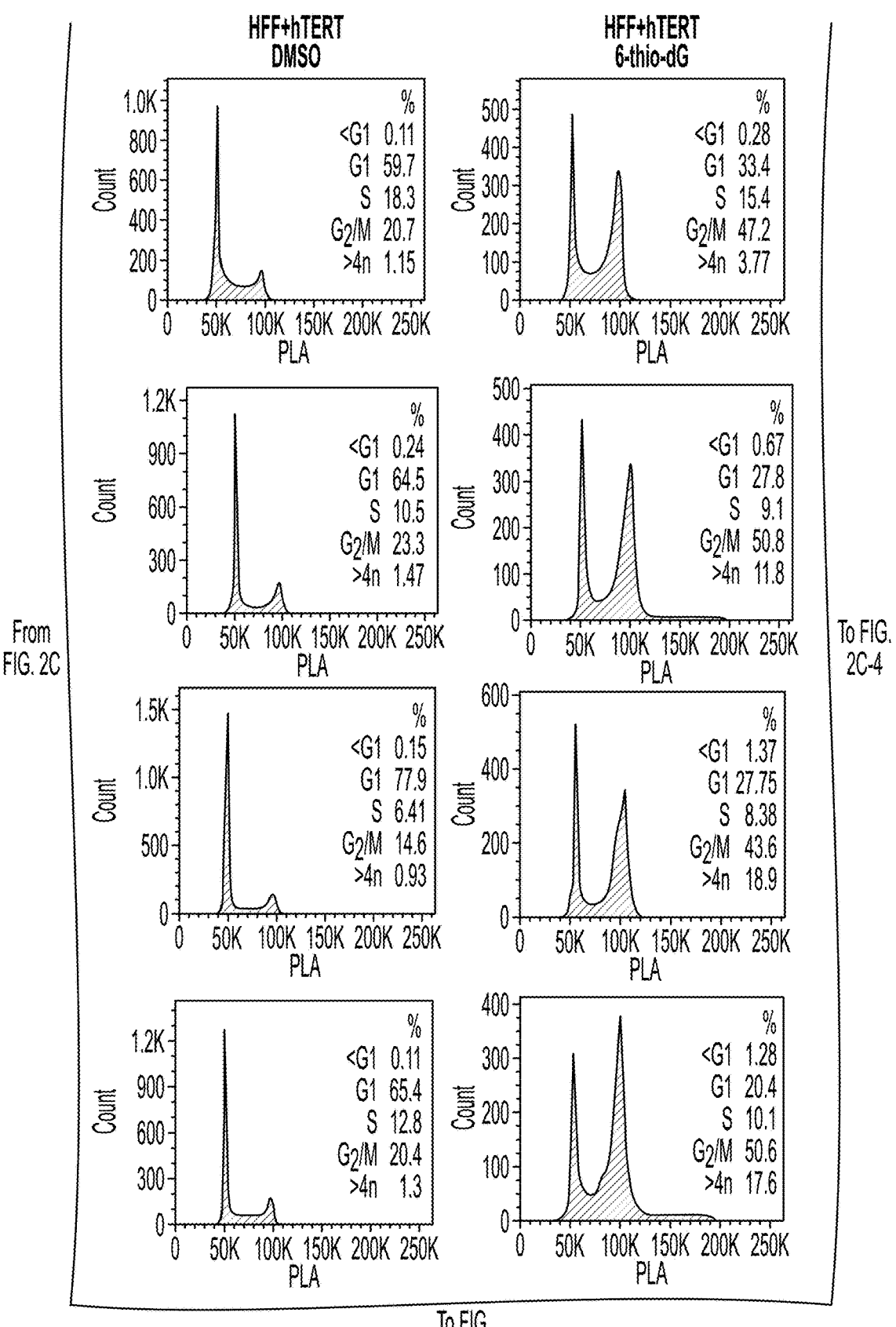
Figures 2, 2C, 3:
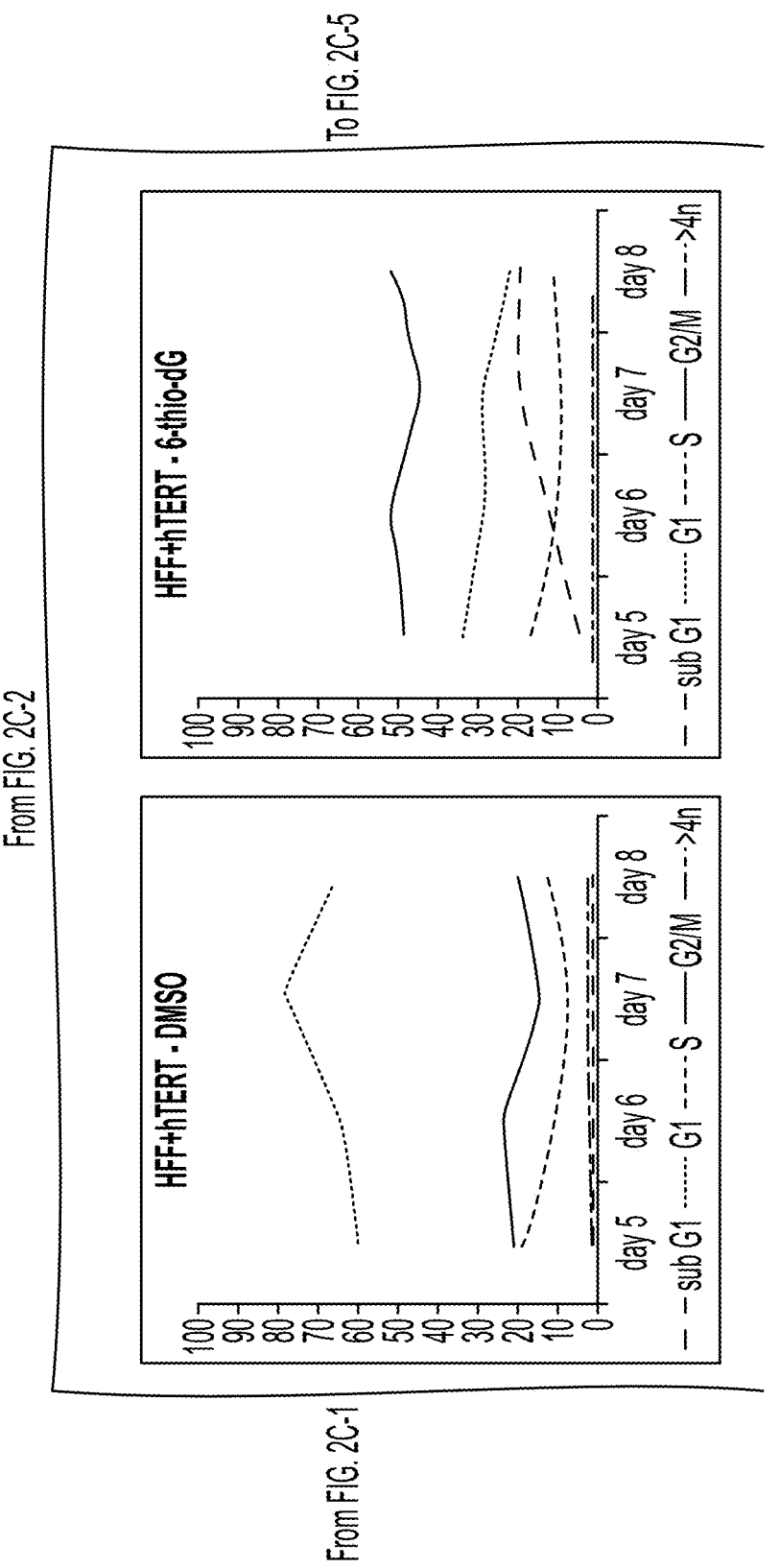
Figures 2, 2C, 3, 4:
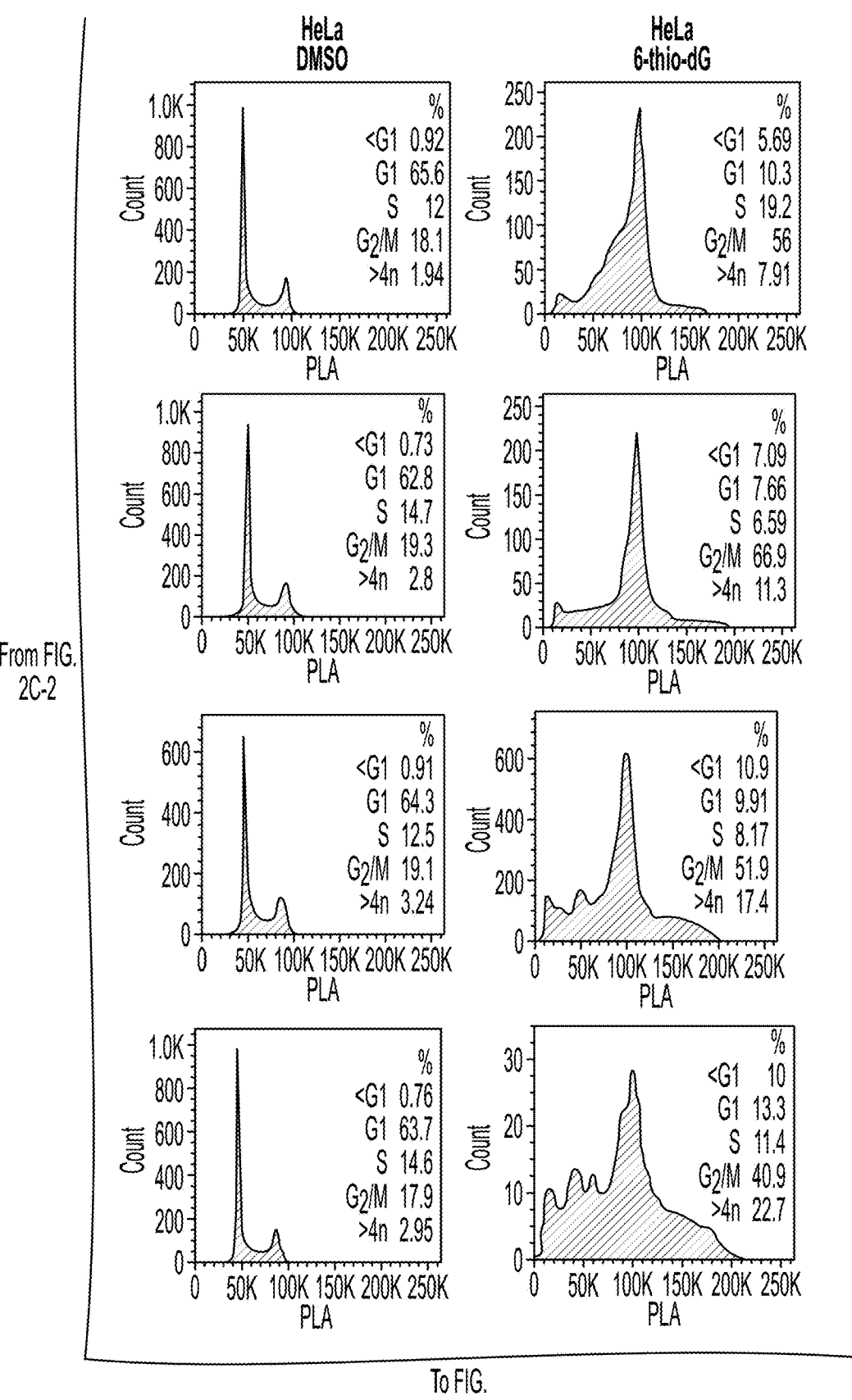
Figures 2, 2C, 3, 4, 5:
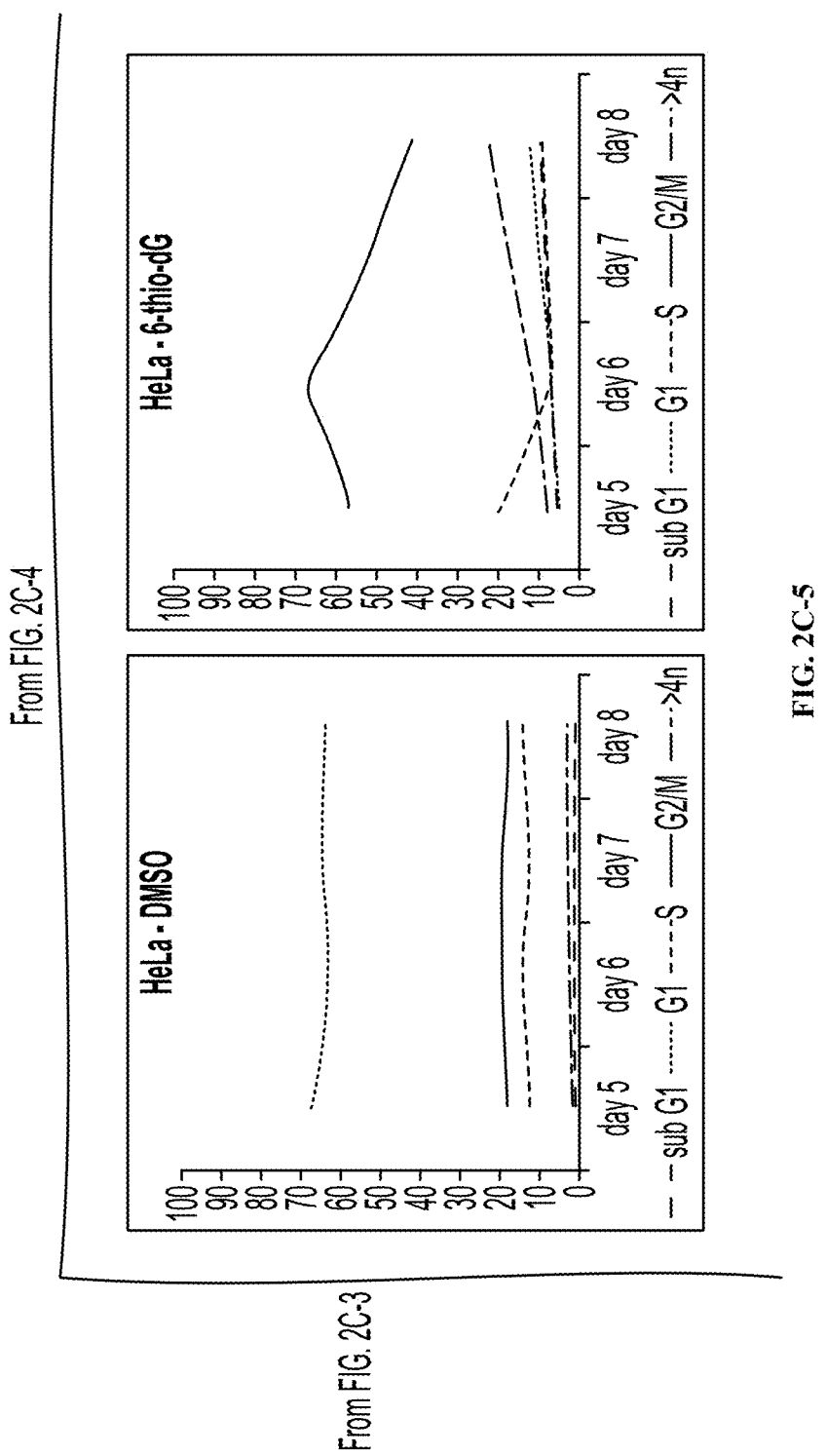
Figure 2D:
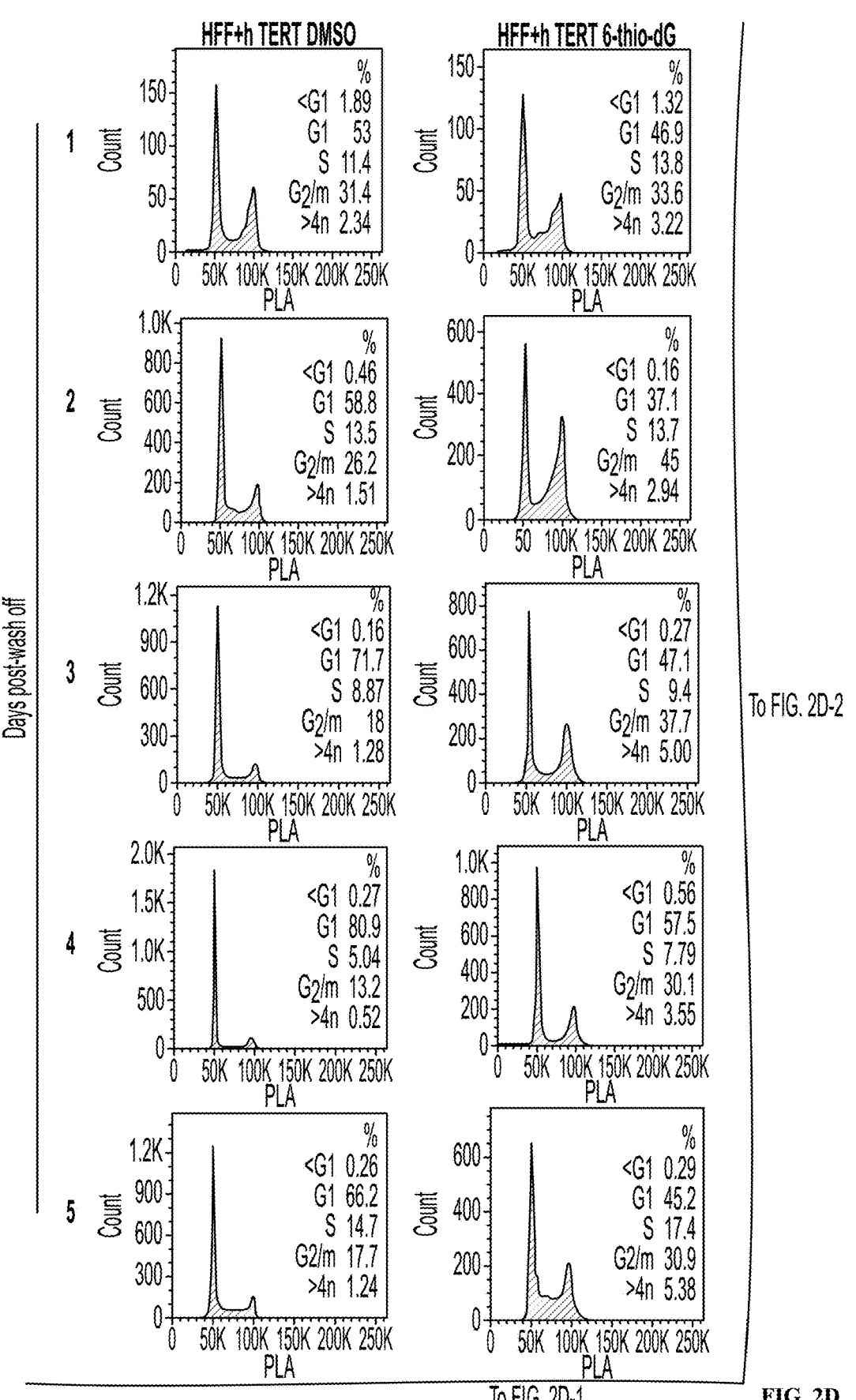
Figures 1, 2D:
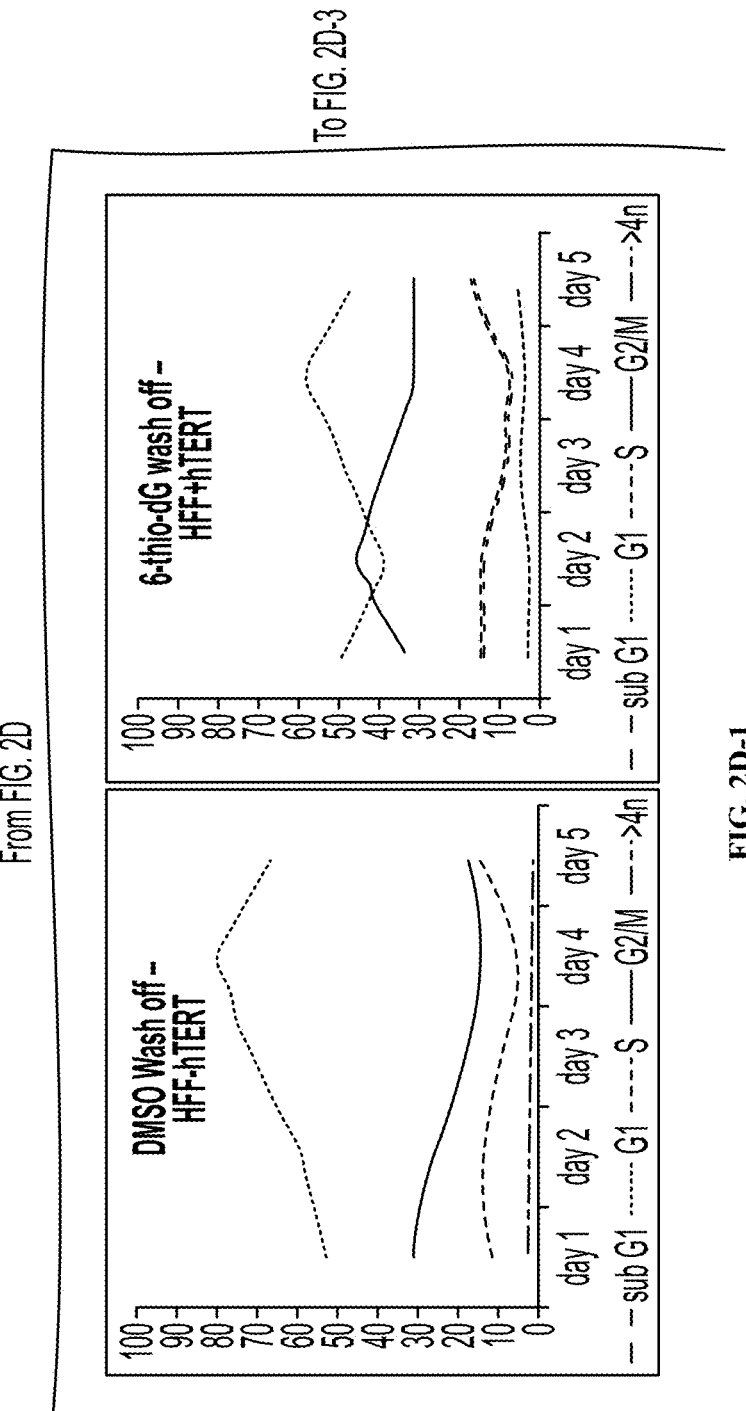
Figures 2, 2D:
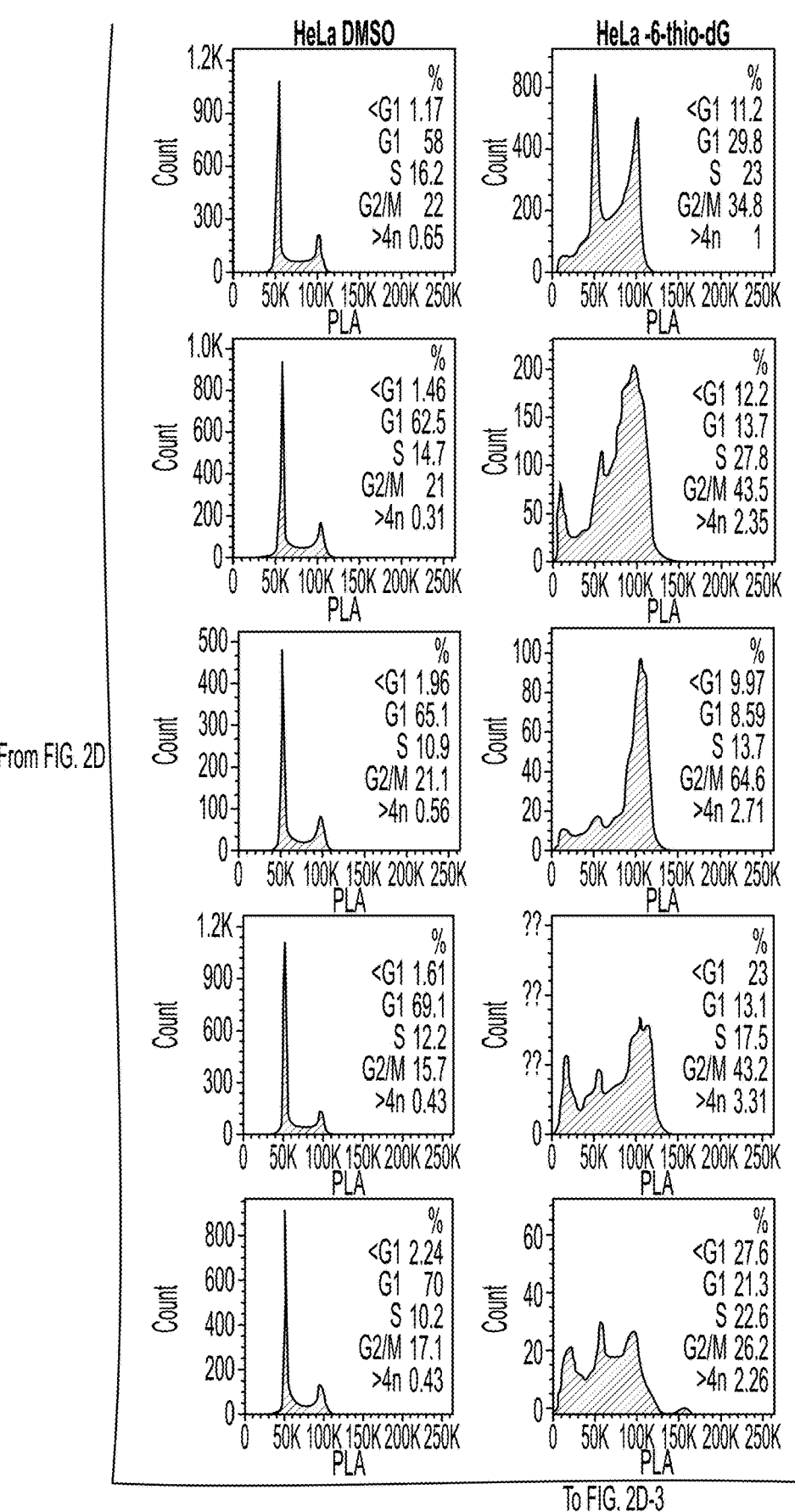
Figures 2, 2D, 3:
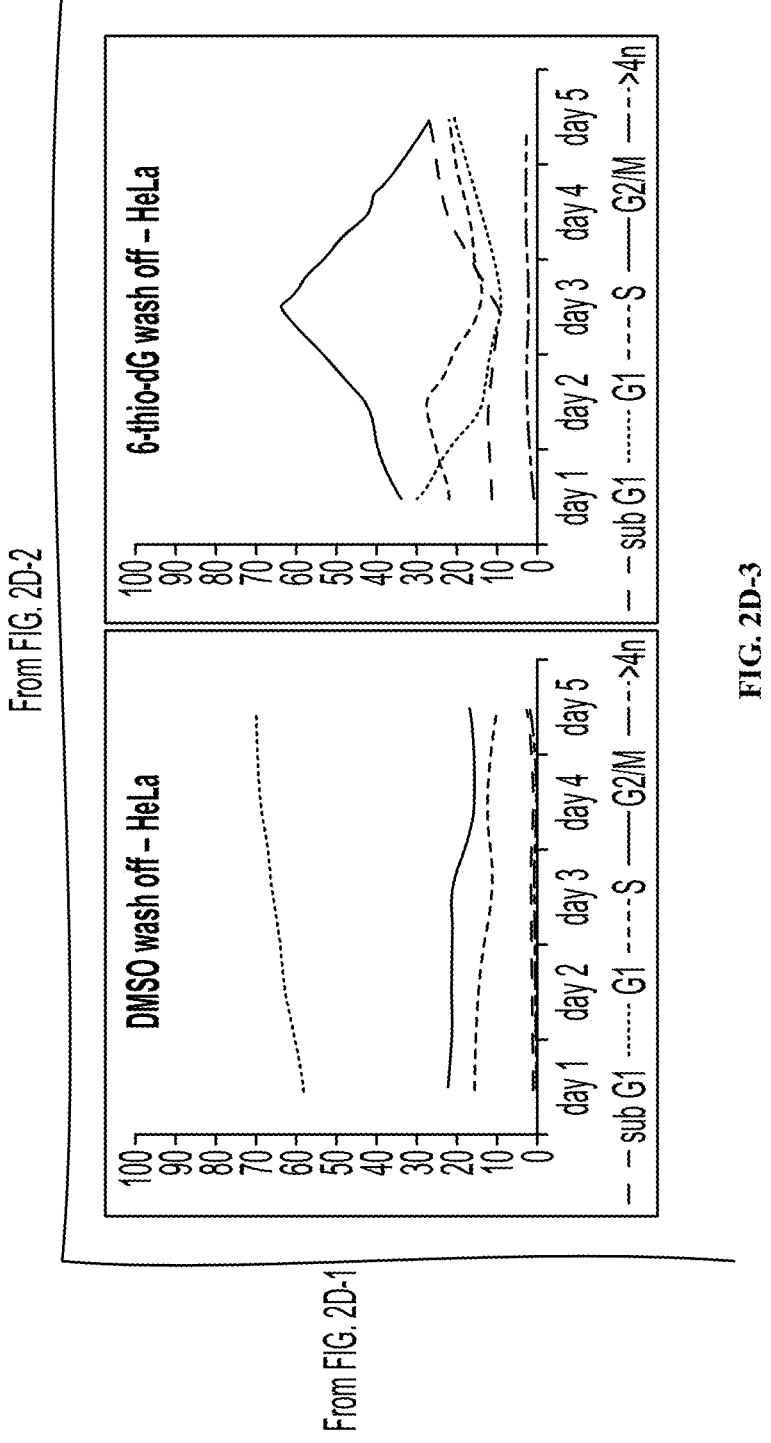

6-thio-dG induces sustained $G_2/M$ cell cycle arrest in telomerase-positive cells. Next, the inventors investigated the mechanistic aspect of 6-thio-dG-induced DNA damage response (DDR). Cell growth inhibition caused by 6-thio-dG treatment prompted the inventors to check its effect on cell cycle progression. Three days treatment with 3 μM of 6-thio-dG caused $G_2/M$ arrest in telomerase-positive cells HFF+hTERT and HeLa. In contrast, this effect was negligible in telomerase-negative cells HFF (FIG. 2A). Further, they assessed the long-term effect of 6-thio-dG on the cell cycle profile as illustrated in FIG. 2B. In continuous treatment, 6-thio-dG-induced $G_2/M$ arrest was sustained and more pronounced in telomerase-positive normal cells (HFF+hTERT) along with an increase in >4n cell population compared to telomerase-negative HFF cells (FIG. 2C). For Hela cells, continuous treatment caused a sharp increase in $G_2/M$, >4n and sub-$G_1$ cell populations, indicating aneuploidy and cell death. $G_2/M$ fraction increased after prolonged treatment of HFF cells with 6-thio-dG, likely due to the accumulation of genomic damage. In contrast to telomerase-positive cells, no increase in sub-$G_1$ and >4n population was noticed. Interestingly, even when the drug was removed from the media (FIG. 2B), 6-thio-dG effect on cell cycle progression persisted several days after drug withdrawal in Hela cells (FIG. 2D). In HFF+hTERT cells, $G_2/M$ and >4n accumulation decreased over time and the cell cycle profile partially reverted to that of the vehicle control. These results indicate that 6-thio-dG treatment has limited effect in normal cells (HFF), and causes $G_2/M$ arrest, aneuploidy and cell death in Hela cells. This effect was sustained several days after drug withdrawal in cancer cells but declined in normal telomerase-positive cells (HFF+hTERT).

Figure 3A:
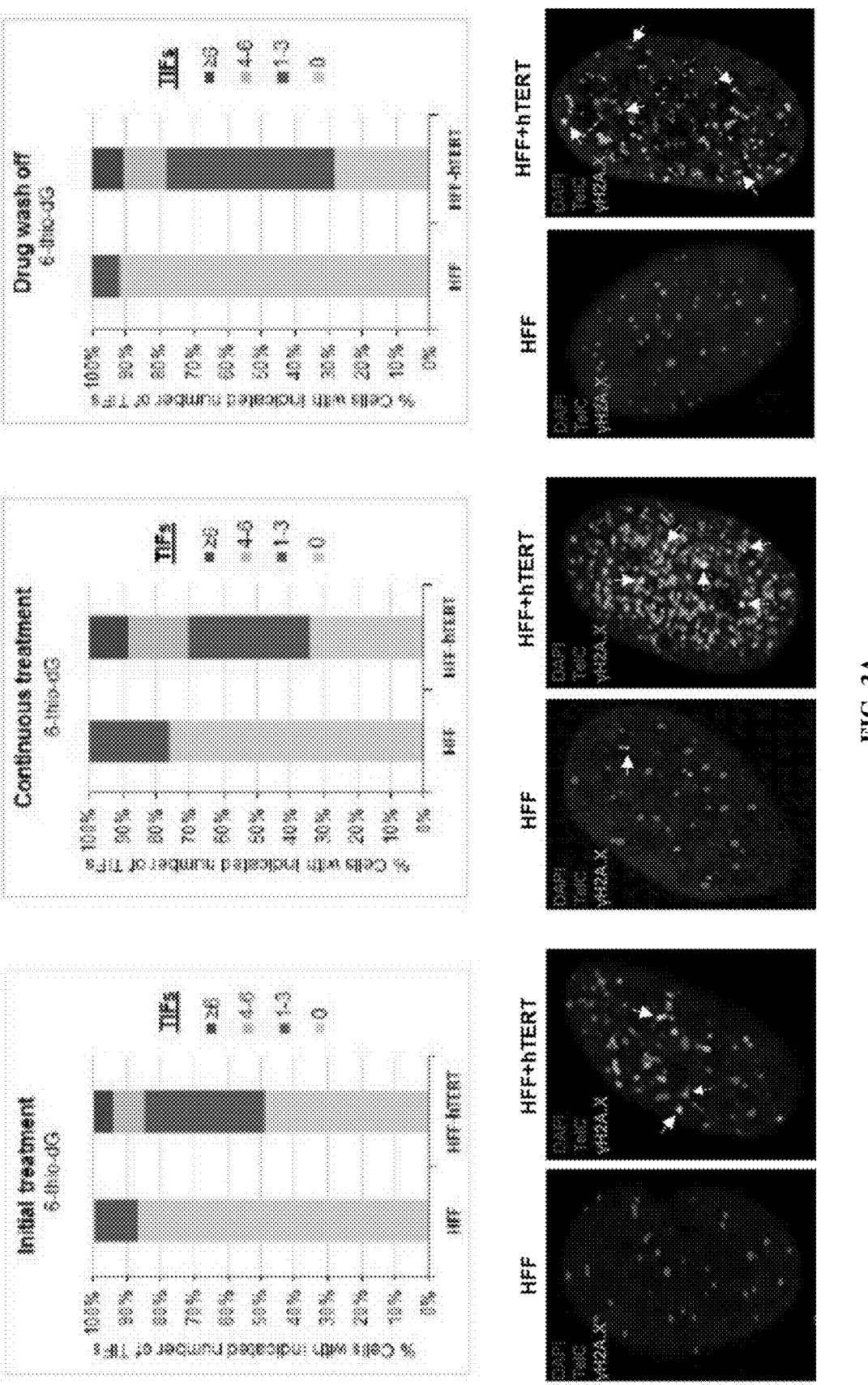

6-thio-dG induces persistent telomere dysfunction in telomerase-positive cells. Previous studies have shown that 6-thio-dG treatment leads to telomere dysfunction-induced foci (TIFs) in telomerase-positive cells but not in telomerase-negative cells (17). The inventors visualized TIFs by FISH combined staining using γH2AX co-localization with a telomere specific PNA probe. As expected, 6-thio-dG caused an acute increase of the number of cells with TIFs (~25%) in telomerase-positive cells, HFF+hTERT, after two days (FIG. 3A). TIF formation was limited in telomerase-negative cells HFF with less than 3% after 2 or 5 days treatment. This effect was amplified over time, ~34% of cells were TIF-positive at 5 days continuous treatment (FIG. 3A). Interestingly, ~31% of cells were still TIF-positive in telomerase-positive cells 3 days after drug withdrawal while TIFs completely disappeared in telomerase-negative cells. Furthermore, IMT treatment inhibited 6-thio-dG-induced TIF formation in HFF+hTERT (FIG. 8D) confirming telomerase dependency of 6-thio-dG-induced TIFs. As observed in the previous study (17), 6-thiodG also caused a modest increase in genomic DNA damage in telomerase-negative cells. This general damage was more evident in telomerase-positive cells (FIG. 3A). Importantly, TIFs-negative cells treated with 6-thio-dG displayed markedly reduced genomic DNA damage suggesting that TIFs exacerbate genomic DNA damage (FIG. 9A). Indeed, the inhibition of telomerase using IMT reduced the genomic DNA damage in cells treated with 6-thio-dG (FIG. 9B). Since telomeres are only $\frac{1}{6000}^{th}$ of the human genome, and TIF that is observed is unlikely to be by chance alone and emphasizes the importance of telomerase mediating the toxic effects of 6-thio-dG.

Figure 3B:
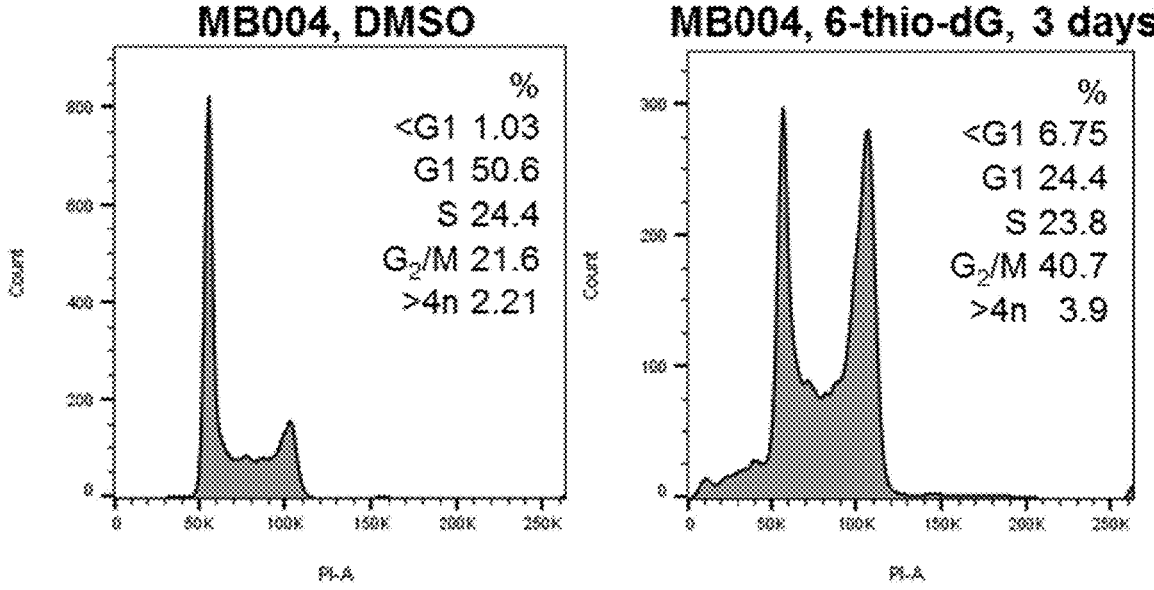
Figure 3C:
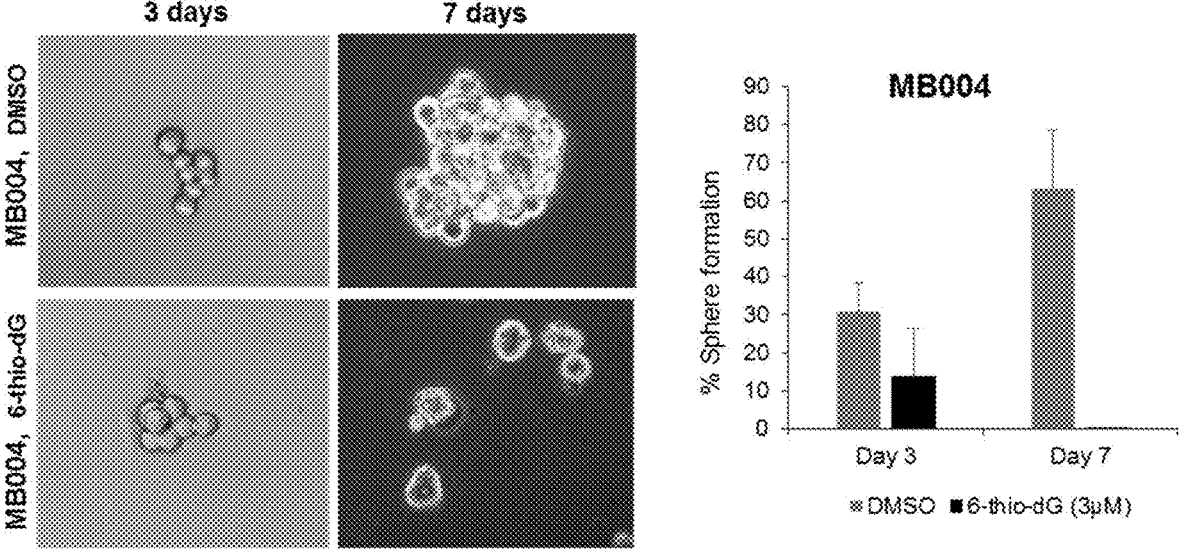

Next, the inventors evaluated the effect of 6-thio-dG treatment in telomerase-positive primary high-risk group 3 medulloblastoma stem-like cells MB004. Treatment with 3 μM of 6-thio-dG for 3 days resulted in an increase in sub-G$_1$ and G$_2$/M cell populations and a total abolition of sphere formation ability at day 7 (FIGS. 3B-C). Of note, at day 3, cells treated with 6-thio-dG were able to form small spheres or "spherelets" containing 4-10 cells. At day 7, these "spherelets" completely disappeared with 6-thio-dG treatment while the DMSO treated spherelets continued to grow. The inventors then evaluated the effect of continuous and discontinuous exposure to 6-thio-dG after an initial treatment of 2 days. Both treatment schemes showed a robust growth inhibition and sustained TIF formation indicating that the effect of 6-thio-dG treatment persists several days after drug withdrawal (FIG. 3D). These data demonstrate the telomerase-dependent induction of TIFs and their persistence even after the drug is removed, providing a possible explanation for the sustained G$_2$/M arrest. Together these results indicate that 6-thio-dG effect on cell growth is dependent on telomerase-induced TIFs probably in conjunction with genomic DNA damage and this compound is active in brain tumor cells derived from therapy-resistant patients' tumors.

Figure 4B:
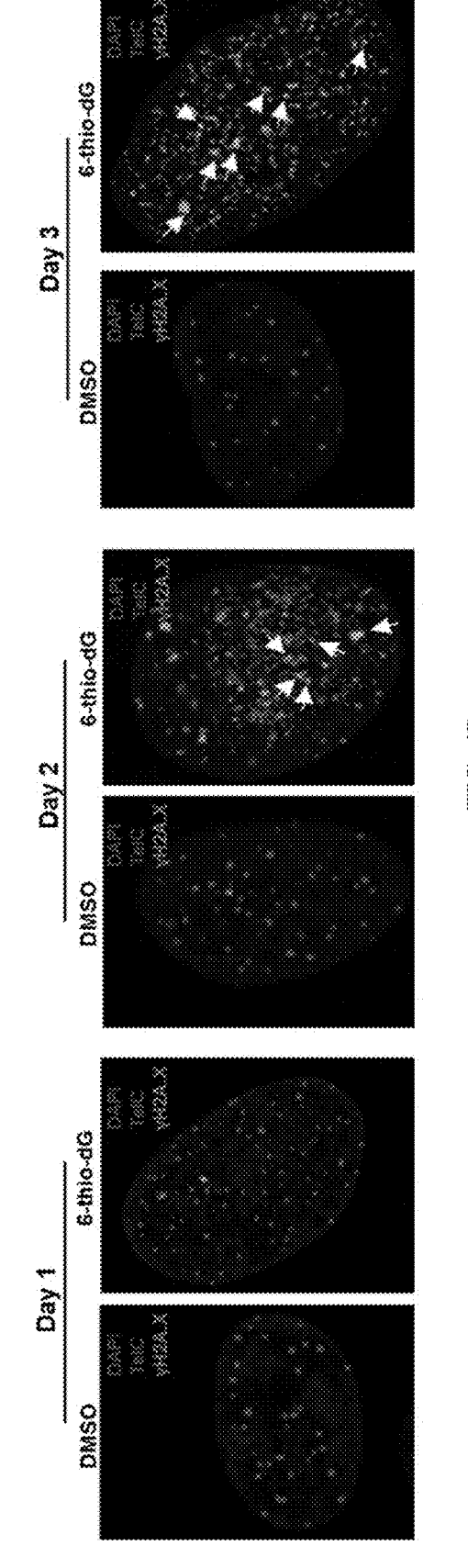

Sequential activation of ATR and ATM pathways in response to 6-thio-dG-induced telomere damage. ATM and ATR-kinases are master regulators of DDR signaling. The inventors and others have shown that telomere dysfunction induces ATM-dependent DDR (2,3). To extend the characterization of 6-thio-dG-induced telomere damage, they investigated ATM and ATR DDR in telomerase-positive cells HFF+hTERT and in matched telomerase-negative cells HFF. Both ATM and ATR signaling pathways were engaged in response to 6-thio-dG treatment in HFF+hTERT as evidenced by the accumulation of ATR-T1989 and ATM-S1981 phosphorylation (FIG. 4A), whereas 6-thio-dG treatment in telomerase-negative cells correlated with the activation of the ATR pathway, probably due to genomic DNA damage. Timing-wise, the ATR pathway was first activated then progressively inhibited (FIG. 4A). The decrease in ATR signaling overlapped with ATM pathway activation. While at day 1 the inventors did not observe TIF formation, the number of TIFs per cell and the number of cells with TIFs markedly increased from day 1 to day 3 in the HFF+hTERT cells (FIG. 4B). This increase correlated with a sustained increase of ATM activation from day 2 to day 3 and a decrease of ATR activation starting at day 2. To investigate 6-thio-dG-induced DDR further, HFF+hTERT cells were pre-treated with a specific ATM or ATR inhibitor for two hours prior to 6-thio-dG treatment for 48 hours. In the presence of either ATM or ATR inhibitor, the inventors observed a reduction in the number of cells with TIFs as well as the number of TIFs per individual cells (FIG. 4C). Compared to ATR inhibition, ATM inhibition led to lower number of TIFs per individual cell. The inventors interpret these results to suggest that 6-thio-dG-induced telomere damage sequentially activates the ATR pathway followed by ATM activation and the formation of TIFs is primarily induced by ATM pathway in normal cells.

Figure 5A:
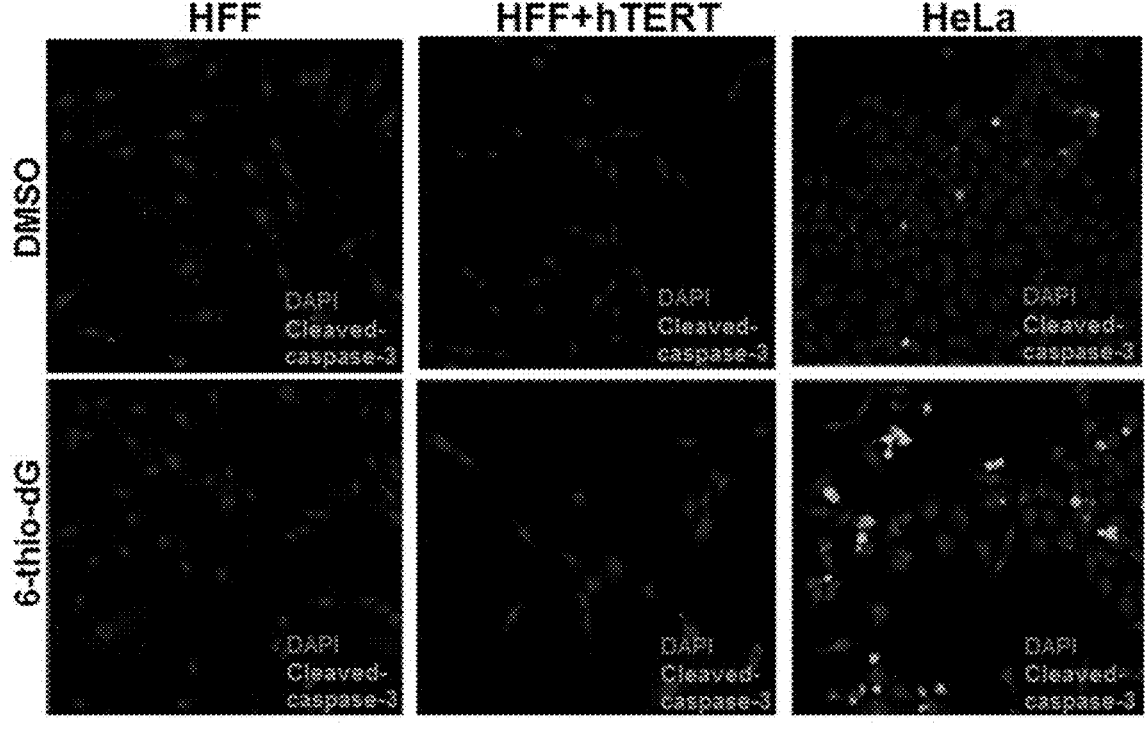
FIGS. 5A-C. 6-thio-dG induces apoptosis in telomerase-positive cancer cells and senescence in telomerase-positive normal cells.
Figure 5B:
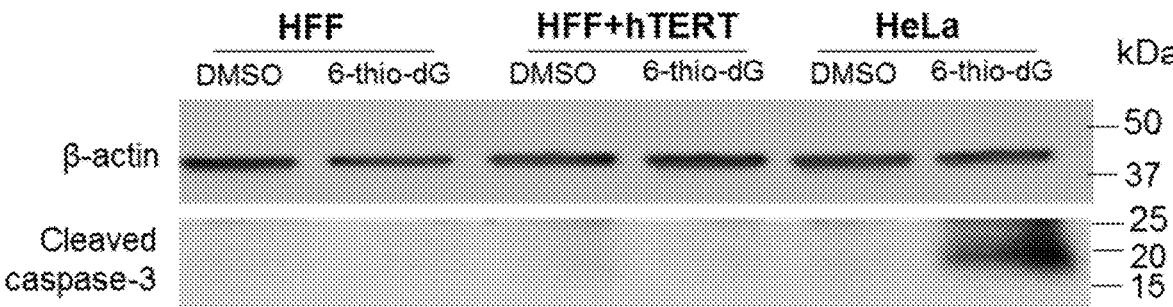
Figure 5C:
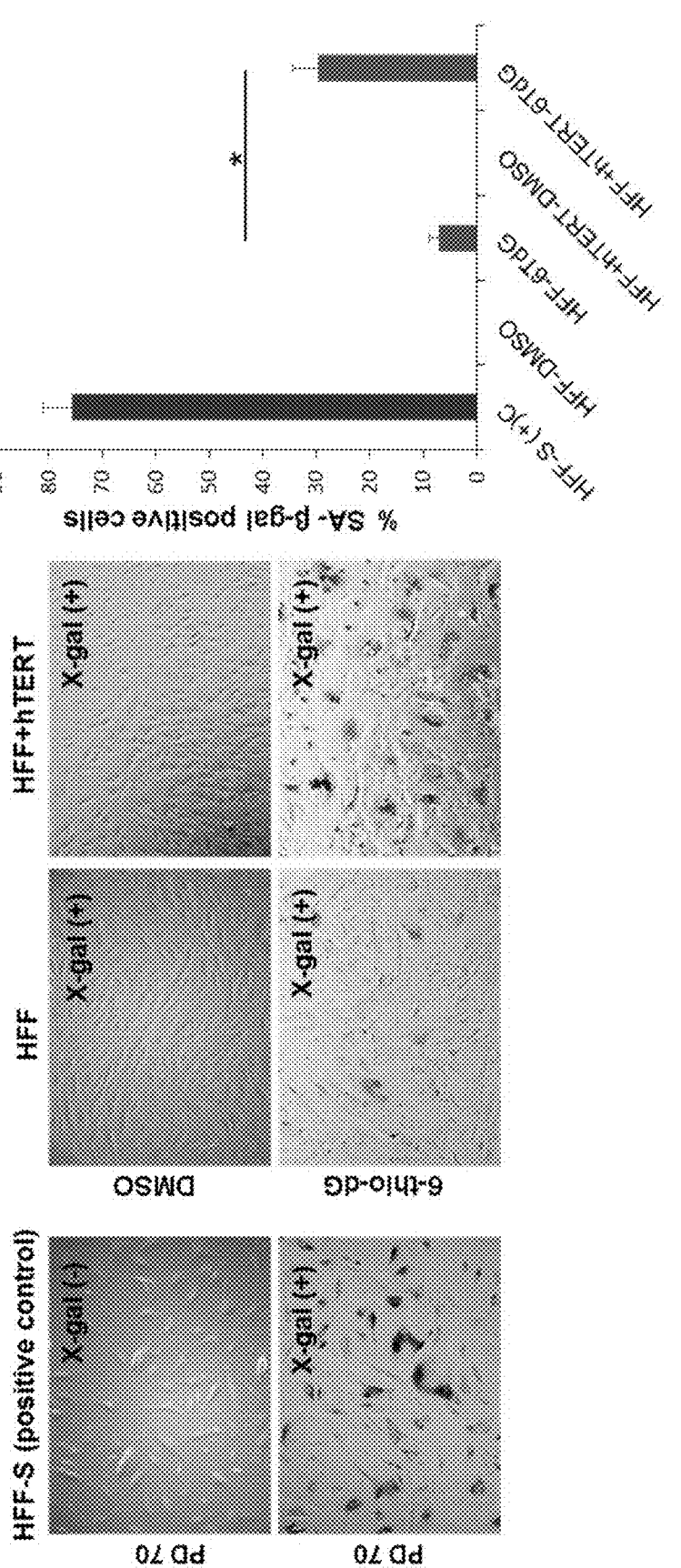

6-thio-dG induced apoptosis in telomerase-positive cancer cells and senescence in telomerase-positive normal cells. The inventors have previously demonstrated that ATM activation, γH2AX-focus formation, and p53 accumulation increased in pre-senescent cells (2). Therefore, they sought to investigate the ultimate fate of cancer telomerase-positive cells, HeLa, MB004, CCHMC-DIPG-1, and the primary normal human cells: HFF (telomerase-negative) and HFF+ hTERT (telomerase-positive) treated with 6-thio-dG. The cells were treated with 3 μM of 6-thio-dG for 4 or 7 days and were evaluated for apoptosis. While HeLa (FIG. 5A), MB004 and CCHMC-DIPG-1 (data now shown) cells showed an increase in cleaved caspase-3 signal, HFF and HFF+hTERT did not show any evidence of apoptosis (FIG. 5A-B). The inventors further evaluated the effect of long-term exposure of HFF and HFF+hTERT cells to 6-thio-dG. The cells were incubated with 3 μM of 6-thio-dG for 23 days Prolonged exposure to 6-thio-dG induced a senescence phenotype in 30% of HFF+hTERT cells as assessed by staining for senescence-associated β-galactosidase activity (SA-β-gal) while only 7% of HFF cells were SA-β-gal-positive (FIG. 5C), suggesting that the senescence observed in HFF+hTERT cells was due to 6-thio-dG-induced telomere dysfunction. Thus, short-term treatment with 6-thio-dG causes apoptosis in telomerase-positive cancer cells and the long-term treatment leads to senescence in telomerase-positive normal cells. These results are reminiscent of replicative senescence caused by persistent telomere damage. Interestingly, unlike cancer telomerase-positive cells, fast growing telomerase-negative cancer cells, U2OS, treated with 6-thio-dG, predominantly did not die (FIGS. 10A-C). After an initial growth inhibition, probably to repair the genomic DNA damage, the cells resumed cell growth several days post-drug removal (FIG. 10B). Finally, the inventors did not observe any DNA fragmentation after treatment with 6-thio-dG (FIG. 10D). These data indicate that the cell death observed in telomerase-positive cancer cells is not due to cell growth kinetics or genomic DNA fragmentation but rather due to telomere damage probably in combination with genomic DNA damage.

Figure 6A:
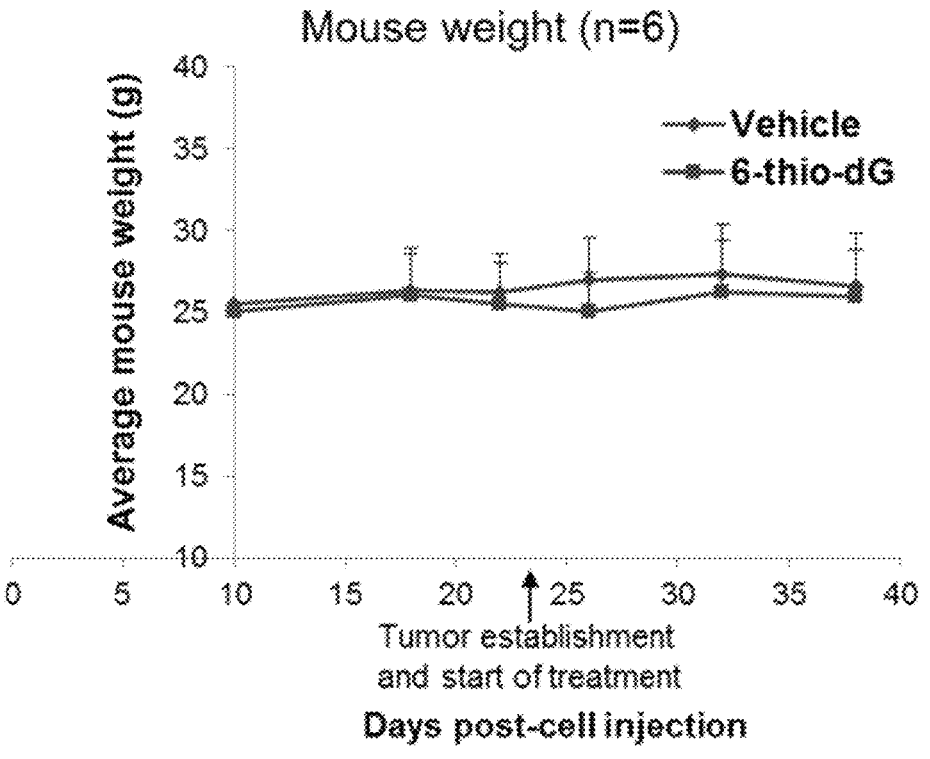
Figure 6B:
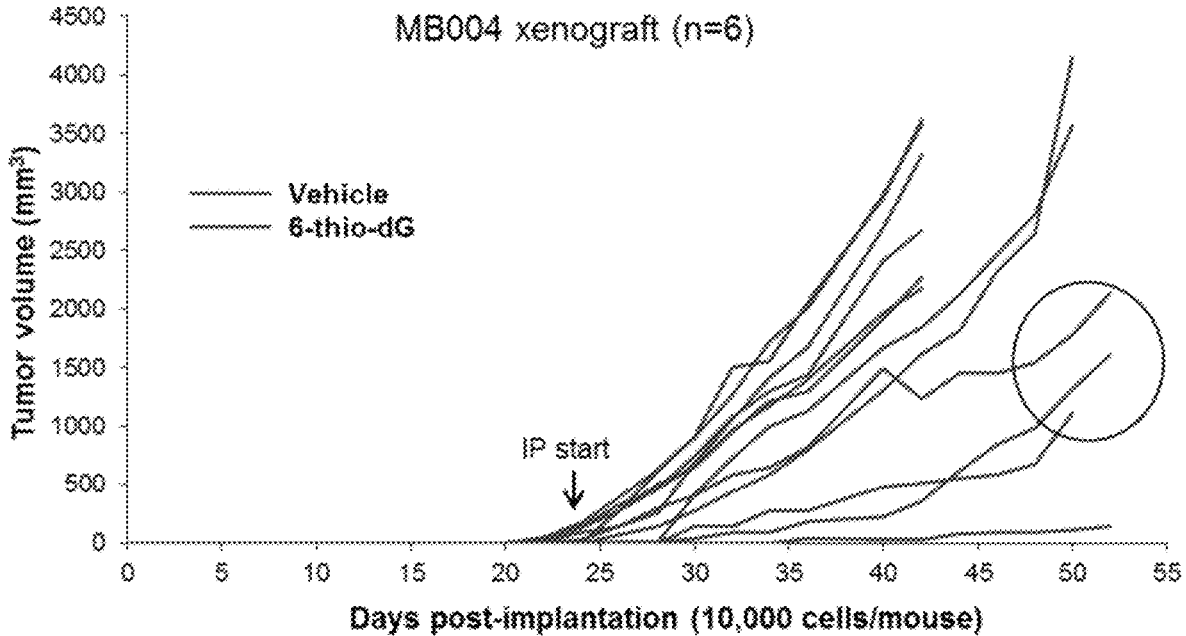
Figure 6D:
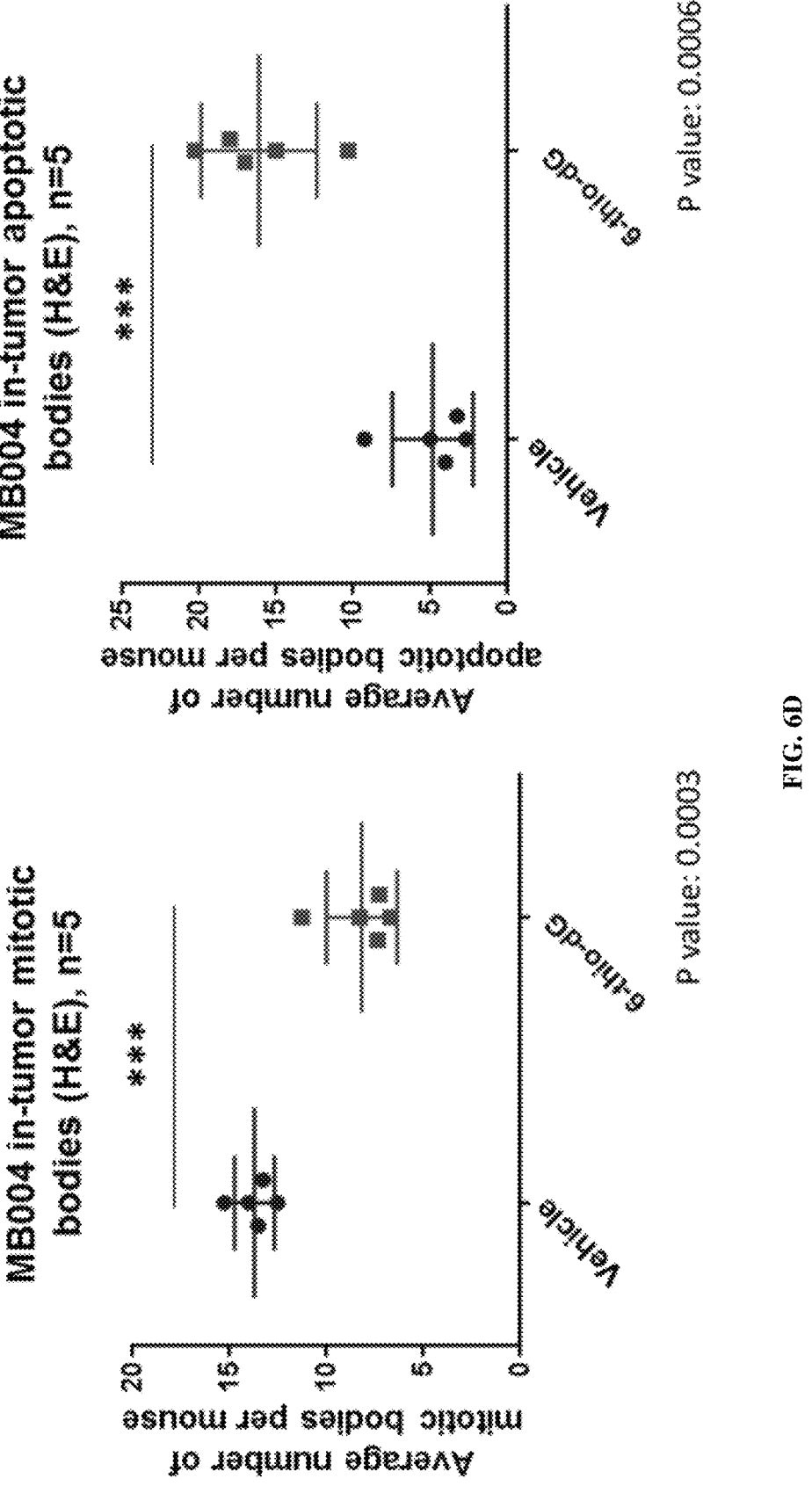
Figure 11:
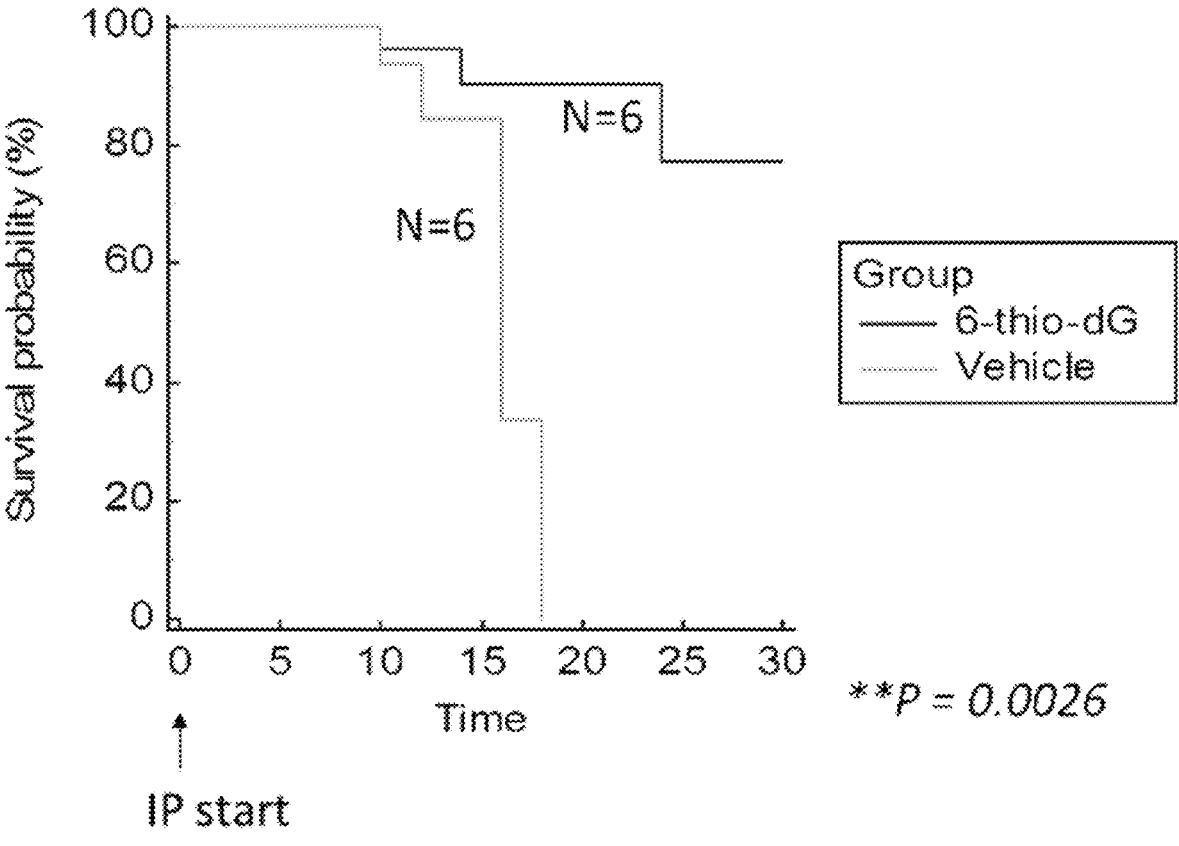
FIG. 11. Survival probability of 6-thio-dG treated mice with MB004 tumors at a volume of 1500 mm$^3$. Average values of 6 mice per group have been considered and significance between two groups is indicated by P-value, **, P<0.01.

6-thio-dG treatment inhibited tumor growth in pediatric high-risk group-3 medulloblastoma xenografts by inducing an increase in in-tumor telomere dysfunction, a decrease of tumor mitotic index and apoptosis. To evaluate the in vivo activity of 6-thio-dG, the inventors subcutaneously injected primary patient-derived stem-like cells MB004 in athymic nude mice (10,000 cells/mouse). They previously observed that these cells form aggressive and fast-growing tumors in mice. Tumors were established at 24 days post-implantation at which point the tumor volumes ranged from 100 to 200 mm$^3$. A mixture of DMSO and PBS solution was used as vehicle control in 6 mice. To monitor 6-thio-dG toxicity in mice, the inventors weighed both treated and untreated mice. They did not observe a noticeable weight difference between the two groups of mice, and no dehydration or clinical symptom of sickness were observed in the treated group, indicating that this 6-thio-dG regimen is not toxic (FIG. 6A). Tumor growth kinetics showed the majority of treated mice had a slower tumor growth rate compared to the untreated group (FIG. 6B). Four out of six treated mice had reduced, or delayed tumor growth. Two out of six treated mice showed fast tumor growth, most likely due to the tumor aggressive nature and bigger tumor volume at the start of 6-thio-dG treatment. Immunohistochemistry of cleaved caspase-3 was performed in five tumors from each group to evaluate in-tumor apoptosis. Compared to the control group, the inventors observed a significant increase in apoptosis in the treated group with a higher increase in tumors with slower growth (FIGS. 6B-C). Accordingly, hematoxylin and eosin staining (H & E) showed a significant decrease in number of mitotic figures and an increase in apoptotic bodies in 6-thio-dG treated mice compared to untreated group (FIG. 6D). FISH staining using a combination of a telomeric probe and 53BP1 immunostaining, showed a marked in-tumor increase of TIFs compared to untreated tumors (FIG. 6E). More than 21% of cells showed at least 1-3 TIFs in the 6-thio-dG group while only ~6% in the control group (FIG. 6E). Moreover, a population of cells with 4-6 TIFs per cell was detected only in treated tumors. The probability of animal survival was significantly higher in 6-thio-dG treated mice compared to the vehicle group upon reaching the tumor volume at a size of 1500 mm³ (≥6 times of initial volume) considered to be a tumor burden (FIG. 11). Together, these data can be interpreted to indicate that 6-thio-dG treatment inhibits the growth of therapy-resistant MB004 tumors by inducing telomere dysfunction, inhibition of cell growth and apoptosis.

Figures 6F, 6G:
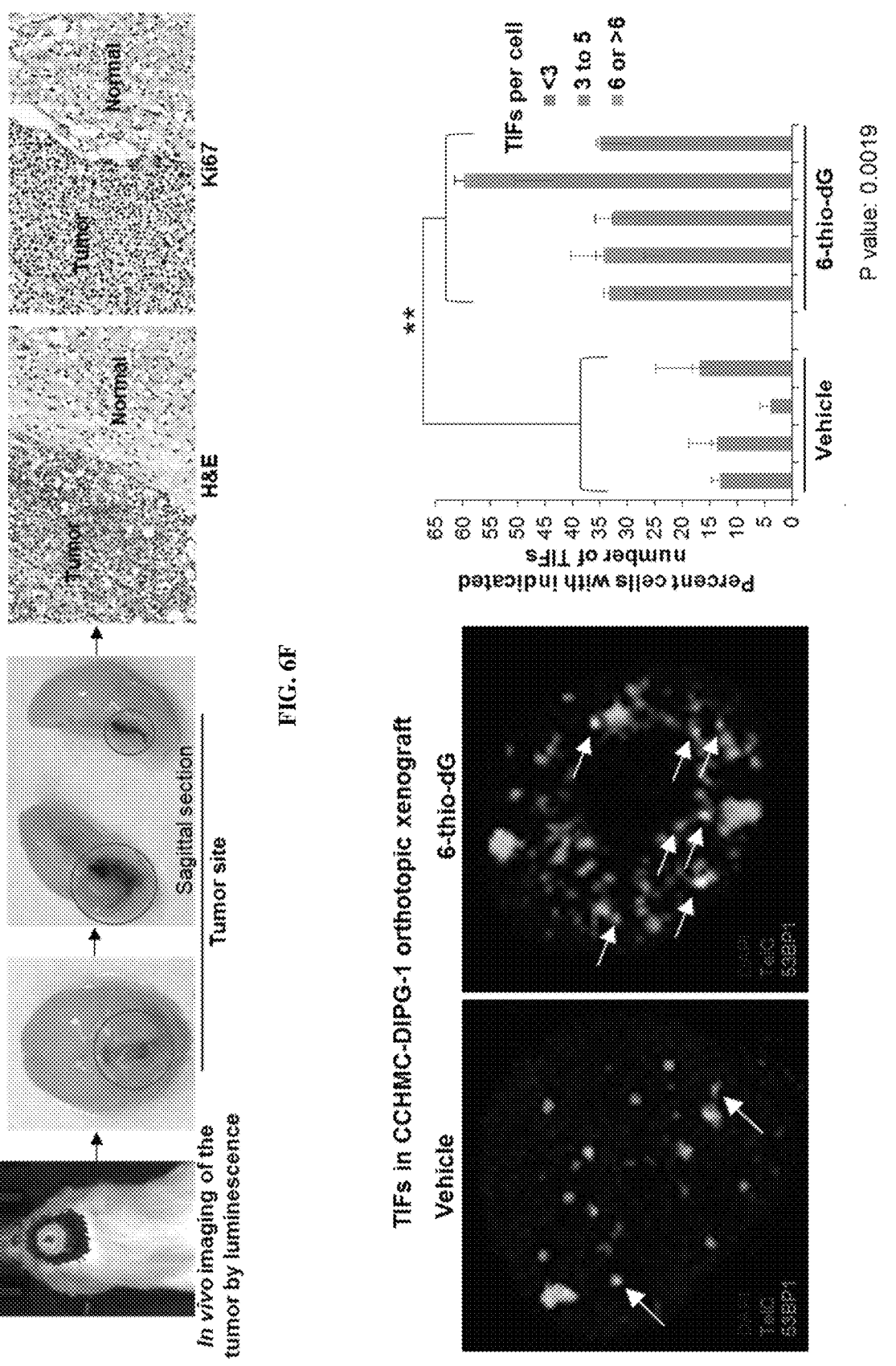

6-thio-dG reached the tumor site and induced intratumoral TIFs in an orthotopic patient-derived xenograft model of diffuse intrinsic pontine glioma. To investigate the penetration and activity of 6-thio-dG in patient-derived brain tumors xenografted into mice, the inventors injected intracranially luciferase-positive DIPG patient-derived primary cancer stem-like cells, CCHMC-DIPG-1, into the pons of the mouse brain using a stereotactic device. Tumor growth was monitored by bioluminescence imaging of the mouse brain (FIG. 6F). Upon tumor establishment at 8-10 days post-implantation, 6-thio-dG or DMSO-PBS administration was started by intraperitoneal injection. The mice were treated for 7-8 days (4-5 doses in total). Mouse brains were collected for analyses after animal euthanasia. The tumors were highly aggressive and histopathological staining using H & E and Ki67 indicated high cellularity and proliferation of tumor tissue compared to matched normal brain (FIG. 6F). Telomerase activity was retained in the xenograft relative to the patient-derived neurosphere cells (FIG. 12A). FISH analyses of 6-thio-dG treated orthotopic tumors revealed an increase in the number of cells with genomic DNA damage and TIFs as well as higher number of TIFs per cell compared to untreated tumors (FIG. 6G). TIFs and genomic DNA damage was not observed in normal mouse brain (FIG. 12B). This indicates that 6-thio-dG reached the tumor in the pons, induced TIFs and genomic DNA damage with no obvious effect on normal brain tissue. Due to the aggressiveness of the tumors, further in vivo studies in orthotopic models of pediatric brain tumors are warranted to evaluate the long-term effect of 6-thio-dG on tumor growth and mouse overall survival.

Example 3—Discussion

Telomerase activity is present in most human cancers but is undetectable in the majority of normal human somatic cells, supporting the rationale of targeting telomerase and telomeres to treat cancer. The inventors' previous clinical trial of imetelstat, a potent direct inhibitor of telomerase, proved intolerable and ineffective in children with recurrent CNS malignancies. The inventors believe that this was due, at least in part, to toxicities, such as thrombocytopenia, which led to CNS bleeding that prevented more frequent dosing of imetelstat to allow sustained inhibition of telomerase. Mender et al. reported that no animal deaths or weight loss were observed in mice treated with 6-thio-dG. Moreover, the treatment did not cause any toxic effects on hematologic counts, liver and kidney functions (17).

Using a lung cancer model, the previous study has demonstrated that 6-thio-dG caused both, in vitro and in vivo telomere damage (TIFs) and induced rapid cancer cell death, likely due to telomerase-dependent telomere uncapping and dysfunction caused by 6-thio-dG treatment (17). In the present study, the inventors sought to evaluate the effect of 6-thio-dG in telomerase-positive primary pediatric brain tumor cells derived from patients with high-risk and treatment-resistant tumors. They found that treatment with 6-thio-dG caused telomere dysfunction and cell growth inhibition in a telomerase specific manner within one week. Interestingly, both cell lines derived from the same patient at diagnosis and at recurrence after chemo- and radiotherapy were sensitive to 6-thio-dG, demonstrating that cells from previously treated and recurrent tumors remain sensitive to 6-thiodG.

Mechanistically, the inventors showed that 6-thio-dG induced $G_2/M$ cell cycle arrest in both telomerase-positive normal (HFF+hTERT) and cancer cells (HeLa and MB004). $G_2/M$ arrest was sustained after 6-thio-dG removal and was associated with apoptosis in cancer cells. Long-term exposure of telomerase-positive normal cells to 6-thio-dG induced senescence, probably due to telomere dysfunction previously shown to be also associated with replicative senescence (2). Interestingly, these data can be interpreted to suggest that 6-thio-dG-induced senescence is initiated in the $G_2/M$ phase, while senescent cells are usually in the $G_1$ phase (32). However, recent publications also support the initiation of senescence from $G_2$ (33-35).

6-thio-dG treatment-induced $G_2/M$ arrest and TIFs formation was sustained several days after drug withdrawal suggesting that a short exposure time in a clinical setting may be sufficient to have a therapeutic effect. It would be informative to investigate a combination treatment with 6-thio-dG and $G_2/M$ checkpoint inhibitors already tested in clinical trials such as AZD0156 (ATM inhibitor), VX-970 (ATR inhibitor) and AZD1775 (WEE1 inhibitor) (36). The expectation is that the cells will progress to M phase causing mitotic catastrophe and massive cell death. 6-thio-dG treatment sequentially activates ATR and ATM DDR pathways. 6-thio-dG activated the ATR but not the ATM pathway in normal telomerase-negative cells. In contrast, 6-thio-dG activated ATR then ATM in normal telomerase-positive cells suggesting that the 6-thio-dG-induced genomic DNA damage activates ATR and then 6-thio-dG-induced telomere damage activates the ATM pathway. However, TIFs could be induced by either pathway if ATR or ATM is inhibited. Thus, it would be informative to evaluate the cell cycle progression in the presence of 6-thio-dG and ATM or ATR inhibitors. Importantly, 6-thio-dG treatment completely abolished neurosphere formation ability, suggesting that self-renewal and stemness are potential targets of 6-thio-dG. Given the extensive genomic DNA damage in telomerase-positive cells, the inventors are not ruling out the possibility that both genomic and telomeric damage contribute to the ultimate fate of the cells in the context of the presence of 6-thio-dG-induced TIFs. Of note, it is well accepted that unlike genomic DNA damage, replicative senescence or apoptosis due to telomere dysfunction does not necessarily depend on the extent of the damage (number of TIFs), but rather on the telomeric localization of the DNA damage. Future studies are required to investigate the link between 6-thio-dG-induced telomere damage and genomic DNA damage.

Using an orthotopic mouse model for DIPG, the inventors showed that 6-thio-dG provided by intraperitoneal injection reached the tumor site in the pons and induced telomere damage in the tumor, demonstrating that 6-thio-dG crossed the blood-brain-barrier. Importantly, they did not observe any adverse effects of 6-thio-dG on normal mouse brain or mouse behavior. In addition to an increase in telomere damage, they also observed an increase in genomic DNA damage, indicating an enhancement of general damage initiated by the 6-thio-dG-induced telomere dysfunction as shown previously (17,37). In future studies, the inventors will optimize the number of injected brain tumor cells in the pons, the dose and the timing of 6-thio-dG administration to evaluate the effect of 6-thio-dG on mouse survival. As this compound is not currently in clinical trials, further testing in multiple animal models is required to fully evaluate efficacy and toxicity.

In conclusion, these findings document that 6-thio-dG is a promising novel approach to treat therapy-resistant pediatric brain tumors and provides a rationale for 6-thio-dG testing as a single agent or in combination with $G_2$/M checkpoint inhibitors already in clinical trials to treat children with high-risk pediatric brain tumors.

TABLE S1

| Genetic Features and Subtypes of the Cell Lines Used | | | | | |
| --- | --- | --- | --- | --- | --- |
| Tumor type | Cell lines | Subtype | TP53 | c-MYC | References |
| Medulloblastoma | MD004 | Group 3 | Mutated | Amplification | 19, 20 |
| | D-425 | Group 3 | Mutated | Amplification | 20, 25 |
| | D-458 | Group 3 | Wild type | Amplification | 20 |

| | Cell lines | Histone status | ATRX | TP53 | References |
| --- | --- | --- | --- | --- | --- |
| GBM | R0315-GBM | H3K27 wild type | Wild type | Wild type | Unpublished |
| DIPG | SU-DIPG-M | H3.3K27M | Not available | Mutated | 21 |
| | CCHMC-DIPG-1 | H3K27 wild type | Not available | Mutated | 22 and data not shown |

TABLE S2

| IC$_{50}$ Values (µM) of 6-thio-dG Treatment for 7 Days in the Cell Lines Used | |
| --- | --- |
| Cell Lines | IC$_{50}$ (µM) |
| HFF | 7.905 |
| SaOS2 | 7.581 |
| HFF + hTERT | 0.1794 |
| HeLa | 0.1431 |
| MB004 | 0.4361 |
| R0315-GBM | 1.247 |
| SU-DIPG-VI | 0.7717 |
| CCHMC-DIPG-1 | 0.6547 |
| D-425 | 1.377 |
| D-458 | 1.452 |

All of the methods disclosed and claimed herein can be made and executed without undue experimentation in light of the present disclosure. While the compositions and methods of this disclosure have been described in terms of particular embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

The following references, to the extent that they provide exemplary procedural or other details supplementary to those set forth herein, are specifically incorporated herein by reference.

1. Palm W, de Lange T. How shelterin protects mammalian telomeres. Annu Rev Genet 2008; 42:301-34 doi 10.1146/annurev.genet.41.110306.130350.

2. Bakkenist C J, Drissi R, Wu J, Kastan M B, Dome J S. Disappearance of the telomere dysfunction-induced stress response in fully senescent cells. Cancer Res 2004; 64(11):3748-52 doi 10.1158/0008-5472.CAN-04-0453.

3. d'Adda di Fagagna F, Reaper P M, Clay-Farrace L, Fiegler H, Carr P, Von Zglinicki T, et al. A DNA damage checkpoint response in telomere-initiated senescence. Nature 2003; 426(6963): 194-8 doi 10.1038/nature02118.

4. Takai H, Smogorzewska A, de Lange T. DNA damage foci at dysfunctional telomeres. Curr Biol 2003; 13(17):1549-56.

5. Kim N W, Piatyszek M A, Prowse K R, Harley C B, West M D, Ho P L, et al. Specific association of human telomerase activity with immortal cells and cancer. Science 1994; 266(5193):2011-5.

6. Shay J W, Bacchetti S. A survey of telomerase activity in human cancer. Eur J Cancer 1997; 33(5):787-91 doi 10.1016/S0959-8049(97)00062-2.

7. Barthel F P, Wei W, Tang M, Martinez-Ledesma E, Hu X, Amin S B, et al. Systematic analysis of telomere length and somatic alterations in 31 cancer types. Nat Genet 2017; 49(3):349-57 doi 10.1038/ng.3781.

8. Smith M A, Seibel N L, Altekruse S F, Ries L A, Melbert D L, O'Leary M, et al. Outcomes for children and adolescents with cancer: challenges for the twenty-first century. J Clin Oncol 2010; 28(15):2625-34 doi 10.1200/JCO.2009.27.0421.

9. Cooney T, Lane A, Bartels U, Bouffet E, Goldman S, Leary S E S, et al. Contemporary survival endpoints: an International Diffuse Intrinsic Pontine Glioma Registry study. Neuro Oncol 2017; 19(9):1279-80 doi 10.1093/neuonc/nox107.

10. Dorris K, Sobo M, Onar-Thomas A, Panditharatna E, Stevenson C B, Gardner S L, et al. Prognostic significance of telomere maintenance mechanisms in pediatric high-grade gliomas. J Neurooncol 2014; 117(1):67-76 doi 10.1007/s11060-014-1374-9.

11. Dikmen Z G, Gellert G C, Jackson S, Gryaznov S, Tressler R, Dogan P, et al. In vivo inhibition of lung cancer by GRN163L: a novel human telomerase inhibitor. Cancer Res 2005; 65(17):7866-73 doi 10.1158/0008-5472.CAN-05-1215.

12. Hochreiter A E, Xiao H, Goldblatt E M, Gryaznov S M, Miller K D, Badve S, et al. Telomerase template antagonist GRN163L disrupts telomere maintenance, tumor growth, and metastasis of breast cancer. Clin Cancer Res 2006; 12(10):3184-92 doi 10.1158/1078-0432.CCR-05-2760.

13. Salloum R, Hummel T R, Kumar S S, Dorris K, Li S, Lin T, et al. A molecular biology and phase II study of imetelstat (GRN163L) in children with recurrent or refractory central nervous system malignancies: a pediatric brain tumor consortium study. J Neurooncol 2016; 129(3):443-51 doi 10.1007/s11060-016-2189-7.

14. Djojosubroto M W, Chin A C, Go N, Schaetzlein S, Manns M P, Gryaznov S, et al. Telomerase antagonists GRN163 and GRN163L inhibit tumor growth and increase chemosensitivity of human hepatoma. Hepatology 2005; 42(5):1127-36 doi 10.1002/hep.20822.

15. Gellert G C, Dikmen Z G, Wright W E, Gryaznov S, Shay J W. Effects of a novel telomerase inhibitor, GRN163L, in human breast cancer. Breast Cancer Res Treat 2006; 96(1):73-81 doi 10.1007/s10549-005-9043-5.

16. Wang E S, Wu K, Chin A C, Chen-Kiang S, Pongracz K, Gryaznov S, et al. Telomerase inhibition with an oligonucleotide telomerase template antagonist: in vitro and in vivo studies in multiple myeloma and lymphoma. Blood 2004; 103(1):258-66 doi 10.1182/blood-2003-02-0546.

17. Mender I, Gryaznov S, Dikmen Z G, Wright W E, Shay J W. Induction of telomere dysfunction mediated by the telomerase substrate precursor 6-thio-2'-deoxyguanosine. Cancer Discov 2015; 5(1):82-95 doi 10.1158/2159-8290.CD-14-0609.

18. Mender I, Gryaznov S, Shay J W. A novel telomerase substrate precursor rapidly induces telomere dysfunction in telomerase positive cancer cells but not telomerase silent normal cells. Oncoscience 2015; 2(8):693-5 doi 10.18632/oncoscience.213.

19. Bandopadhayay P, Bergthold G, Nguyen B, Schubert S, Gholamin S, Tang Y, et al. BET bromodomain inhibition of MYC-amplified medulloblastoma. Clin Cancer Res 2014; 20(4):912-25 doi 10.1158/1078-0432.CCR-13-2281.

20. Ivanov D P, Coyle B, Walker D A, Grabowska A M. In vitro models of medulloblastoma: Choosing the right tool for the job. J Biotechnol 2016; 236:10-25 doi 10.1016/j.jbiotec.2016.07.028.

21. Grasso C S, Tang Y, Truffaux N, Berlow N E, Liu L, Debily M A, et al. Functionally defined therapeutic targets in diffuse intrinsic pontine glioma. Nat Med 2015; 21(7):827 doi 10.1038/nm0715-827a.

22. Kumar S S, Sengupta S, Lee K, Hura N, Fuller C, DeWire M, et al. BMI-1 is a potential therapeutic target in diffuse intrinsic pontine glioma. Oncotarget 2017 doi 10.18632/oncotarget.18002.

23. Monje M, Mitra S S, Freret M E, Raveh T B, Kim J, Masek M, et al. Hedgehog-responsive candidate cell of origin for diffuse intrinsic pontine glioma. Proc Natl Acad Sci USA 2011; 108(11):4453-8 doi 10.1073/pnas.1101657108.

24. Friedman H S, Colvin O M, Kaufmann S H, Ludeman S M, Bullock N, Bigner D D, et al. Cyclophosphamide resistance in medulloblastoma. Cancer Res 1992; 52(19):5373-8.

25. Bigner S H, Friedman H S, Vogelstein B, Oakes W J, Bigner D D. Amplification of the cmyc gene in human medulloblastoma cell lines and xenografts. Cancer Res 1990; 50(8):2347-50.

26. Hickson I, Zhao Y, Richardson C J, Green S J, Martin N M, Orr A I, et al. Identification and characterization of a novel and specific inhibitor of the ataxia-telangiectasia mutated kinase ATM. Cancer Res 2004; 64(24):9152-9 doi 10.1158/0008-5472.CAN-04-2727.

27. Fokas E, Prevo R, Pollard J R, Reaper P M, Charlton P A, Cornelissen B, et al. Targeting ATR in vivo using the novel inhibitor VE-822 results in selective sensitization of pancreatic tumors to radiation. Cell Death Dis 2012; 3:e441 doi 10.1038/cddis.2012.181.

28. Charrier J D, Durrant S J, Golec J M, Kay D P, Knegtel R M, MacCormick S, et al. Discovery of potent and selective inhibitors of ataxia telangiectasia mutated and Rad3 related (ATR) protein kinase as potential anticancer agents. J Med Chem 2011; 54(7):2320-30 doi 10.1021/jm101488z.

29. Herbert B S, Gellert G C, Hochreiter A, Pongracz K, Wright W E, Zielinska D, et al. Lipid modification of GRN163, an N3'→P5' thio-phosphoramidate oligonucleotide, enhances the potency of telomerase inhibition. Oncogene 2005; 24(33):5262-8 doi 10.1038/sj.onc.1208760.

30. Zhou B B, Zhang H, Damelin M, Geles K G, Grindley J C, Dirks P B. Tumour-initiating cells: challenges and opportunities for anticancer drug discovery. Nat Rev Drug Discov 2009; 8(10):806-23 doi 10.1038/nrd2137.

31. He X M, Ostrowski L E, von Wronski M A, Friedman H S, Wikstrand C J, Bigner S H, et al. Expression of 06-methylguanine-DNA methyltransferase in six human medulloblastoma cell lines. Cancer Res 1992; 52(5):1144-8.

32. Jacobs J J, de Lange T. Significant role for p16INK4a in p53-independent telomere-directed senescence. Curr Biol 2004; 14(24):2302-8 doi 10.1016/j.cub.2004.12.025.

33. Johmura Y, Shimada M, Misaki T, Naiki-Ito A, Miyoshi H, Motoyama N, et al. Necessary and sufficient role for a mitosis skip in senescence induction. Mol Cell 2014; 55(1):73-84 doi 10.1016/j.molcel.2014.05.003.

34. Krenning L, Feringa F M, Shaltiel I A, van den Berg J, Medema R H. Transient activation of p53 in G2 phase is sufficient to induce senescence. Mol Cell 2014; 55(1):59-72 doi 10.1016/j.molcel.2014.05.007.

35. Mullers E, Silva Cascales H, Jaiswal H, Saurin A T, Lindqvist A. Nuclear translocation of Cyclin B1 marks the restriction point for terminal cell cycle exit in G2 phase. Cell Cycle 2014; 13(17):2733-43 doi 10.4161/15384101.2015.945831.

36. Brown J S, O'Carrigan B, Jackson S P, Yap T A. Targeting DNA Repair in Cancer: Beyond PARP Inhibitors. Cancer Discov 2017; 7(1):20-37 doi 10.1158/2159-8290.CD-16-0860.

37. Feldser D M, Hackett J A, Greider C W. Telomere dysfunction and the initiation of genome instability. Nat Rev Cancer 2003; 3(8):623-7 doi 10.1038/nrc1142.

What is claimed is:

1. A method of treating a diffuse intrinsic pontine glioma (DIPG) in a pediatric subject, comprising administering 6-thio-2'deoxyguanosine (6-thio-dG) to a subject in need thereof, thereby treating pediatric brain cancer.

2. The method of claim 1, wherein the subject's is age 1-21 years of age.

3. The method of claim 1, wherein the DIPG is drug resistant.

4. The method of claim 1, wherein the DIPG has telomerase activity.

5. The method of claim 1, wherein 6-thio-dG induces in vivo telomere dysfunction-induced foci (TIFs), apoptosis, and an inhibition of tumor growth.

6. The method of claim 1, wherein 6-thio-dG is administered in combination or sequentially with a chemotherapeutic agent.

7. The method of claim 1, wherein 6-thio-dG is administered in combination with an immune checkpoint inhibitor.

8. The method of claim 1, further comprising the step of assessing telomerase activity in a brain cancer cell from said subject.

9. The method of claim 7, wherein the immune checkpoint inhibitor is an anti-PD-L1 or PD-1 antibody.

\* \* \* \* \*